US007846666B2

(12) United States Patent
Kurn

(10) Patent No.: US 7,846,666 B2
(45) Date of Patent: Dec. 7, 2010

(54) METHODS OF RNA AMPLIFICATION IN THE PRESENCE OF DNA

(75) Inventor: Nurith Kurn, Palo Alto, CA (US)

(73) Assignee: NuGen Technologies, Inc., San Carlos, CA (US)

( * ) Notice: Subject to any disclaimer, the term of this patent is extended or adjusted under 35 U.S.C. 154(b) by 0 days.

(21) Appl. No.: 12/408,493

(22) Filed: Mar. 20, 2009

(65) Prior Publication Data
US 2009/0239232 A1    Sep. 24, 2009

Related U.S. Application Data

(60) Provisional application No. 61/038,696, filed on Mar. 21, 2008, provisional application No. 61/074,991, filed on Jun. 23, 2008, provisional application No. 61/085,811, filed on Aug. 1, 2008.

(51) Int. Cl.
C12Q 1/68    (2006.01)
(52) U.S. Cl. .......................................................... 435/6
(58) Field of Classification Search ....................... None
See application file for complete search history.

(56) References Cited

U.S. PATENT DOCUMENTS

| | | |
|---|---|---|
| 3,996,345 A | 12/1976 | Ullman et al. |
| 3,999,345 A | 12/1976 | McKelvey |
| 4,174,384 A | 11/1979 | Ullman et al. |
| 4,261,968 A | 4/1981 | Ullman et al. |
| 4,362,867 A | 12/1982 | Paddock |
| 4,458,066 A | 7/1984 | Caruthers et al. |
| 4,582,788 A | 4/1986 | Erlich |
| 4,683,194 A | 7/1987 | Saiki et al. |
| 4,786,600 A | 11/1988 | Kramer et al. |
| 4,876,187 A | 10/1989 | Duck et al. |
| 4,908,385 A | 3/1990 | Bar-Tana et al. |
| 4,996,143 A | 2/1991 | Heller et al. |
| 5,011,769 A | 4/1991 | Duck et al. |
| 5,043,272 A | 8/1991 | Hartley |
| 5,090,591 A | 2/1992 | Long |
| 5,106,727 A | 4/1992 | Hartley et al. |
| 5,130,238 A | 7/1992 | Malek et al. |
| 5,169,766 A | 12/1992 | Schuster et al. |
| 5,175,243 A | 12/1992 | Ash |
| 5,185,243 A | 2/1993 | Ullman et al. |
| 5,194,370 A | 3/1993 | Berninger et al. |
| 5,262,311 A | 11/1993 | Pardee et al. |
| 5,270,184 A | 12/1993 | Walker et al. |
| 5,328,985 A | 7/1994 | Sano et al. |
| 5,340,716 A | 8/1994 | Ullman et al. |
| 5,399,491 A | 3/1995 | Kacian et al. |
| 5,403,711 A | 4/1995 | Walder et al. |
| 5,409,818 A | 4/1995 | Davey et al. |
| 5,427,911 A | 6/1995 | Ruano |
| 5,427,929 A | 6/1995 | Richards et al. |
| 5,427,930 A | 6/1995 | Birkenmeyer et al. |
| 5,437,990 A | 8/1995 | Burg et al. |
| 5,455,166 A | 10/1995 | Walker |
| 5,480,784 A | 1/1996 | Kacian et al. |
| 5,491,063 A | 2/1996 | Fisher et al. |
| 5,508,178 A | 4/1996 | Rose et al. |
| 5,510,270 A | 4/1996 | Fodor et al. |
| 5,545,522 A * | 8/1996 | Van Gelder et al. ........... 506/26 |
| 5,554,516 A | 9/1996 | Kacian et al. |
| 5,554,517 A | 9/1996 | Davey et al. |
| 5,556,752 A | 9/1996 | Lockhart et al. |
| 5,556,771 A | 9/1996 | Shen et al. |
| 5,565,322 A | 10/1996 | Heller |
| 5,578,832 A | 11/1996 | Trulson et al. |
| 5,589,339 A | 12/1996 | Hampson et al. |
| 5,595,891 A | 1/1997 | Rose et al. |
| 5,616,478 A | 4/1997 | Chetverin et al. |
| 5,641,658 A | 6/1997 | Adams et al. |
| 5,648,211 A | 7/1997 | Fraiser et al. |
| 5,654,142 A | 8/1997 | Kievits et al. |
| 5,660,988 A | 8/1997 | Duck et al. |
| 5,665,539 A | 9/1997 | Sano et al. |
| 5,665,545 A | 9/1997 | Malek et al. |
| 5,665,845 A | 9/1997 | Allman |
| 5,679,512 A | 10/1997 | Laney et al. |
| 5,679,524 A | 10/1997 | Nikiforov et al. |
| 5,683,879 A | 11/1997 | Laney et al. |
| 5,686,272 A | 11/1997 | Marshall et al. |
| 5,688,648 A | 11/1997 | Mathies et al. |
| 5,693,502 A | 12/1997 | Gold et al. |
| 5,700,642 A | 12/1997 | Monforte et al. |
| 5,708,154 A | 1/1998 | Smith et al. |
| 5,709,994 A | 1/1998 | Pease et al. |

(Continued)

FOREIGN PATENT DOCUMENTS

EP    0050424 A1    4/1982

(Continued)

OTHER PUBLICATIONS

U.S. Appl. No. 60/255,638, filed Dec. 13, 2000, Kurn.

(Continued)

*Primary Examiner*—Christopher M. Babic
(74) *Attorney, Agent, or Firm*—Wilson, Sonsini, Goodrich & Rosati

(57) ABSTRACT

The invention provides methods for amplification of RNA. The methods are particularly suitable for specifically amplifying RNA in the presence of DNA. The methods involve producing a marked first primer extension product from a target RNA in the presence of a DNA-dependent DNA polymerase inhibitor, which prevents replication of DNA by the reverse transcriptase enzyme. The marked nucleic acid products are subsequently selectively amplified in the presence on non-marked nucleic acids. The methods are useful for production and analysis of polynucleotide sequences complementary to an RNA sequence. The methods are useful for preparation of nucleic acid libraries and substrates for analysis of gene expression of cells in biological samples. The invention also provides compositions and kits for practicing the amplification methods, as well as methods which use the amplification products.

46 Claims, 7 Drawing Sheets

U.S. PATENT DOCUMENTS

| | | |
|---|---|---|
| 5,710,028 A | 1/1998 | Eyal et al. |
| 5,712,124 A | 1/1998 | Walker |
| 5,712,127 A | 1/1998 | Malek et al. |
| 5,716,785 A | 2/1998 | Van Gelder et al. |
| 5,731,146 A | 3/1998 | Duck et al. |
| 5,731,171 A | 3/1998 | Bohlander |
| 5,744,308 A | 4/1998 | Guillou-Bonnici et al. |
| 5,744,312 A | 4/1998 | Mamone et al. |
| 5,747,255 A | 5/1998 | Brenner |
| 5,763,178 A | 6/1998 | Chirikjian et al. |
| 5,766,846 A | 6/1998 | Schlossmacher et al. |
| 5,766,849 A | 6/1998 | McDonough et al. |
| 5,773,601 A | 6/1998 | Agrawal |
| 5,811,238 A | 9/1998 | Stemmer et al. |
| 5,824,517 A | 10/1998 | Cleuziat et al. |
| 5,824,518 A | 10/1998 | Kacian et al. |
| 5,829,547 A | 11/1998 | Fujii et al. |
| 5,830,655 A | 11/1998 | Monforte et al. |
| 5,830,721 A | 11/1998 | Stemmer et al. |
| 5,837,832 A | 11/1998 | Chee et al. |
| 5,846,710 A | 12/1998 | Bajaj |
| 5,849,478 A | 12/1998 | Cashman |
| 5,849,542 A | 12/1998 | Reeve et al. |
| 5,849,547 A | 12/1998 | Cleuziat et al. |
| 5,854,033 A | 12/1998 | Lizardi et al. |
| 5,858,665 A | 1/1999 | Hepp et al. |
| 5,871,697 A | 2/1999 | Rothberg et al. |
| 5,876,976 A | 3/1999 | Richards et al. |
| 5,882,867 A | 3/1999 | Ullman et al. |
| 5,888,779 A | 3/1999 | Kacian et al. |
| 5,888,819 A | 3/1999 | Goelet et al. |
| 5,916,777 A | 6/1999 | Kacian et al. |
| 5,925,517 A | 7/1999 | Tyagi et al. |
| 5,932,449 A | 8/1999 | Emanuel et al. |
| 5,932,450 A | 8/1999 | Dattagupta et al. |
| 5,932,451 A | 8/1999 | Wang et al. |
| 5,958,681 A | 9/1999 | Wetmur et al. |
| 5,962,271 A | 10/1999 | Chenchik et al. |
| 5,962,272 A | 10/1999 | Chenchik et al. |
| 5,965,409 A | 10/1999 | Pardee et al. |
| 5,985,548 A | 11/1999 | Collier et al. |
| 6,004,744 A | 12/1999 | Goelet et al. |
| 6,004,745 A | 12/1999 | Arnold, Jr. et al. |
| 6,013,431 A | 1/2000 | Soderlund et al. |
| 6,027,889 A | 2/2000 | Barany et al. |
| 6,027,923 A | 2/2000 | Wallace |
| 6,030,774 A | 2/2000 | Laney et al. |
| 6,037,152 A | 3/2000 | Richards et al. |
| 6,040,138 A | 3/2000 | Lockhart et al. |
| 6,060,288 A | 5/2000 | Adams et al. |
| 6,083,689 A | 7/2000 | Martinelli et al. |
| 6,087,103 A | 7/2000 | Burmer |
| 6,090,591 A | 7/2000 | Burg et al. |
| 6,096,715 A | 8/2000 | Rossi et al. |
| 6,107,032 A | 8/2000 | Kilger et al. |
| 6,107,061 A | 8/2000 | Johnson |
| 6,124,120 A | 9/2000 | Lizardi |
| 6,132,997 A | 10/2000 | Shannon |
| 6,136,533 A | 10/2000 | Bekkaoui et al. |
| 6,140,086 A * | 10/2000 | Fox et al. ............... 435/91.41 |
| 6,143,495 A | 11/2000 | Lizardi et al. |
| 6,159,685 A | 12/2000 | Pinkel et al. |
| 6,183,960 B1 | 2/2001 | Lizardi |
| 6,210,884 B1 | 4/2001 | Lizardi |
| 6,218,105 B1 * | 4/2001 | Hall et al. ....................... 435/5 |
| 6,218,151 B1 | 4/2001 | Cleuziat et al. |
| 6,251,600 B1 | 6/2001 | Winger et al. |
| 6,251,639 B1 | 6/2001 | Kurn |
| 6,255,060 B1 | 7/2001 | Eberwine et al. |
| 6,270,961 B1 | 8/2001 | Drmanac |
| 6,271,002 B1 | 8/2001 | Linsley et al. |
| 6,280,935 B1 | 8/2001 | Macevicz |
| 6,280,949 B1 | 8/2001 | Lizardi |
| 6,291,166 B1 | 9/2001 | Gerdes et al. |
| 6,291,170 B1 | 9/2001 | Van Gelder et al. |
| 6,300,073 B1 * | 10/2001 | Zhao et al. ..................... 435/6 |
| 6,306,365 B1 | 10/2001 | Ruoslahti et al. |
| 6,309,842 B1 | 10/2001 | Dower et al. |
| 6,309,843 B1 | 10/2001 | Timms |
| 6,316,229 B1 | 11/2001 | Lizardi et al. |
| 6,319,714 B1 | 11/2001 | Crameri et al. |
| 6,326,142 B1 | 12/2001 | Royer |
| 6,335,160 B1 | 1/2002 | Patten et al. |
| 6,344,356 B1 | 2/2002 | Stemmer |
| 6,358,712 B1 | 3/2002 | Jarrell et al. |
| 6,365,375 B1 | 4/2002 | Dietmaier et al. |
| 6,410,278 B1 | 6/2002 | Notomi et al. |
| 6,485,944 B1 | 11/2002 | Church et al. |
| 6,617,137 B2 | 9/2003 | Dean et al. |
| 6,673,549 B1 * | 1/2004 | Furness et al. ................. 435/6 |
| 6,686,156 B2 | 2/2004 | Kurn |
| 6,692,918 B2 | 2/2004 | Kurn |
| 6,794,138 B1 | 9/2004 | Cao et al. |
| 6,815,164 B2 | 11/2004 | Kurn |
| 6,858,413 B2 | 2/2005 | Kurn |
| 6,927,024 B2 | 8/2005 | Dodge et al. |
| 6,946,251 B2 | 9/2005 | Kurn |
| 6,949,633 B1 | 9/2005 | Monforte et al. |
| 6,951,722 B2 | 10/2005 | Mukai et al. |
| 7,056,671 B2 | 6/2006 | Enoki et al. |
| 7,094,536 B2 | 8/2006 | Kurn |
| 7,176,025 B2 | 2/2007 | Kurn |
| 7,294,461 B2 | 11/2007 | Kurn |
| 7,351,557 B2 | 4/2008 | Kurn |
| 7,354,717 B2 | 4/2008 | Kurn |
| 7,402,386 B2 | 7/2008 | Kurn et al. |
| 7,534,569 B2 | 5/2009 | Chang et al. |
| 2001/0000077 A1 | 3/2001 | Engelhardt et al. |
| 2001/0034048 A1 | 10/2001 | Kurn |
| 2001/0041334 A1 | 11/2001 | Rashtchian et al. |
| 2002/0028447 A1 | 3/2002 | Lee et al. |
| 2002/0058270 A1 | 5/2002 | Kurn |
| 2002/0064837 A1 | 5/2002 | Trinh et al. |
| 2002/0115088 A1 | 8/2002 | Kurn |
| 2002/0127575 A1 | 9/2002 | Hoke et al. |
| 2002/0142309 A1 | 10/2002 | Dattagupta |
| 2002/0164628 A1 | 11/2002 | Kurn |
| 2002/0177141 A1 | 11/2002 | Chee et al. |
| 2003/0017591 A1 | 1/2003 | Kurn |
| 2003/0049657 A1 | 3/2003 | Cherry |
| 2003/0073081 A1 | 4/2003 | Mukai et al. |
| 2003/0087251 A1 | 5/2003 | Kurn |
| 2003/0104460 A1 | 6/2003 | Rabbani et al. |
| 2003/0186234 A1 | 10/2003 | Kurn |
| 2003/0204331 A1 * | 10/2003 | Whitney et al. ............... 702/32 |
| 2003/0215926 A1 | 11/2003 | Kurn et al. |
| 2004/0005614 A1 | 1/2004 | Kurn et al. |
| 2004/0023271 A1 | 2/2004 | Kurn et al. |
| 2004/0033499 A1 | 2/2004 | Ilsley |
| 2004/0096853 A1 | 5/2004 | Mayer |
| 2004/0203019 A1 | 10/2004 | Kurn et al. |
| 2004/0203025 A1 | 10/2004 | Kurn |
| 2005/0003441 A1 | 1/2005 | Kurn |
| 2005/0014192 A1 | 1/2005 | Kurn |
| 2005/0019793 A1 | 1/2005 | Kurn et al. |
| 2005/0064456 A1 | 3/2005 | Kurn |
| 2005/0079510 A1 | 4/2005 | Berka et al. |
| 2005/0123950 A1 | 6/2005 | Mukai et al. |
| 2005/0130173 A1 | 6/2005 | Leamon et al. |
| 2005/0208538 A1 | 9/2005 | Kurn et al. |
| 2006/0008824 A1 | 1/2006 | Ronaghi et al. |
| 2006/0014182 A1 | 1/2006 | Kurn |
| 2006/0246434 A1 | 11/2006 | Erlander et al. |
| 2006/0269934 A1 | 11/2006 | Woudenberg et al. |

| | | | |
|---|---|---|---|
| 2007/0054301 A1 | 3/2007 | Becker et al. | |
| 2008/0176311 A1 | 7/2008 | Kurn | |
| 2008/0182300 A1 | 7/2008 | Kurn | |
| 2009/0036663 A1 | 2/2009 | Kurn | |
| 2009/0068709 A1 | 3/2009 | Kurn et al. | |
| 2009/0130721 A1 | 5/2009 | Kurn et al. | |
| 2009/0203085 A1 | 8/2009 | Kurn et al. | |
| 2009/0203531 A1 | 8/2009 | Kurn et al. | |
| 2009/0233804 A1 | 9/2009 | Kurn et al. | |
| 2009/0275486 A1 | 11/2009 | Kurn et al. | |
| 2010/0022403 A1 | 1/2010 | Kurn et al. | |

FOREIGN PATENT DOCUMENTS

| | | |
|---|---|---|
| EP | 0084796 B1 | 8/1983 |
| EP | 0201184 B1 | 11/1986 |
| EP | 0237362 B1 | 9/1987 |
| EP | 0258017 B1 | 3/1988 |
| EP | 0320308 B1 | 6/1989 |
| EP | 0365627 B1 | 5/1990 |
| EP | 0395398 A2 | 10/1990 |
| EP | 0395398 A3 | 10/1990 |
| EP | 0497272 B1 | 8/1992 |
| EP | 0500224 A2 | 8/1992 |
| EP | 0505012 B1 | 9/1992 |
| EP | 0543612 B1 | 5/1993 |
| EP | 0329822 B1 | 6/1994 |
| EP | 0667393 A2 | 8/1995 |
| EP | 0667393 A3 | 8/1995 |
| EP | 0497271 B1 | 10/1996 |
| EP | 0878553 B1 | 11/1998 |
| EP | 0971039 A2 | 1/2000 |
| EP | 0971039 A3 | 1/2000 |
| EP | 1055736 A1 | 11/2000 |
| EP | 1167524 A1 | 1/2002 |
| EP | 1273737 A2 | 1/2003 |
| EP | 1275737 A2 | 1/2003 |
| EP | 1281757 A1 | 2/2003 |
| EP | 1312682 A1 | 5/2003 |
| JP | 6327500 A | 11/1994 |
| JP | 7023799 A | 1/1995 |
| WO | WO 88/02746 A1 | 4/1988 |
| WO | WO 88/10315 A1 | 12/1988 |
| WO | WO 89/01050 A1 | 2/1989 |
| WO | WO 90/01069 A1 | 2/1990 |
| WO | WO 92/15712 A1 | 9/1992 |
| WO | WO 92/18521 A1 | 10/1992 |
| WO | WO 93/15229 A2 | 8/1993 |
| WO | WO 95/03426 A2 | 2/1995 |
| WO | WO 93/15229 A3 | 3/1995 |
| WO | WO 95/21271 A1 | 8/1995 |
| WO | WO 97/03207 A1 | 1/1997 |
| WO | WO 97/04123 A1 | 2/1997 |
| WO | WO 97/04126 A1 | 2/1997 |
| WO | WO 97/32040 A2 | 9/1997 |
| WO | WO 97/32040 A3 | 10/1997 |
| WO | WO 98/01050 A1 | 1/1998 |
| WO | WO 98/06736 A1 | 2/1998 |
| WO | WO 98/28443 A1 | 7/1998 |
| WO | WO 98/44151 A1 | 10/1998 |
| WO | WO 98/59066 A1 | 12/1998 |
| WO | WO 99/18241 A1 | 4/1999 |
| WO | WO 99/23256 A1 | 5/1999 |
| WO | WO 99/25873 A1 | 5/1999 |
| WO | WO 99/29901 A1 | 6/1999 |
| WO | WO 99/37808 A1 | 7/1999 |
| WO | WO 99/40219 A1 | 8/1999 |
| WO | WO 99/42618 A1 | 8/1999 |
| WO | WO 99/55912 A1 | 11/1999 |
| WO | WO 00/08208 A2 | 2/2000 |
| WO | WO 00/09745 A1 | 2/2000 |
| WO | WO 00/08208 A3 | 5/2000 |
| WO | WO 00/28082 A1 | 5/2000 |
| WO | WO 00/40715 A2 | 7/2000 |
| WO | WO 00/52191 A1 | 9/2000 |
| WO | WO 00/56877 A1 | 9/2000 |
| WO | WO 00/56925 A2 | 9/2000 |
| WO | WO 00/56925 A3 | 9/2000 |
| WO | WO 00/70095 A2 | 11/2000 |
| WO | WO 01/20035 A2 | 3/2001 |
| WO | WO 01/20035 A3 | 3/2001 |
| WO | WO 01/23613 A1 | 4/2001 |
| WO | WO 00/70095 A3 | 8/2001 |
| WO | WO 01/64952 A2 | 9/2001 |
| WO | WO 01/73134 A2 | 10/2001 |
| WO | WO 02/000938 A2 | 1/2002 |
| WO | WO 02/06533 A2 | 1/2002 |
| WO | WO 02/28876 A2 | 4/2002 |
| WO | WO 02/29117 A2 | 4/2002 |
| WO | WO 02/48402 A2 | 6/2002 |
| WO | WO 02/057487 A2 | 7/2002 |
| WO | WO 02/057487 A3 | 7/2002 |
| WO | WO 02/28876 A3 | 8/2002 |
| WO | WO 02/072772 A2 | 9/2002 |
| WO | WO 02/072773 A2 | 9/2002 |
| WO | WO 01/64952 A3 | 12/2002 |
| WO | WO 02/103013 A2 | 12/2002 |
| WO | WO 01/73134 A3 | 1/2003 |
| WO | WO 03/012100 A2 | 2/2003 |
| WO | WO 03/012100 A3 | 2/2003 |
| WO | WO 03/012142 A1 | 2/2003 |
| WO | WO 02/103013 A3 | 3/2003 |
| WO | WO 02/06533 A3 | 4/2003 |
| WO | WO 02/000938 A3 | 8/2003 |
| WO | WO 02/29117 A3 | 8/2003 |
| WO | WO 02/072772 A3 | 9/2003 |
| WO | WO 03/078645 A2 | 9/2003 |
| WO | WO 03/078645 A3 | 9/2003 |
| WO | WO 03/083435 A2 | 10/2003 |
| WO | WO 03/083435 A3 | 10/2003 |
| WO | WO 2004/011665 A2 | 2/2004 |
| WO | WO 02/48402 A3 | 4/2004 |
| WO | WO 2004/069849 A3 | 4/2004 |
| WO | WO 2004/069849 A2 | 8/2004 |
| WO | WO 2004/092418 A2 | 10/2004 |
| WO | WO 2004/092418 A3 | 12/2004 |
| WO | WO 2004/069849 A3 | 3/2005 |
| WO | WO 2004/011665 A3 | 7/2005 |
| WO | WO 2005/065321 A2 | 7/2005 |
| WO | WO 2006/138257 A2 | 3/2006 |
| WO | WO 2007/030759 A2 | 3/2007 |
| WO | WO 2007/041201 A2 | 4/2007 |
| WO | WO 2007/030759 A3 | 6/2007 |
| WO | WO 2007/041201 A3 | 11/2007 |
| WO | WO 2007/136717 A1 | 11/2007 |
| WO | WO 2008/005459 A2 | 1/2008 |
| WO | WO 2008/005459 A3 | 2/2008 |
| WO | WO 2006/138257 A3 | 12/2008 |

OTHER PUBLICATIONS

U.S. Appl. No. 60/381,457, filed May 17, 2002, Kurn.
U.S. Appl. No. 60/533,381, filed Dec. 29, 2003, Kurn et al.
Abravaya et al. Detection of point mutations with a modified ligase chain reaction (Gap-LCR). Nucleic Acids Research. 1995;23(4):675-682.
Adessi et al. Solid phase DNA amplification: characterisation of primer attachment and amplification mechanisms. Nucleic Acids Research. 2000;28(20):E87.
Agrawal et al. Site Specific Functionalization of Oligonucleotides for Attaching Two Different Reporter Groups. Nucleic Acids Research. 1990;18(18):5419-5423.
Akhras et al. Connector inversion probe technology: a powerful one-primer multiplex DNA amplification system for numerous scientific applications. PLoS ONE. 2007;2(9):e915.

Arashi-Heese et al. XcmI site-containing vector for direct cloning and in vitro transcription of PCR product. Molecular Biotechnology. 1999;12(3):281-3.

Ausubel et al. (eds.) Current Protocols in Molecular Biology. John Wiley & Sons, Inc.; 1995:iii-xii (Table of Contents Only.).

Baner et al. Parallel gene analysis with allele-specific padlock probes and tag microarrays. Nucleic Acids Research. 2003;31(17):e103.

Barbas III et al. In Vitro Evolution of a Neutralizing Human Antibody to Human Immunodeficiency Virus Type I to Enhance Affinity and Broaden Strain Cross-Reactivity. Proc. Natl. Acad. Sci. USA. 1994;91:3809-3813.

Barker et al. Increased DNA microassay hybridization specificity using sscDNA targets. BMC Genomics. 2005;6(1):57.

Barth et al. Combining Phage Display and Screening of cDNA Expression Libraries: A New Approach for Identifying the Target Antigen of an scFv Preselected by Phage Display. Journal of Molecular Biology. 2000;301:751-757.

Beaucage et al. Deoxynucleotide Phosphoramidites-A New Class of Key Intermediates for Deoxypolynucleotide Synthesis. Tetrahedron Letters. 1981;22(20):1859-1862.

Beggs, et al. Characterization of Myocobacterium tuberculosis complex direct repeat sequence for use in cycling probe reaction. J Clin Microbiol. Dec. 1996;34(12):2985-9.

Bekkaoui et al. Rapid detection of the mecA gene in methicillin resistant staphylococci using a colorimetric cycling probe technology. Diagnostic Microbiology and Infectious Disease. 1999;34(2):83-90.

Ben-Artzi, et al. Double-stranded RNA-dependent RNase activity associated with human immunodeficiency virus type 1 reverse transcriptase. Proc Natl Acad Sci U S A. Feb. 1, 1992;89(3):927-31.

Blanchard et al. High-density oligonucleotide arrays. Biosensors & Bioelectronics. 1996;11(6/7):687-690.

Brenner et al. Gene expression analysis by massively parallel signature sequencing (MPSS) on microbead arrays. Nature Biotechnology. 2000:18(6):630-634.

Brown et al. Chemical Synthesis and Cloning of a Tyrosine tRNA Gene. Methods In Enzymology. 1979;68:109-151.

Brown, T.A. Ed. Molecular Biology, LabFax. Bios Scientific Publishers. Academic Press. 1991; pp. 147-148.

Caruthers et al. Chemical synthesis of deoxyoligonucleotides by the phosphoramidite method. Methods In Enzymology. 1987;154:287-313.

Chetverin et al. On the nature spontaneous RNA synthesis by Q beta replicase. Journal of Molecular Biology. 1991;222(1):3-9.

Church. Genomes for ALL. Scientific American. 2006;294(1):46-54.

Coco et al. DNA Shuffling Method for Generating Highly Recombined Genes and Evolved Enzymes. Nature Biotechnology. 2001;19:354-359.

Cohen et al. Construction of biologically functional bacterial plasmids in vitro. Proc. Natl. Acad. Sci. USA. 1973;70(11):3240-4.

Coljee et al. Seamless Gene Engineering Using RNA- and DNA-Overhang Cloning. Nature Biotechnology. 2000;18:789-791.

Crameri et al. Molecular Evolution of an Arsenate Detoxification Pathway by DNA Shuffling. Nature Biotechnology. 1997;15:436-438.

Dafforn et al. Linear mRNA amplification from as little as 5 ng total RNA for global gene expression analysis. Biotechniques. 2004;37(5):854-857.

Dahl et al. Multigene amplification and massively parallel sequencing for cancer mutation discovery. Proc. Natl. Acad. Sci. USA. 2007;104(22):9387-9392.

Daigo et al. Degenerate Oligonucleotide Primed-Polymerase Chain Reaction-Based Array Comparative Genomic Hybridization for Extensive Amplicon Profiling of Breast Cancers. American Journal of Pathology. 2001;158(5):1623-1631.

Database WPI, Section Ch, Week 199507, Derwent Publications Ltd., London, GB; Class B04, AN 1995-047919, XP002276586 & JP 06 327500 A (Toyobo KK), Nov. 29, 1994. (Abstract Only). 1 page total.

Dean et al. Comprehensive Human Genome Amplification Using Multiple Displacement Amplification. Proc. Natl. Acad. Sci. USA. 2002;99(8):5261-5266.

Derisi et al. Use of cDNA microarray to analyse gene expression patterns in human cancer. Nature Genetics. 1996;14:457-460.

Dietmaier et al. Multiple Mutation Analyses in Single Tumor Cells with Improved Whole Genome Amplification. American Journal of Pathology. 1999;154(1):83-95.

Dressman et al. Transforming single DNA molecules into fluorescent magnetic particles for detection and enumeration of genetic variations. Proc. Natl. Acad. Sci. USA. 2003:100(15):8817-8822.

European Search Report (Supplementary partial) mailed Dec. 22, 2005 for European Patent Application No. 02731119.0.

European search report dated Mar. 13, 2006 for Application No. 02731119.

European search report dated Sep. 17, 2009 for Application No. 04002084.4.

European search report dated Nov. 13, 2006 for Application No. 03717952.

European Search Report mailed on May 13, 2004 for patent application No. 02721342.0-2402.

Fan et al. Highly parallel genomic assays. Nature Reviews Genetics. 2006;7(8):632-644.

Flanagan et al. A Cytosine Analog That Confers Enhanced Potency to Antisense Oligonucleotides. Proc. Natl. Acad. Sci. USA. 1999;96(7):3513-3518.

Fodor et al. Light-Directed, spatially addressable parallel chemical synthesis. Science. 1991;251:767-773.

Freier et al. Improved Free-Energy Parameters for Predictions of RNA Duplex Stability. Proc. Natl. Acad. Sci. USA. 1986;83:9373-9377.

Freshney. ed. Animal Cell Culture. IRL Press: Oxford; 1987: vii-xii (Table of Contents Only.).

Fu et al. Sequencing Double-Stranded DNA by Strand Displacement. Nucleic Acids Research. 1997;25(3):677-679.

Gait. Oligonucleotide Synthesis: A Practical Approach. ed. IRL Press: Oxford; 1984:vii-xii (Table of Contents).

Gasparini et al. Scanning the First Part of the Neurofibromatosis Type 1 Gene by RNA-SSCP: Identification of Three Novel Mutations and of Two New Polymorphisms. Human Genetics. 1996;97:492-495.

Ghadessy et al. Directed evolution of polymerase function by compartmentalized self-replication. Proc. Natl. Acad. Sci. USA. 2001;98(8):4552-4557.

GO. Protein Structures and Split Genes. Advances in Biophysics. 1985;19:91-131.

Goodchild. Conjugates of Oligonucleotides and Modified Oligonucleotides: A Review of Their Synthesis and Properties. Bioconjugate Chemistry. 1990;1(3):165-187.

Guatelli et al. Isothermal, In Vitro Amplification of Nucleic Acids by a Multienzyme Reaction Modeled After Retroviral Replication. Proc. Natl. Acad. Sci. USA. 1990;87:1874-1878.

Gubler et al. A simple and very efficient method for generating cDNA libraries. Gene. 1983;25:263-269.

Gulick et al. Forced Evolution of Glutathione S-Transferase to Create a More Efficient Drug Detoxication Enzyme. Proc. Natl. Acad. Sci. USA. 1995;92:8140-8144.

Habermann et al. Clostridial Neurotoxins: Handling and Action at the Cellular and Molecular Level. Current Topics in Microbiology and Immunology. 1986;129:93-179.

Heim et al. Engineering Green Fluorescent Protein for Improved Brightness, Longer Wavelengths and Fluorescence Resonance Energy Transfer. Current Biology. 1996;6:178-182.

Hendrickson et al. High sensitivity multianalyte immunoassay using covalent DNA-labeled antibodies and polymerase chain reaction. Nucleic Acids Research. 1995;23:522-529.

Hottiger, et al. Strand displacement activity of the human immunodeficiency virus type 1 reverse transcriptase heterodimer and its individual subunits. J Biol Chem. Jan. 14, 1994;269(2):986-91.

Huber, et al. Processing of the primer for plus strand DNA synthesis by human immunodeficiency virus 1 reverse transcriptase. J Biol Chem. Jun. 25, 1990;265(18):10565-73.

Hutchison et al. Cell-free cloning using phi29 DNA polymerase. Proc. Natl. Acad. Sci. USA. 2005;102(48):17332-17336.

Innis et al. PCR Protocols: A Guide to Methods and Applications. Eds. Academic Press. 1990:v-x (Table of Contents).

International search report dated Feb. 3, 2003 for PCT Application No. US2001/047775.
International search report dated Mar. 9, 2007 for PCT Application No. US2006/035154.
International search report dated Mar. 18, 2003 for PCT Application No. US01/20660.
International search report dated Jun. 23, 2003 for PCT Application No. US02/07306.
International search report dated Jul. 3, 2001 for PCT Application No. US00/25104.
International search report dated Sep. 28, 2009 for PCT Application No. US2009/033964.
International search report dated Oct. 20, 2009 for PCT Application No. US2009/037870.
International Search Report mailed Aug. 8, 2003 for PCT Application No. PCT/US02/07377.
International Search Report mailed on Jan. 8, 2004, for PCT patent application No. PCT/US03/07425 filed on Mar. 11, 2003.
International Search Report mailed on Oct. 15, 2004 for PCT Application No. PCT/US2004/012779 filed on Apr. 14, 2004.
International Search Report mailed on Oct. 30, 2003, for PCT patent application No. PCT/US03/10148 filed on Mar. 31, 2003.
Joyce. Directed Molecular Evolution. Scientific American. 1992;267(6):90-97.
Kass et al. Inter-alu polymerase chain reaction: advancements and applications. Analytical Biochemistry. 1955;228(2):185-193.
Khrapko et al. A method for DNA sequencing by hybridization with oligonucleotide matrix. DNA Sequence. 1991;1:375-388.
Kikuchi et al. An Effective Family Shuffling Method Using Single-Stranded DNA. Gene. 2000;243:133-137.
Kikuchi et al. Novel Family Shuffling Methods for the in vitro Evolution of Enzymes. Gene. 1999;236:159-167.
Kojima et al. PCR amplification from single DNA molecules on magnetic beads in emulsion: application for high-throughput screening of transcription factor targets. Nucleic Acids Research. 2005;33(17):e150.
Kolkman et al. Directed Evolution of Proteins by Exon Shuffling. Nature Biotechology. 2001;19:423-428.
Kricka. Nonisotopic DNA Probe Techniques. Academic Press. 1992. (Table of Contents only).
Kumar et al. The First Analogues of LNA (Locked Nucleic Acids): Phosphorothioate LNA and 2'-Thio-LNA. Bioorganic & Medicinal Chemistry Letters. 1998;8:2219-2222.
Kurn et al. Novel isothermal, linear nucleic acid amplification systems for highly multiplexed applications. Clinical Chemistry. 2005;51(10):1973-1981.
Kurtzman et al. Advances in Directed Protein Evolution by Recursive Genetic Recombination: Applications to Therapeutic Proteins. Current Opinion in Biotechnology. 2001;12:361-370.
Kwoh et al. Transcription-Based Amplification System and Detection of Amplified Human Immunodeficiency Virus Type 1 with a Bead-Based Sandwich Hybridization Format. Proc. Natl. Acad. Sci. USA. 1989;86:1173-1177.
Li et al. Amplification and analysis of DNA sequences in single human sperm and diploid cells. Nature. 1988;335(6189):414-417.
Lishanski et al. Branch Migration Inhibition in PCR-Amplified DNA: Homogeneous Mutation Detection. Nucleic Acids Research. 2000;28(9):E42, pp. i-vii.
Lizardi et al. Mutation detection and single-molecule counting using isothermal rolling-circle amplification. Nature Genetics. 1998;19(3):225-232.
Lockhart et al. Expression monitoring by hybridization to high-density oligonucleotide arrays. Nature Biotechnology. 1996;14:1675-1680.
Macmillan et al. Synthesis of Functionally Tethered Oligodeoxynucleotides by the Convertible Nucleoside Approach. The Journal of Organic Chemistry. 1990;55:5931-5933.
Makos et al. Oligonucleotide Hybridisations on Glass Supports: A Novel Linker for Oligonucleotide Synthesis and Hybridisation Properties of Oligonucleotides Synthesised in situ. Nucleic Acids Research. 1992;20(7):1679-1684.

Marcy et al. Nanoliter reactors improve multiple displacement amplification of genomes from single cells. PLoS Genetics. 2007;3(9):1702-1708.
Marshall et al. DNA chips: An array of possibilities. Nature Biotechnology. 1998;16:27-31.
Maskos et al. Oligonucleotide hybridisations on glass supports: a novel linker for oligonucleotide synthesis and hybridisation properties of oligonucleotides synthesised in situ. Nucleic Acids Research. 1992;20(7):1679-1684.
Matson et al. Biopolymer synthesis on polypropylene supports: Oligonucleotide arrays. Analytical Biochemistry. 1995;224(1):110-116.
Medical Dictionary, online, definition of RNase I, pp. 1-3, retrieved 2009, from: http://www.mondofacto.com/facts/dictionary?Escherichia+coli+RNase+I.
Mitra et al. In situ localized amplification and contact replication of many individual DNA molecules. Nucleic Acids Research. 1999;27(24):e34.
Mullis et al. PCR: Polvmerase Chain Reaction. eds. Birkhauser: Boston; 1994:xv-xvii (Table of Contents).
Mullis et al. Specific Enzymatic Amplification of DNA In Vitro: the Polymerase Chain Reaction. Cold Spring Harbor Symposia on Quantitative Biology. 1986;51:263-273.
Mullis et al. Specific synthesis of DNA in vitro via a polymerase-catalyzed chain reaction. Methods in Enzymology. 1987;155:335-350.
Nakano et al. Single-molecule PCR using water-in-oil emulsion. Journal of Biotechnology. 2003;102(2):117-24.
Narang et al. Improved Phosphotriester Method for the Synthesis of Gene Fragments. Methods of Enzymology. 1979;68:90-99.
New England Biolab Polymerases. Polymerases from NEB. 2008;p. 1-2. Available at http://www.neb.com/nebecomm/tech_reference/polymerases/polymerases_from_neb.as p. Accessed Jun. 30, 2008.
Nugen, Inc. Ovation Biotin RNA Amplification and Labeling System User Guide. Catalog #2300-12. Published 2004.
Nugen, Inc. Technical Report #1. The Ovation Biotin System Validation for Use with Affymetrix GeneChip Arrays. Published 2004.
Okayama et al. High Efficiency Cloning of Full-Length cDNA. Molecular and Cell Biology. 1982;2:161-170.
Orita et al. Detection of Polymorphisms of Human DNA by Gel Electrophoresis as Single-Strand Conformation Polymorphisms. Proc. Natl. Acad. Sci. USA. 1989;86(8):2766-2770.
Orita et al. Rapid and sensitive detection of point mutations and DNA polymorphisms using the polymerase chain reaction. Genomics. 1989;5(4):874-879.
Patel et al. Formation of chimeric DNA primer extension products by template switching onto an annealed downstream oligonucleotide. Proc. Natl. Acad. Sci. USA. 1996;93:2969-2974.
Pease et al. Light-generated oligonucleotide arrays for rapid DNA sequence analysis. Proc. Natl. Acad. Sci. USA Biochemistry. 1994;91:5022-5026.
Pieles et al. Preparation of a Novel Psoralen Containing Deoxyadenosine Building Block for the Facile Solid Phase Synthesis of Psoralen-Modified Oligonucleotides for a Sequence Specific Crosslink to a Given Target Sequence. Nucleic Acids Research. 1989;17(22):8967-8978.
Pluckthun et al. In Vitro Selection and Evolution of Proteins. Advances in Protein Chemistry. 2001;55:367-403.
Ramsay. DNA chips: State-of-the art. Nature Biotechnology. 1998;16:40-44.
Roget et al. Synthesis and Use of Labelled Nucleoside Phosphoramidite Building Blocks Bearing a Reporter Group: Biotinyl, Dinitrophenyl, Pyrenyl and Dansyl. Nucleic Acids Research. 1989;17:7643-7651.
Saiki et al. Primer-directed enzymatic amplification of DNA with a thermostable DNA polymerase. Science. 1988;239:487-491.
Sambrook et al. (eds.), Molecular Cloning—A Laboratory Manual, 1989, Second Edition, Cold Spring Harbor Laboratory Press, Cold Spring Harbor, New York, pp. xi-xxxviii (Table of Contents Only.).
Sano et al. Immuno-PCR: very sensitive antigen detection by means of specific antibody-DNA conjugates. Science. 1992;258:120-122.

Sarkar et al. Screening for Mutations by RNA Single-Strand Conformation Polymorphism (rSSCP): Comparison with DNA-SSCP. Nucleic Acids Research. 1992;20(4):871-878.

Sasaki et al. Transcriptional sequencing: A method for DNA sequencing using RNA polymerase. Biochemistry. 1998;95:3455-3460.

Scaringe et al. Novel RNA synthesis method using 5'-0-silyl-2'-0-orthoesther protecting groups. Journal of American Chemical Society. 1998;120:11820-11821.

Scaringe. Advanced 5'-SilyI-2'-Orthoesther Approach to RNA Oligonucleotide Synthesis. Methods Enzymology. 2000;317:3-18.

Schena et al. Parallel Human Genome Analysis: Microarray-Based Expression Monitoring of 1000 Genes. Proc. Natl. Acad. Sci. USA. 1996;93:10614-10619.

Schena et al. Quantitative monitoring of gene expression patterns with a complementary DNA microarray. Science. 1995;270:467-470.

Schmidt-Dannert. Directed Evolution of Single Proteins, Metabolic Pathways, and Viruses. Biochemistry. 2001;40(44):13125-13136.

Schweitzer et al. Immunoassays with rolling circle DNA amplification: a versatile platform for ultrasensitive antigen dectection. Proc. Natl. Acad. Sci. USA. 2000;97(18):10113-10119.

Scott et al. Production of Cyclic Peptides and Proteins in vivo. Proc. Natl. Acad. Sci. USA. 1999;96(24):13638-13643.

Shalon et al. A DNA microarray system for analyzing complex DNA samples using two-color fluorescent probe hybridization. Genome Research. 1996;6:639-645.

Shendure et al. Accurate multiplex polony sequencing of an evolved bacterial genome. Science. 2005;309(5741):1728-32.

Stemmer. DNA Shuffling by Random Fragmentation and Reassembly: In Vitro Recombination for Molecular Evolution. Proc. Natl. Acad. Sci. USA. 1994;91:10747-10751.

Stemmer. Rapid Evolution of a Protein In Vitro by DNA Shuffling. Nature. 1994;370:389-391.

Stoecklein et al. SCOMP Is Superior to Degenerated Oligonucleotide Primed Polymerase Chain Reaction for Global Amplification of Minute Amounts of DNA From Microdissected Archival Tissue Samples. American Journal of Pathology. 2002;161(1):43-51.

Stump et al. The Use of Modified Primers to Eliminate Cycle Sequencing Artifacts. Nucleic Acids Research. 1999;27(23):4642-4648.

Suzuki, et al. Detection of ras Gene Mutations in Human Lung Cancers by Single Strand Conformation Polymorphism Analysis of Polymerase Chain Reaction Products. Oncogene. 1990;5(7):1037-1043.

Tesler et al. Synthesis and Characterization of DNA Oligomers and Duplexes Containing Covalently attached Molecular Labels: Comparison of Biotin, Fluorescein, and Pyrene Labels by Thermodynamic and Optical Spectroscopic Measurements. Journal of the American Chemical Society. 1989;111:6966-6976.

Tijessen. Hybridization with Nucleic Acid Probes. Elsevier Science Publishers. 1993. (Table of Contents).

Tinoco et al. Improved Estimation of Secondary Structure in Ribonucleic Acids. Nature New Biology. 1973;246:40-41.

Traut. Are Proteins Made of Modules? Molecular and Cellular Biochemistry. 1986;70:3-10.

Vogelstein et al. Digital PCR. Proc. Natl. Acad. Sci. USA. 1999;96(16):9236-41.

Volkov et al. Recombination and Chimeragenesis by in vitro Heteroduplex Formation and in vivo Repair. Nucleic Acids Research. 1999;27(18):e18i-e18vi.

Wadenback et al. Comparison of standard exponential and linear techniques to amplify small cDNA samples for microarrays. BMC Genomics. 2005;6(1):61.

Wahlestedt et al. Potent and nontoxic antisense oligonucleotides containing locked nucleic acids. Proc. Natl. Acad. Sci. USA. 2000;97(10):5633-5638.

Walker et al. Isothermal In Vitro Amplification of DNA by a Restriction Enzyme/DNA Polymerase System. Proc. Natl. Acad. Sci. USA. Applied Biological Sciences. 1992;89:392-396.

Walker et al. Strand displacement amplification—an isothermal, in vitro DNA amplification technique. Nucleic Acids Research 1992;20(7):1691-1696.

Wang et al. Whole genome amplification and high-throughput allelotyping identified five distinct deletion regions on chromosomes 5 and 6 in microdissected early-stage ovarian tumors. Cancer Research. 2001;61:4169-4174.

Wang et al. High-fidelity mRNA amplification for gene profiling. Nature Biotechnology. 2000;18: 457-459.

Wiltshire et al. Detection of Multiple Allergen-Specific IgEs on Microarrays by Immunoassay with Rolling Circle Amplification. Clinical Chemistry. 2000;46(12):1990-1993.

Wu et al. Detection of *Clostridium botulinum* neurotoxin type a using immuno-PCR. Letters in Applied Microbiology. 2001;32:321-325.
Wu et al. The Ligation Amplification Reaction (LAR)-Amplification of Specific DNA Sequences Using Sequential Rounds of Template-Dependent Ligation. Genomics. 1989;4:560-569.
You et al. Directed Evolution of Subtilisin E in *Bacillus subtilis* to Enhance Total Activity in Aqueous Dimethylformamide. Protein Engineering. 1994;9(1):77-83.
Zhang et al. Directed Evolution of a Fucosidase From a Galactosidase by DNA Shuffling and Screening. Proc. Natl. Acad. Sci. USA. 1997;94:4504-4509.
Zhang et al. Protein quantification from complex protein mixtures using a proteomics methodology with single-cell resolution. Proc. Natl. Acad. Sci. USA. 2001;98(10):5497-5502.
Zheng et al. Whole Genome Amplification Increases the Efficiency and Validity of Buccal Cell Genotyping in Pediatric Populations. Cancer Epidemiology. 2001;10:697-700.
European search report dated Nov. 11, 2008 for Application No. 3718172.4.
Inoue, et al. Synthesis and hybridization studies on two complementary nona(2'-O-methyl)ribonucleotides. Nucleic Acids Res. Aug. 11, 1987;15(15):6131-48.
Miyachi, et al. Application of chimeric RNA-DNA oligonucleotides to the detection of pathogenic microorganisms using surface plasmon resonance. Analytica Chimica Acta. 2000; 407(1):1-10.
Stratagene Catalog. 1988;p. 39. Gene Characterization Kits. Table of Contents.
Wang, et al. Relative stabilities of triple helices composed of combinations of DNA, RNA and 2'-O-methyl-RNA backbones: chimeric circular oligonucleotides as probes. Nucleic Acids Res. Apr. 11, 1995;23(7):1157-64.
Bing, et al. Bridge Amplification: A Solid Phase PCR System for the Amplification and Detection of Allelic Differences in Single Copy Genes. Genetic Identity Conference Proceedings. 1996. Available at http://www.promega.com/geneticidproc/ussymp7proc/0726.html. Accessed Dec. 22, 2009.
Hatch, et al. Rolling circle amplification of DNA immobilized on solid surfaces and its application to multiplex mutation detection. Genet Anal. Apr. 1999;15(2):35-40.
International search report dated Nov. 20, 2009 for PCT Application No. US2009/33936.
Westin, et al. Anchored multiplex amplification on a microelectric chip array. Nat Biotechnol. Feb. 2000;18(2):199-204.

* cited by examiner

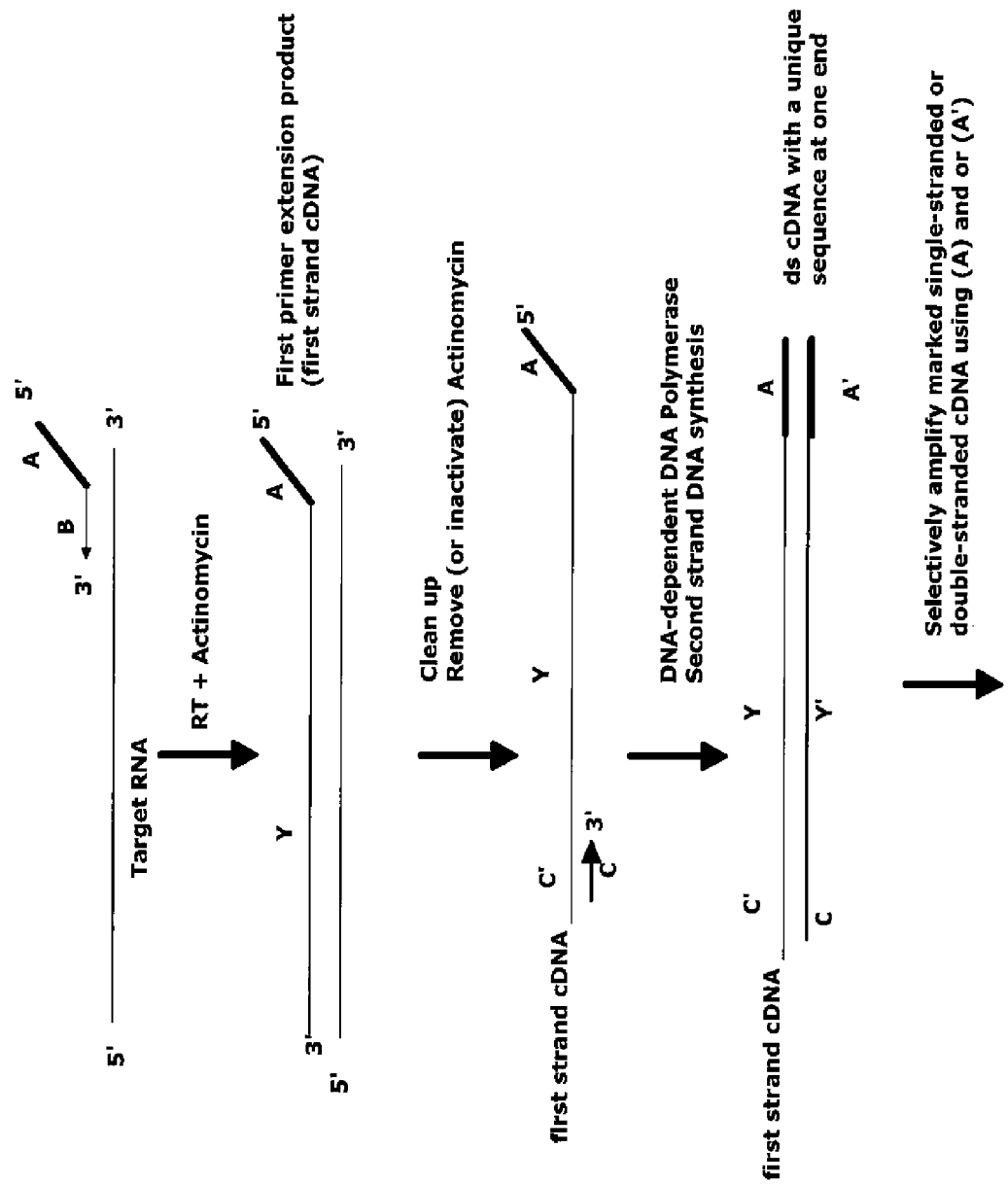

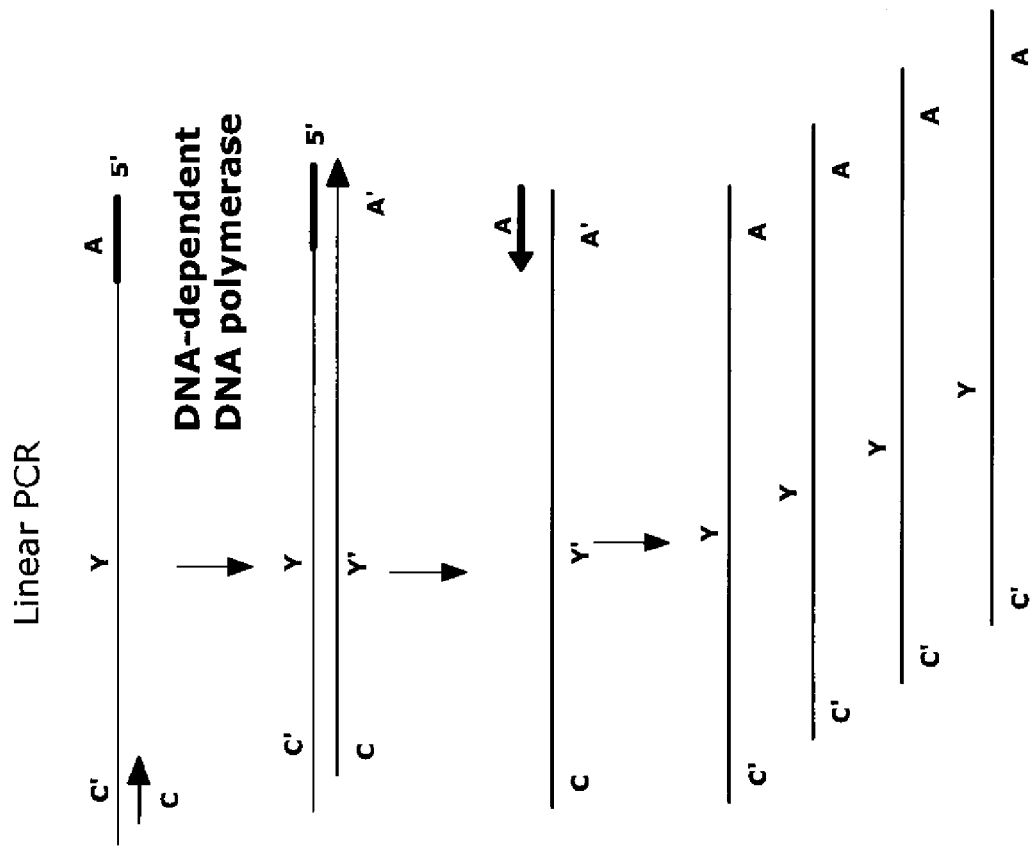

METHODS OF RNA AMPLIFICATION IN THE PRESENCE OF DNA

CROSS-REFERENCE

This application claims the benefit of U.S. Provisional Application Nos. 61/038,696, filed Mar. 21, 2008; 61/074,991, filed Jun. 23, 2008; and 61/085,811, filed Aug. 1, 2008, which applications are incorporated herein by reference in their entirety. This application is related to the following co-pending international patent applications PCT/US2009/033936 and PCT/US2009/033964 filed Feb. 12, 2009, which claim the benefit of the foregoing provisional applications and U.S. Provisional Application No. 61/028,146; filed Feb. 12, 2008; and which applications are all incorporated herein by reference in their entirety.

BACKGROUND OF THE INVENTION

The detection and/or quantitation of specific nucleic acid sequences is an important technique for identifying and classifying microorganisms, diagnosing infectious diseases, detecting and characterizing genetic abnormalities, identifying genetic changes associated with cancer, studying genetic susceptibility to disease, and measuring response to various types of treatment. Such procedures are also useful in detecting and quantitating microorganisms in foodstuffs, water, industrial and environmental samples, seed stocks, and other types of material where the presence of specific microorganisms may need to be monitored. Other applications are found in the forensic sciences, anthropology, archaeology, and biology where measurement of the relatedness of nucleic acid sequences has been used to identify criminal suspects, resolve paternity disputes, construct genealogical and phylogenetic trees, and aid in classifying a variety of life forms.

The ability to amplify ribonucleic acid (RNA) is an important aspect of efforts to elucidate biological processes. Amplification of the total cellular mRNAs prepared from any cell or tissue is important for gene expression profiling. Total cellular mRNA represents gene expression activity at a defined time. Gene expression is affected by cell cycle progression, developmental regulation, response to internal and external stimuli and the like. The profile of expressed genes for any cell type in an organism reflects normal or disease states, response to various stimuli, developmental stages, cell differentiation, and the like. Non-coding RNAs have been shown to be of great importance in regulation of various cellular functions and in certain disease pathologies. Such RNAs are often present in very low levels. Although analysis of non-amplified mRNA is feasible, a significant amount of starting mRNA can be required. Thus, amplification methods capable of amplifying low abundance RNAs, are of great importance.

RNA amplification is commonly performed using the reverse transcriptase-polymerase chain reaction (RT-PCR) method and variations thereof. These methods are based on replication of RNA by reverse transcriptase to form single stranded DNA complementary to the RNA (cDNA), which is followed by amplification techniques such as polymerase chain reaction (PCR) or linear isothermal amplification to produce multiple copies of single or double stranded DNA, or RNA. However, the total amount of sample RNA that is available is frequently limited by the amount of biological sample from which it is derived. Biological samples are often limited in amount and precious. Moreover, the amount of the various RNA species is not equal; some species are more abundant than others are, and these are more likely and easier, to analyze. The ability to amplify RNA sequences enables the analysis of less abundant, rare RNA species. The ability to analyze small samples, by means of nucleic acid amplification, is also advantageous for design parameters of large scale screening of effector molecule libraries, for which reduction in sample volume is a major concern both for the ability to perform very large scale screening or ultra high throughput screening, and in view of the limiting amounts of library components. Methods of amplification from RNA templates have been described, for example in U.S. Pat. No. 6,946,251.

RNA in biological samples is often in the presence of DNA. Amplification of the target RNA in the presence of DNA results in unwanted amplification products as described herein. It is desirable to prevent these unwanted products that originate from initiation on DNA because they may interfere with analysis of target RNA amplification products, result in erroneous conclusions and affect the amplification yield from the target RNA. Purification of RNA from DNA results in reduced yield and/or RNA quality. Therefore, it is highly desirable to develop improved amplification methods of target RNA in the presence of DNA. Moreover, the ability to selectively amplify RNA in a sample comprising total nucleic acid from a biological sample will also assist in the development of procedures and methods for selective amplification in situ as well as directly from stabilized cell lysates. This is especially useful when there are minute amounts of sample for analysis.

Therefore, there is a need for improved RNA amplification methods that overcome drawbacks in existing methods. The invention provided herein fulfills this need and provides additional benefits.

All references cited herein, including patent applications and publications, are incorporated by reference in their entirety.

SUMMARY OF THE INVENTION

One aspect of the invention comprises a method of generating multiple copies of a polynucleotide sequence of or complementary to target RNA which is in a sample comprising DNA, said method comprising the steps of: (a) hybridizing to the target RNA a first primer comprising a sequence (A) that is not complementary to the target RNA, and a sequence (B) at the 3'-end which hybridizes to the target RNA; (b) extending the first primer with at least one enzyme comprising RNA-dependent DNA polymerase activity in the presence of at least one compound comprising DNA-dependent DNA polymerase inhibitor activity, whereby a complex comprising a primer extension product and the target RNA is produced, whereby the first primer extension product comprises a sequence (Y) that is complementary to the target RNA and comprises sequence (A). In one embodiment of this aspect of the invention, the first primer extension product is marked or labeled with the sequence (A) by the use of the first primer comprising the sequence (A). The method further comprises the steps of: (c) disabling or removing at least one compound comprising DNA-dependent DNA polymerase inhibitor activity; and (d) producing multiple copies of a polynucleotide sequence complementary to the target RNA and/or complementary to sequence (Y) using sequence (A). In one embodiment of this aspect of the invention, the method selectively generates multiple copies of the target RNA polynucleotide sequence of interest in the presence of non-target DNA and/or RNA. In some embodiments, the method is suitable for amplifying one or more whole transcriptomes or a substantial fraction thereof in the presence of DNA. In one embodiment of this aspect of the invention, the method generates amplified polynucleotides suitable for downstream analysis by sequencing, expression profiling, Q-PCR, digital PCR, serial analysis of gene expression (SAGE), RFLP analysis, SNP detection or massively parallel analytical methods including for example massively parallel sequencing, massively parallel expression profiling, microarray analysis, high density PCR arrays, pyrosequencing, sequencing by synthesis, sequencing by ligation, sequencing by hybridization, single molecule sequencing, nanopore sequencing, or massarray analysis. In one embodiment of this aspect of the invention, the method generates amplified polynucleotides in a clonal fashion on a bead, in an emulsion, or as polonies.

One aspect of the invention comprises a method of generating multiple copies of a polynucleotide sequence complementary to a target RNA which is in a sample comprising DNA, said method comprising the steps of: (a) hybridizing to the target RNA a first primer comprising a sequence (A) that does not hybridize to the target RNA, and a sequence (B) at the 3'-end, which hybridizes to the target RNA; (b) extending the first primer with at least one enzyme comprising RNA-dependent DNA polymerase activity in the presence of at least one compound comprising DNA-dependent DNA polymerase inhibitor activity, whereby a complex comprising a first primer extension product and the target RNA is produced, whereby the first primer extension product comprises a sequence (Y) that is complementary to the target RNA and comprises sequence (A). In one embodiment of this aspect of the invention, the first primer extension product is marked or labeled with the sequence (A) by the use of the first primer comprising the sequence (A). The method further comprises the steps of: (c) disabling or removing at least one compound comprising DNA-dependent DNA polymerase inhibitor activity; (d) cleaving the target RNA in the complex of step (b); (e) extending a second primer along the first primer extension product with at least one enzyme comprising DNA-dependent DNA polymerase activity, wherein the second primer comprises sequence (C) that is complementary to a sequence (C') on the first primer extension product to produce a complex comprising the first primer extension product and a second primer extension product, whereby the second primer extension product comprises the sequence (C), a sequence (Y') complementary to sequence (Y) and sequence (A') complementary to sequence (A); (f) producing multiple copies of a polynucleotide sequence complementary to the target RNA using a primer with a sequence (A) and/or sequence (A'). In one embodiment of this aspect of the invention, the method selectively generates multiple copies of the target RNA polynucleotide sequence of interest in the presence of non-target DNA and/or RNA. In some embodiments, the method is suitable for amplifying one or more whole transcriptomes or a substantial fraction thereof in the presence of DNA. In one embodiment of this aspect of the invention, the methods generates amplified polynucleotides suitable for downstream analysis by sequencing, expression profiling, Q-PCR, digital PCR, serial analysis of gene expression (SAGE), RFLP analysis, SNP detection or massively parallel analytical methods including for example massively parallel sequencing, massively parallel expression profiling, microarray analysis, high density PCR arrays, pyrosequencing, sequencing by synthesis, sequencing by ligation, sequencing by hybridization, single molecule sequencing, nanopore sequencing, or massarray analysis.

In some embodiments of the methods, the first primer comprises a 5' sequence that is not hybridizable to the target RNA. In some embodiments of the methods, the sequence (A') is used as a priming site for amplification.

In some embodiments of the methods, the producing of multiple copies in step (f) are produced using amplification methods comprising polymerase chain reaction (PCR). In some embodiments of the methods, a PCR primer comprises sequence (A) of the first primer. In some embodiments of the methods, a PCR primer comprises sequence (C) of the second primer. In some embodiments of the methods the producing of multiple copies in step (f) comprises performing PCR with primer pairs wherein the first PCR primer is complementary to sequence (A') and the second PCR primer is complementary to all or a portion of sequence (C') or all or a portion of sequence (Y). In some embodiments of the methods the producing of multiple copies in step (f) comprises performing single primer, linear PCR using a PCR primer complementary to sequence (A').

In some embodiments of the methods the producing of multiple copies in step (f) comprises an amplification method comprising the use of an RNA/DNA composite primer, RNase H, and a DNA dependent DNA polymerase with strand displacement activity.

In some embodiments of the methods, the first primer comprises an RNA and a DNA sequence wherein a 5'-RNA sequence comprises sequence (A) and a 3'-DNA sequence comprises sequence (B); whereby the complex formed in step (e) comprises an RNA/DNA heteroduplex at one end; and wherein the producing of multiple copies in step (f) comprises the steps of (i) cleaving the RNA from the heteroduplex, (ii) hybridizing to sequence (A') an amplification primer comprising a 5' RNA sequence and a 3' DNA sequence, (iii) extending the amplification primer with at least one enzyme comprising DNA dependent DNA polymerase activity and comprising strand displacement activity, (iv) cleaving the RNA from the extended amplification primer in the heteroduplex with at least one enzyme comprising a specificity for cleaving RNA in a DNA-RNA heteroduplex; and (v) repeating steps (ii) through (iv) to produce multiple copies of amplification product comprising sequence (Y) that is complementary to a portion of the RNA template.

In some embodiments of the methods, the producing of multiple copies in step (f) comprises in-vitro-transcription (IVT). In some embodiments of the methods, sequence (A) comprises a pro-promoter, whereby the complex formed in step (e) comprises a double stranded promoter for a DNA dependent RNA polymerase comprising sequences (A) and (A'), wherein (A) is a DNA sequence.

In some embodiments of the methods, the second primer comprises a fragment from the cleaved RNA target. In some embodiments of the methods, the fragment is generated by cleaving RNA in the complex of step (b) with an enzyme that cleaves RNA from an RNA/DNA heteroduplex, by heat, or by chemical means.

In some embodiments of the methods, the DNA-dependent DNA polymerase inhibitor activity is derived from a compound comprising at least one of the following: actinomycin, alpha-amanitin, aphidicolin, BP5, novobiocin, rifampicin, rifamycin, sulfoquinovosylmonoacylglycerol, sulfoquinovosyldiacylglycerol, ursane, oleanane triterpenoids, ursolic acid, oleanolic acid, mikanolide, dihydromikanolide, dehydroaltenusin, catapol, taxinine, cephalomanninine, dipeptide alcohols, corylifolin; bakuchiol; resveratrol; Neobavaisoflavone; daidzein; bakuchicin, levodopa, dopamine, anacardic acid and oleic acid. In some embodiments of the methods, the DNA-dependent DNA polymerase inhibitor activity is derived from a compound comprising actinomycin.

In some embodiments of the methods, the sample comprises total nucleic acid in a biological fluid. In some embodiments of the methods, the biological fluid is selected from the group consisting of: plasma, serum, urine, saliva. In some embodiments of the methods, the sample comprises viral RNA. In some embodiments of the methods, the sample comprises cell or tissue lysates. In some embodiments of the methods, the sample comprises microbial RNA in the presence or absence of additional cell or tissue components, such as a mixed population or samples suspected of the presence of infectious agent or agents.

In some embodiments of the methods, the second primer comprises a tailed primer with a 5'-sequence which does not hybridize to the first primer extension product and which comprises a propromoter sequence such that RNA transcripts are produced comprising a sequence homologous to the target RNA; whereby multiple copies of the homologous sequence of the RNA sequence of interest are generated.

In some embodiments of the methods, the producing of multiple copies in step (f) comprises hybridizing a PTO, comprising a propromoter sequence and a 3'-hybridizing region, to the 3'-end of a first primer extension product under conditions which allow transcription to occur by RNA polymerase, such that RNA transcripts are produced comprising sequences homologous to the target RNA; whereby multiple copies of the RNA sequence of interest are generated.

In some embodiments of the methods, the producing of multiple copies in step (f) comprises hybridizing a PTO, comprising a propromoter sequence and a 3'-hybridizing region, to the 3'-end of a second primer extension under conditions which allow transcription to occur by RNA polymerase, such that RNA transcripts are produced comprising sequences complementary to the target RNA; whereby multiple copies of the complementary sequence of the RNA sequence of interest are generated.

In some embodiments of the methods, the target RNA is mRNA. In some embodiments of the methods, the first primer comprises a sequence complementary to poly-A on RNA. In some embodiments of the methods, the sequence (B) which hybridizes to the target RNA comprises a random sequence. In some embodiments of the methods, the first primer comprises a portion of the sequence complementary to poly-A on RNA and a portion comprising random sequences. In some embodiments of the methods, the first primer comprises a portion of a sequence complementary to specific sequence, or sequences, on the RNA target or targets. In some embodiments of the methods, the first primer comprises a mixture of primers comprising a portion of the sequence complementary to multiple sequences on the target RNA, and may further comprise first primers comprising a sequence complementary to the poly-A sequence, or any combination of primers described herein.

In some embodiments of the methods, the method comprises generating multiple copies of two or more different sequences of interest. In some embodiments of the methods, the method comprises at least two different first primers.

In some embodiments of the methods, the sequence (B) which hybridizes to the target RNA comprises a poly-dT sequence and the target RNA is mRNA.

In some embodiments of the methods, the enzyme that cleaves RNA is RNase H.

In some embodiments of the methods, the method comprises sequencing an RNA sequence of interest, said method comprising analyzing amplification products to determine a sequence, said amplification products produced by the methods of the invention in the presence of a mixture of NTPs and NTP analogs such that transcription is terminated upon incorporation of an NTP analog. In some embodiments of the methods, the target RNA is mRNA. In some embodiments of the methods, the methods comprise analyzing amplification products for sequence analysis using any sequencing methods including massively parallel sequencing, pyrosequencing, sequencing by synthesis, sequencing by ligation, sequencing by hybridization, single molecule sequencing, or nanopore sequencing. In some embodiments of the methods, the target RNA is mRNA, a whole transcriptome, or substantial fraction thereof, or a set of whole transcriptomes or substantial fractions thereof.

In some embodiments of the methods, the method of detecting a mutation in a target RNA, comprising analyzing sequences of amplification products for the presence of a mutation as compared to a reference polynucleotide sequence, said amplification products produced by the methods of the invention. In some embodiments of the methods, the target RNA is mRNA, a whole transcriptome, or substantial fraction thereof, or a set of whole transcriptomes or substantial fractions thereof.

In some embodiments of the methods, the method of producing a nucleic acid immobilized to a substrate comprising immobilizing amplification products on a substrate, said amplification products produced by the methods of the invention. In some embodiments of the methods, the target RNA is mRNA. In some embodiments of the methods, the substrate is a microarray. In some embodiments of the methods, the target RNA is mRNA, a whole transcriptome, or substantial fraction thereof, or a set of whole transcriptomes or substantial fractions thereof.

One aspect of the invention comprises a kit for amplifying a target RNA comprising: a tailed first primer, reverse transcriptase enzyme, a DNA-dependent DNA polymerase inhibitor, and optionally, a second primer. In some embodiments, the first tailed primer comprises a 3' random portion, and the second primer comprises a random primer. In some embodiments, the kit further comprises a composite amplification primer wherein the tailed first primer is a composite primer comprising a 3' DNA portion and a 5' RNA portion. In some embodiments, the kit further comprises instructions for the use of said kit. In some embodiments, the kit further comprises a DNA-dependent DNA polymerase. In some embodiments, the kit further comprises reagents for DNA purification. In some embodiments, the kit further comprises reagents for forming an emulsion. In some embodiments, the kit further comprises a solid substrate such as a bead or beads.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 is a diagrammatic representation of an embodiment of the invention involving the creation of a marked double-stranded cDNA from a target RNA sequence using a first primer containing a sequence portion (A) that is non-complementary to the target RNA sequence, such that the first primer extension product is created from target RNA in the presence of a DNA-dependent DNA polymerase (actinomycin). A second primer is used to generate a double-stranded cDNA product comprising a sequence complementary to the target RNA and a unique terminal sequence. The marked single stranded or double stranded cDNA are amplified in a manner such that the marked cDNA is selectively amplified.

In FIG. 4a, the first strand primer extension product is produced in the presence of a DNA-dependent DNA polymerase (actinomycin). The marked cDNA can be amplified with one primer linear PCR (4b), or with two primer exponential PCR (4c).

DETAILED DESCRIPTION OF THE INVENTION

General Description

Figure 2A:
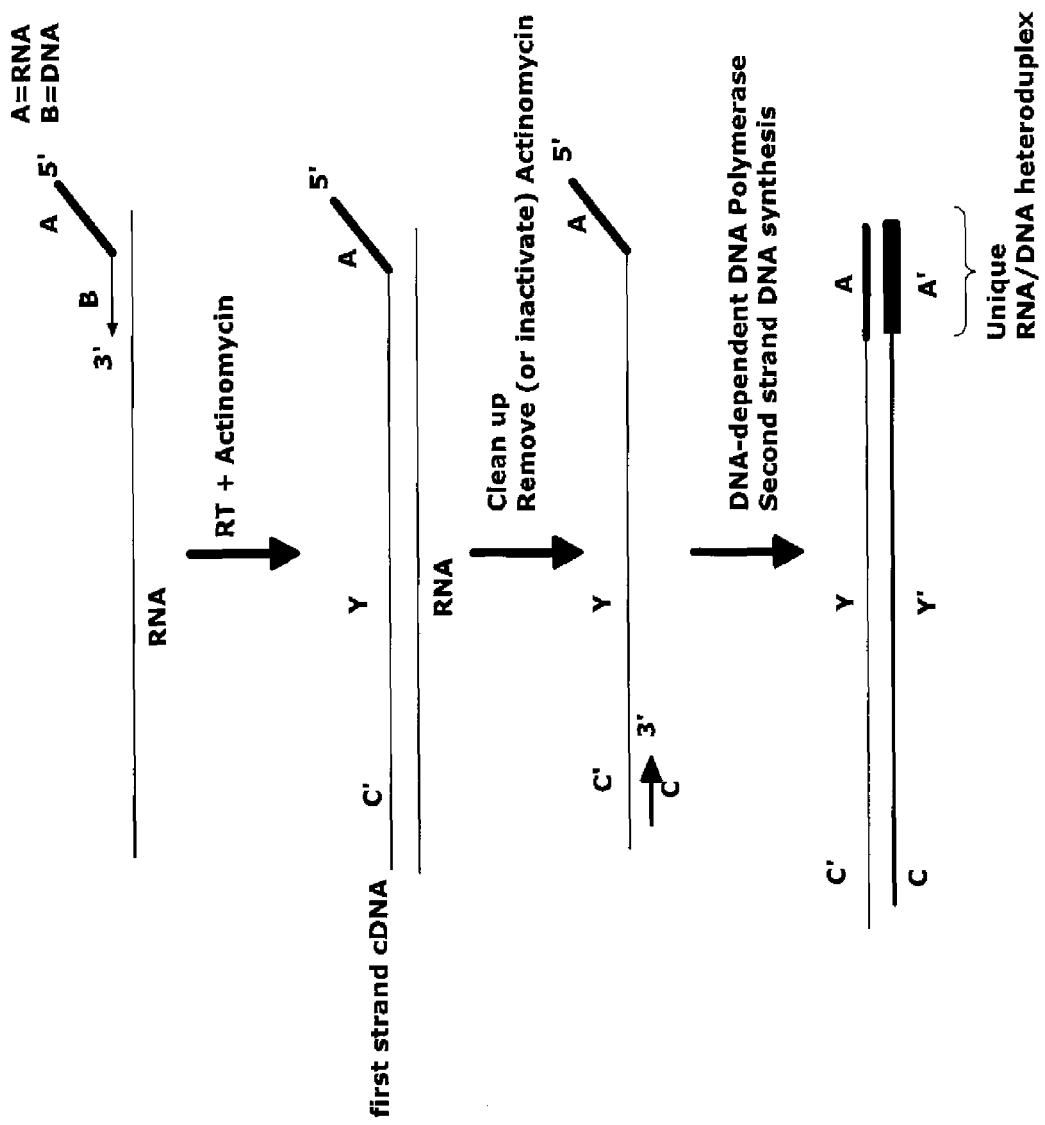
FIGS. 2a and 2b provide diagrammatic representation of an embodiment the invention in which a composite primer is used as the first primer (FIG. 2a) to produce a first primer extension product from RNA target in the presence of a DNA-dependent DNA polymerase (actinomycin); and a linear isothermal (SPIA) amplification process using a composite primer, a second primer, and strand displacement to generate multiple copies of the sequence complementary to the target RNA is used to amplify the marked cDNA (FIG. 2b).

The invention provides novel and improved methods, compositions, and kits for amplification of a target RNA sequence or polynucleotide sequence complementary to an RNA sequence of interest from samples comprising total nucleic acids (i.e. RNA and DNA molecules). The invention relates to the generation of a marked primer extension product comprising a sequence complementary to a target RNA using reverse transcriptase in the presence of a compound that inhibits DNA-dependent DNA polymerase activity, and subsequent amplification of a sequence homologous with or complementary to the target RNA using an amplification where only marked sequences are amplified.

In one aspect of the invention, the marked primer extension product is created using a tailed primer comprising a 3'-portion which is complementary to the target RNA and a 5'-portion that comprises a specific (e.g. unique or universal) sequence that is not complementary to the target RNA. In this aspect, the specific sequence acts as the marker, becoming incorporated into the sequence of the first primer extension product (e.g. first strand cDNA) at the 5'-end. During this step, the DNA dependent DNA polymerase inhibitor, e.g. actinomycin, inhibits or prevents the creation of marked first primer extension product from the DNA in the sample, thus only first primer extension product representing the RNA in the sample is produced. A second primer can then be used to form a second primer extension product (e.g. second strand cDNA) which will comprise a sequence homologous with the target RNA and will also be marked. It will be marked at its 3'-end with a sequence which comprises a sequence that is complementary to the specific sequence of the tailed primer. Generally, the DNA dependent DNA polymerase inhibitor, e.g. actinomycin, is removed or inactivated, for example by an enzyme, in order to allow the formation of second primer extension product using the first primer extension product, which is typically DNA, as template. This process creates a double stranded cDNA comprising the first primer extension product and second primer extension product wherein the primer extension products are marked at their 5' and 3'-ends respectively with specific sequences. Amplification can then be performed on these single stranded or double stranded species by amplification methods which amplify only the species containing the specific sequence. Amplification methods such as PCR, SPIA, and transcription amplification can be employed. The process described herein of marking only species with sequences related to the target RNA and amplifying only the marked species allows for the specific amplification of RNA targets in the presence of DNA without having to first isolate the target RNA or degrade the DNA in the sample, for example, by DNase treatment.

This invention relates to methods, compositions, and kits for producing multiple copies of a specific nucleic acid sequence or "target sequence" which may be present either alone or as a component, large or small, of a homogeneous or heterogeneous mixture of nucleic acids. More specifically, the target sequence is an RNA sequence. The mixture of nucleic acids may be that found in a sample taken for diagnostic testing, for screening of blood products, for food, water, industrial or environmental testing, for research studies, for the preparation of reagents or materials for other processes such as cloning, or for other purposes. The invention also relates to methods of using amplification products from a target RNA sequence, for example, for creation of cDNA libraries, for gene expression profiling, for whole transcriptome analysis, for amplification of populations of viral RNA and the like. In order that the present invention may be more readily understood, certain terms are first defined. Additional definitions are set forth throughout the detailed description.

DEFINITIONS

A "target sequence," "target nucleic acid," or "target RNA," as used herein, is a polynucleotide comprising a sequence of interest, for which amplification is desired. The target sequence may be known or not known, in terms of its actual sequence. In some instances, the terms "target," "template," and variations thereof, are used interchangeably. The target polynucleotide may be from about 10 to about 200 nucleotides in length. Alternatively, the target polynucleotide may be from about 25 to about 400 nucleotides in length. In some cases, the target polynucleotide may be from about 100 nucleotides in length to about 1 kb. In still other cases, the target polynucleotide may be 1 kb to 10 kb in length or more. In some cases, the target sequence may be from about 10 kb to 100 kb in length or more. In some cases the target polynucleotide comprises a plurality of polynucleotide sequences comprising a plurality of lengths. In some cases, the target polynucleotide comprises a plurality of polynucleotide sequences such as for example a whole transcriptome, a fraction of a whole transcriptome, or a substantial fraction of a whole transcriptome. In other cases, the plurality of target sequences may comprise a group of related sequences such as for example kinases, proteases, ion channels, transmembrane proteins, cytochrome P450 enzymes, or MHC proteins. In still other cases, the plurality of target sequences may be any group of sequences including but not limited to mRNA, a transcriptome, or set of transcriptomes. In some cases the target sequences may be viral RNA or mixtures thereof. In some cases, the target sequence(s) may be purified from a biological source such as tissue, lysates, blood, urine, hair follicle, saliva, skin, or buccal smear. In other cases, the target sequence may not be purified prior to amplification by the methods of the present invention. In some of the methods of the present invention, the target sequence is RNA and is present in a reaction mixture comprising DNA.

"Amplification," or "amplifying", as used herein, generally refers to the process of producing multiple copies of a desired sequence. "Multiple copies" mean at least 2 copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template, or a non-target sequence introduced through a primer), and/or sequence errors that occur during amplification. "Amplifying" a sequence may generally refer to making copies of a sequence or its complement, with the understanding that, as stated above, copying does not necessarily mean perfect sequence complementarity or identity with respect to the template sequence.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'--O-methyl-, 2'-O-allyl, 2'-fluoro- or 2'-azido-ribose, carbocyclic sugar analogs, .alpha.-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR2 ("amidate"), P(O)R, P(O)OR', CO or $CH_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "labeled dNTP," or "labeled rNTP," as used herein, refers, respectively, to a dNTP or rNTP, or analogs thereof, that is directly or indirectly attached with a label. For example, a "labeled" dNTP or rNTP, may be directly labeled with, for example, a dye and/or a detectable moiety, such as a member of a specific binding pair (such as biotin-avidin). A "labeled" dNTP or rNTP, may also be indirectly labeled by its attachment to, for example, a moiety to which a label is/can be attached. A dNTP or rNTP, may comprise a moiety (for example, an amine group) to which a label may be attached following incorporation of the dNTP or rNTP into an extension product. Useful labels in the present invention include fluorescent dyes (e.g., fluorescein isothiocyanate, Texas red, rhodamine, green fluorescent protein and the like), radioisotopes (e.g., $^3H$, $^{35}S$, $^{32}P$, $^{33}P$, $^{125}I$, or $^{14}C$), enzymes (e.g., LacZ, horseradish peroxidase alkaline phosphatase,), digoxigenin, and colorimetric labels such as colloidal gold or colored glass or plastic (e.g., polystyrene, polypropylene, latex, etc.) beads. Various anti-ligands and ligands can be used (as labels themselves or as a means for attaching a label). In the case of a ligand that has a natural anti-ligand, such as biotin, thyroxine and cortisol, the ligand can be used in conjunction with labeled anti-ligands.

"NTP", as used herein, generally refers to either dNTP, rNTP, or analogs thereof.

The "type" of dNTP or rNTP, as used herein, refers to the particular base of a nucleotide, namely adenine, cytosine, thymine, uridine, or guanine.

"Oligonucleotide," as used herein, generally refers to short, generally single stranded, generally synthetic polynucleotides that are generally, but not necessarily, less than about 200 nucleotides in length. The oligonucleotide(s) are generally comprised of a sequence of at least 5 or 6 nucleotides, generally from about 10 or 12 to about 100 nucleotides, about 20 to about 50 nucleotides, and often about 10 to about 30 nucleotides in length. The oligonucleotides of the invention can be DNA, RNA, DNA-RNA, or other polynucleotide and include the first primer, second primer, composite amplification primer, and propromoter polynucleotide (such as the PTO). The terms "oligonucleotide" and "polynucleotide" are not mutually exclusive. The description above for polynucleotides is equally and fully applicable to oligonucleotides.

A "primer," as used herein, refers to a nucleotide sequence, generally with a free 3'-OH group, that hybridizes with a template sequence (such as a target RNA, or a primer extension product) and is capable of promoting polymerization of a polynucleotide complementary to the template. A "primer" can be, for example, an oligonucleotide. It can also be, for example, a sequence of the template (such as a primer extension product or a fragment of the template created following RNase cleavage of a template-DNA complex) that is hybridized to a sequence in the template itself (for example, as a hairpin loop), and that is capable of promoting nucleotide polymerization. Thus, a primer can be an exogenous (e.g., added) primer or an endogenous (e.g., template fragment) primer. A primer may contain a non-hybridizing sequence that constitutes a tail on the primer. A primer may still be hybridizing even though its sequences are not completely complementary to the target.

The primers of the invention are usually oligonucleotide primers. A primer is generally an oligonucleotide that is employed in an extension by a polymerase along a polynucleotide template such as in PCR or single primer isothermal amplification for example. The oligonucleotide primer is often a synthetic polynucleotide that is single stranded, containing a sequence at its 3'-end that is capable of hybridizing with a sequence of the target polynucleotide. Normally, the 3' region of the primer that hybridizes with the target nucleic acid has at least 80%, preferably 90%; more preferably 95%, most preferably 100%, complementarity to a sequence or primer binding site. Hence, "complementary", as used herein, refers to complementary to all or a portion of a sequence. The number of nucleotides in the hybridizable sequence of a specific oligonucleotide primer should be such that stringency conditions used to hybridize the oligonucleotide primer will prevent excessive random non-specific hybridization. Usually, the number of nucleotides in the hybridizing portion of the oligonucleotide primer will be at least as great as the defined sequence on the target polynucleotide that the oligonucleotide primer hybridizes to, namely, at least six nucleotides, at least ten nucleotides, at least about 15 nucleotides and generally from about 6 to about 10 or 12 nucleotides to about 200, usually about 20 to about 50 nucleotides. In general, the target polynucleotide is larger than the oligonucleotide primer or primers as described previously. In some cases, the hybridizable sequence of an oligonucleotide primer is a random sequence. Oligonucleotide primers comprising random sequences may be referred to as random primers, as described herein. In other cases, an oligonucleotide primer such as a first primer or a second primer comprises a set of primers such as for example a set of first primers or a set of second primers. In some cases, the set of first or second primers may comprise a mixture of primers designed to hybridize to a plurality (e.g. 2, 3, 4, about 6, 8, 10, 20, 40, 80, 100, 125, 150, 200, 250, 300, 400, 500, 600, 800, 1000, 1500, 2000, 2500, 3000, 4000, 5000, 6000, 7000, 8000, 10,000, 20,000, 25,000 or more) of target sequences. In some cases, the plurality of target sequences may comprise a group of related sequences, random sequences, a whole transcriptome or fraction (e.g. substantial fraction) thereof, or any group of sequences such as mRNA.

Composite Primers are employed in certain embodiments of the invention. Composite primers are primers that are composed of RNA and DNA portions. In some aspects, the composite primer is a tailed composite primer comprising, for example, a 3'-DNA portion and a 5'-RNA portion. In the tailed composite primer, a 3'-portion, all or a portion of which comprises DNA, is complementary to a polynucleotide; and a 5'-portion, all or a portion of which comprises RNA, is not complementary to the polynucleotide and does not hybridize to the polynucleotide under conditions in which the 3'-portion of the tailed composite primer hybridizes to the polynucleotide target. When the tailed composite primer is extended with a DNA polymerase, a primer extension product with a 5'-RNA portion comprising a defined sequence can be created. This primer extension product can then have a second primer anneal to it, which can be extended with a DNA polymerase to create a double stranded product with an RNA/DNA heteroduplex comprising a defined sequence at one end. The RNA portion can be selectively cleaved from the partial heteroduplex to create a double-stranded DNA with a 3'-single-stranded overhang which can be useful for a various aspects of the present invention including allowing for isothermal amplification using a composite amplification primer.

In other aspects, the composite primer is an amplification composite primer (interchangeably called composite amplification primer). In the amplification composite primer, both the RNA and the DNA portions are generally complementary and hybridize to a sequence in the polynucleotide to be copied or amplified. In some embodiments, a 3'-portion of the amplification composite primer is DNA and a 5'-portion of the composite amplification primer is RNA. The composite amplification primer is designed such that the primer is extended from the 3'-DNA portion to create a primer extension product. The 5'-RNA portion of this primer extension product, in a RNA/DNA heteroduplex is susceptible to cleavage by RNase H, thus freeing a portion of the polynucleotide to the hybridization of an additional composite amplification primer. The extension of the amplification composite primer by a DNA polymerase with strand displacement activity releases the primer extension product from the original primer and creates another copy of the sequence of the polynucleotide. Repeated rounds of primer hybridization, primer extension with strand displacement DNA synthesis, and RNA cleavage create multiple copies of the sequence of the polynucleotide. Composite primers are described in more detail below.

A "random primer," as used herein, is a primer that generally comprises a sequence that is designed not necessarily based on a particular or specific sequence in a sample, but rather is based on a statistical expectation (or an empirical observation) that the sequence of the random primer is hybridizable (under a given set of conditions) to one or more sequences in the sample. A random primer will generally be an oligonucleotide or a population of oligonucleotides comprising a random sequencers) in which the nucleotides at a given position on the oligonucleotide can be any of the four nucleotides, or any of a selected group of the four nucleotides (for example only three of the four nucleotides, or only two of the four nucleotides). In some cases all of the positions of the oligonucleotide or population of oligonucleotides can be any of the four nucleotides, in other cases, only a portion of the position, for instance a particular region, of the oligonucleotide will comprise positions which can be any of the four bases. In some cases, the portion of the oligonucleotide which comprises positions which can be any of the four basis is about 6, 7, 8, 9, 10, 11, 12, 13, 14, or about 15-20 nucleotides in length. In some cases, a random primer may comprise a tailed primer having a 3'-region that comprises a random sequence and a 5'-region that is a non-hybridizing sequence that comprises a specific, non-random sequence. The 3'-region may also comprise a random sequence in combination with a region that comprises poly-T sequences. The sequence of a random primer (or its complement) may or may not be naturally-occurring, or may or may not be present in a pool of sequences in a sample of interest. The amplification of a plurality of RNA species in a single reaction mixture would generally, but not necessarily, employ a multiplicity, preferably a large multiplicity, of random primers. As is well understood in the art, a "random primer" can also refer to a primer that is a member of a population of primers (a plurality of random primers) which collectively are designed to hybridize to a desired and/or a significant number of target sequences. A random primer may hybridize at a plurality of sites on a nucleic acid sequence. The use of random primers provides a method for generating primer extension products complementary to a target polynucleotide which does not require prior knowledge of the exact sequence of the target. In some embodiments one portion of a primer is random, and another portion of the primer comprises a defined sequence. For example, in some embodiments, a 3'-portion of the primer will comprise a random sequence, while the 5'-portion of the primer comprises a defined sequence. In some embodiments a 3'-random portion of the primer will comprise DNA, and a 5'-portion defined portion of the primer will comprise RNA, in other embodiments, both the 3' and 5'-portions will comprise DNA. In some embodiments, the 5'-portion will contain a defined sequence and the 3'-portion will comprise a poly-dT sequence that is hybridizable to a multiplicity of RNAs in a sample (such as all mRNA).

"Protopromoter sequence," and "propromoter sequence," as used herein, refer to a single-stranded DNA sequence region which, in double-stranded form is capable of mediating RNA transcription by DNA-dependent RNA polymerase. In some contexts, "protopromoter sequence," "protopromoter," "propromoter sequence," "propromoter," "promoter sequence," and "promoter" are used interchangeably.

"Propromoter polynucleotide," as used herein, refers to a polynucleotide comprising a propromoter sequence. An example of a propromoter polynucleotide is a propromoter template oligonucleotide (PTO).

"Propromoter template oligonucleotide (PTO)" and "promoter template oligonucleotide (PTO)" as used herein, refer to an oligonucleotide that comprises a propromoter sequence and a portion, generally a 3'-portion, that is hybridizable (under a given set of conditions) to the 3'-region of a primer extension product. The propromoter sequence and the hybridizable portion may be the same, distinct or overlapping nucleotides of an oligonucleotide.

To "inhibit" or "inactivate" is to decrease or reduce an activity, function, and/or amount as compared to a reference.

A "complex" is an assembly of components. A complex may or may not be stable and may be directly or indirectly detected. For example, as is described herein, given certain components of a reaction, and the type of product(s) of the reaction, existence of a complex can be inferred. For purposes of this invention, a complex is generally an intermediate with respect to the final amplification product(s). An example of a complex is a nucleic acid duplex comprising a first primer extension product and a second primer extension product.

A "portion" or "region," used interchangeably herein, of a polynucleotide or oligonucleotide is a contiguous sequence of 2 or more bases. In other embodiments, a region or portion is at least about any of 3, 5, 10, 15, 20, 25 or more contiguous nucleotides.

A region, portion, or sequence which is "adjacent" to another sequence directly abuts that region, portion, or sequence. For example, an RNA portion which is adjacent to a 5'-DNA portion of a composite primer directly abuts that region.

A "reaction mixture" is an assemblage of components, which, under suitable conditions, react to form a complex (which may be an intermediate) and/or a product(s).

Conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, depend upon, for example, the nature of the nucleotide sequence, temperature, and buffer conditions. These conditions also depend on what event is desired, such as hybridization, cleavage, strand extension or transcription.

Sequence "mutation," as used herein, refers to any sequence alteration in a sequence of interest in comparison to a reference sequence. A reference sequence can be a wild type sequence or a sequence to which one wishes to compare a sequence of interest. A sequence mutation includes single nucleotide changes or alterations of more than one nucleotide in a sequence, due to mechanisms such as substitution, transversion, deletion or insertion. Single nucleotide polymorphism (SNP) is also a sequence mutation as used herein.

"Microarray" and "array," as used interchangeably herein, comprise a surface with an array, preferably ordered array, of putative binding (e.g., by hybridization) sites for a biochemical sample (target) which often has undetermined characteristics. In a preferred embodiment, a microarray refers to an assembly of distinct polynucleotide or oligonucleotide probes immobilized at defined positions on a substrate. Arrays are formed on substrates fabricated with materials such as paper, glass, plastic (e.g., polypropylene, nylon, polystyrene), polyacrylamide, nitrocellulose, silicon, optical fiber or any other suitable solid or semi-solid support, and configured in a planar (e.g., glass plates, silicon chips) or three-dimensional (e.g., pins, fibers, beads, particles, microtiter wells, capillaries) configuration. Probes forming the arrays may be attached to the substrate by any number of ways including (i) in situ synthesis (e.g., high-density oligonucleotide arrays) using photolithographic techniques (see, Fodor et al., Science (1991), 251:767-773; Pease et al., Proc. Natl. Acad. Sci. U.S.A. (1994), 91:5022-5026; Lockhart et al., Nature Biotechnology (1996), 14:1675; U.S. Pat. Nos. 5,578, 832; 5,556,752; and 5,510,270); (ii) spotting/printing at medium to low-density (e.g., cDNA probes) on glass, nylon or nitrocellulose (Schena et al, Science (1995), 270:467-470, DeRisi et al, Nature Genetics (1996), 14:457-460; Shalon et al., Genome Res. (1996), 6:639-645; and Schena et al., Proc. Natl. Acad. Sci. U.S.A. (1995), 93: 10539-11286); (iii) by masking (Maskos and Southern, Nuc. Acids. Res. (1992), 20:1679-1684) and (iv) by dot-blotting on a nylon or nitrocellulose hybridization membrane (see, e.g., Sambrook et al., Eds., 1989, Molecular Cloning: A Laboratory Manual, 2nd ed., Vol. 1-3, Cold Spring Harbor Laboratory (Cold Spring Harbor, N.Y.)). Probes may also be non-covalently immobilized on the substrate by hybridization to anchors, by means of magnetic beads, or in a fluid phase such as in microtiter wells or capillaries. The probe molecules are generally nucleic acids such as DNA, RNA, PNA, LNA and cDNA but may also include proteins, polypeptides, oligosaccharides, cells, tissues and any permutations thereof which can specifically bind the target molecules.

The term "3'" generally refers to a region or position in a polynucleotide or oligonucleotide 3' (downstream) from another region or position in the same polynucleotide or oligonucleotide.

The term "5'" generally refers to a region or position in a polynucleotide or oligonucleotide 5' (upstream) from another region or position in the same polynucleotide or oligonucleotide.

The term "3'-DNA portion," "3'-DNA region," "3'-RNA portion," and "3'-RNA region," refer to the portion or region of a polynucleotide or oligonucleotide located towards the 3' end of the polynucleotide or oligonucleotide, and may or may not include the 3' most nucleotide(s) or moieties attached to the 3' most nucleotide of the same polynucleotide or oligonucleotide. The 3' most nucleotide(s) can be from about 1 to about 50, from about 5 to about 40, from about 6 to about 30, from about 10 to about 30, or from about 12 to about 30 nucleotides.

The term "5'-DNA portion," "5'-DNA region," "5'-RNA portion," and "5'-RNA region," refer to the portion or region of a polynucleotide or oligonucleotide located towards the 5' end of the polynucleotide or oligonucleotide, and may or may not include the 5' most nucleotide(s) or moieties attached to the 5' most nucleotide of the same polynucleotide or oligonucleotide. The 5' most nucleotide(s) can be from about 1 to about 50, from about 10 to about 40, or from about 20 to about 40 nucleotides.

As is well understood by those skilled in the art, a "tail" sequence of a primer is a sequence not hybridizable, or not substantially hybridizable to the target sequence under conditions (e.g. ion concentration, temperature, buffer composition, primer concentration, template concentration etc.) in which other region(s) or portion(s) of the primer hybridizes to the target.

"Absent" or "absence" of product, and "lack of detection of product" as used herein includes insignificant, or de minimus levels, generally due to lack of significant accumulation of product due to cycling.

A "DNA-dependent DNA polymerase" is an enzyme that synthesizes a complementary DNA copy from a DNA template. Examples are DNA polymerase I from *E. coli*, bacteriophage T7 DNA polymerase, or DNA polymerases from bacteriophages T4, Phi-29, M2, or T5. DNA-dependent DNA polymerases of the present invention may be the naturally occurring enzymes isolated from bacteria or bacteriophages or expressed recombinantly, or may be modified or "evolved" forms which have been engineered to possess certain desirable characteristics, e.g., thermostability, or the ability to recognize or synthesize a DNA strand from various modified templates. All known DNA-dependent DNA polymerases require a complementary primer to initiate synthesis. It is known that under suitable conditions a DNA-dependent DNA polymerase may synthesize a complementary DNA copy from an RNA template. RNA-dependent DNA polymerases (described below) typically also have DNA-dependent DNA polymerase activity.

A "DNA-dependent RNA polymerase" or "transcriptase" is an enzyme that synthesizes multiple RNA copies from a double-stranded or partially-double-stranded DNA molecule having a promoter sequence that is usually double-stranded. The RNA molecules ("transcripts") are synthesized in the 5'-to-3' direction beginning at a specific position just downstream of the promoter. Examples of transcriptases are the DNA-dependent RNA polymerase from *E. coli* and bacteriophages T7, T3, and SP6.

An "RNA-dependent DNA polymerase" or "reverse transcriptase" ("RT") is an enzyme that synthesizes a complementary DNA copy from an RNA template. All known reverse transcriptases also have the ability to make a complementary DNA copy from a DNA template; thus, they are both RNA- and DNA-dependent DNA polymerases. Reverse transcriptases may also have an RNase H activity. Some examples of reverse transcriptases are reverse transcriptase derived from Moloney murine leukemia virus (MMLV-RT), avian myeloblastosis virus, retroviral reverse transcriptase, retrotransposon reverse transcriptase, hepatitis B reverse transcriptase, cauliflower mosaic virus reverse transcriptase, bacterial reverse transcriptase, *E. coli* DNA polymerase and klenow fragment, and Tth DNA polymerase, A primer is required to initiate synthesis with both RNA and DNA templates. In other examples a DNA dependent DNA polymerase may also comprise an RNA-dependent DNA polymerase such as Klenow polymerase, Bst DNA polymerase and the like.

In some cases, the term "polymerase chain reaction" ("PCR") refers to the method of K. B. Mullis, e.g., as described in U.S. Pat. Nos. 4,683,195 4,683,202, and 4,965,188 (each hereby incorporated in its entirety by reference) and any other improved method known in the art. PCR is a method for exponentially increasing the concentration of a segment of a target sequence in a mixture of genomic DNA without cloning or purification. This process for amplifying the target sequence typically consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction". Because the desired amplified segments of the target sequence become the predominant sequences (in terms of concentration) in the mixture, they are said to be "PCR amplified". In some cases, PCR can be performed in multiplex fashion whereby multiple primer pairs are used to amplify a plurality of double stranded target sequences.

In some cases, the term "PCR" or "linear PCR" is used herein to describe a process, wherein one primer is used to produce amplification of the complement of a single strand in the same manner as above by use of denaturation, annealing and extension cycles. In this case, the amplification is linear rather than exponential due to the use of a single primer. In some cases, linear PCR can be performed in multiplex fashion whereby multiple primers are used to amplify a plurality of single stranded target sequences or their complement.

As used herein, the term "RT-PCR" refers to the replication and amplification of RNA sequences. In this method, reverse transcription is coupled to PCR, e.g., as described in U.S. Pat. No. 5,322,770, herein incorporated by reference in its entirety. In RT-PCR, the RNA template is converted to cDNA due to the reverse transcriptase activity of an enzyme, and then amplified using the polymerizing activity of the same or a different enzyme. Both thermostable and thermolabile reverse transcriptase and polymerase can be used.

The term or "real-time PCR", "quantitative PCR" or "Q-PCR" refers to the replication of polynucleotides such that the number of amplification cycles to reach a certain amount of amplified product is determined and used to calculate the amount of starting product. In some cases, Q-PCR is performed in combination with RT-PCR to first generate a DNA template from a target RNA by RT-PCR and then to use Q-PCR on the DNA template to determine the amount of an RNA such as a transcript or an mRNA, or a set of RNAs that are present in a sample. In some cases, methods other than RT-PCR are used to generate the DNA template from the target RNA. In other cases, Q-PCR is used to quantitate the amount of a DNA or set of DNA targets in a sample. In some cases Q-PCR is performed in a continuous fashion; namely, the amount of amplified product is determined while the amplification is still occurring. Methods and apparatus for performing Q-PCR and variations thereof including but not limited to TaqMan assays are well known in the art and are described for example in U.S. Pat. Nos. 5,994,056; and 5,210,015.

The term "in-vitro transcription" is an RNA amplification technique using a promoter complex and DNA-dependent RNA polymerase to generate multiple copies of the RNA target, e.g. as described in U.S. Pat. Nos. 5,545,522, 5,716,785, and in the Proceedings of the National Academy of Sciences (1990), 87: 1663-1667, each hereby incorporated in its entirety by reference.

Various aspects of the invention are described in further detail in the following subsections.

Overview and Advantages of the Invention

The invention provides novel and improved methods, compositions, and kits for amplification of a target RNA sequence or polynucleotide sequence complementary to an RNA sequence of interest from samples comprising total nucleic acids (i.e. RNA and DNA molecules).

Global amplification of RNA currently generally involves purification of RNA from DNA in the sample in order to prevent amplification from DNA when present in the sample. Examples of undesired amplification products include amplification products from DNA sequences, when present in the sample, other than from RNA targets, which may or may not be products of gene expression, including genomic DNA sequence, plasmid DNA, viral DNA, mitochondrial DNA and the like. Many current global RNA amplification methods employ a reverse transcription step. If such a method is carried out in the presence of DNA, the amplified product from the target RNA will be contaminated by amplified product generated from the single stranded or double stranded DNA in the sample. This is because the reverse transcriptase enzyme does not discriminate between the target RNA and the DNA in the sample, resulting in amplification of both RNA and DNA. Thus, the amplification of sequences from the DNA when present in the sample together with RNA will not be readily distinguishable and will therefore compromise the quality of the amplified RNA product and the amplification efficiency from the RNA target sequences. Purification of RNA from DNA, for example by separating or selectively amplifying only the RNA containing poly-A sequences, or by degrading the DNA (e.g. with DNase) in a sample containing RNA, can result in reduced yield and/or reduced RNA quality. It is highly desirable to develop improved amplification methods of target RNA in the presence of DNA or total nucleic acids. This is especially useful when there are minute amounts of sample for analysis.

An important aspect of the present invention is the minimal production of unwanted products during amplification of a target RNA or sequence complementary to the target RNA while maintaining a high level of specificity and sensitivity. The methods of this invention take advantage of agents which selectively inhibit the activity of DNA-dependent DNA polymerases toward DNA species, a common unwanted amplification template, while allowing RNA-dependent DNA synthesis from RNA targets via reverse transcriptase. Thus, the target RNA species (or a multiplicity of RNAs, e.g., members of a family of related RNAs) or sequence complementary to the target RNA may be amplified in the presence of DNA with decreased levels unwanted amplification products. These methods are useful in maximizing efficiency as well as allowing amplification directly from mixed cultures that may or may not contain both RNA and DNA in the reaction chamber. The selective amplification of specific nucleic acid sequences is of value in increasing the sensitivity of diagnostic and other detection assays while maintaining specificity; increasing the sensitivity, convenience, accuracy and reliability of a variety of research procedures; and providing ample supplies of specific amplification products for various purposes. The methods of the invention are especially suitable for the amplification of all RNA, such as mRNA, sequences in a preparation from a biological sample that may or may not contain DNA. Furthermore, the methods of the present invention may be used to amplify an entire pool of RNA sequences (such as mRNA) without amplifying DNA species, which may be used to analyze the gene expression profile in cells, such as the cells in a biological sample of interest.

Some methods provide for generation of multiple copies of DNA comprising a sequence complementary to a RNA sequence of interest. Other methods provide for generation of multiple copies of an RNA sequence of interest. These methods are suitable for, for example, generation of cDNA libraries, subtractive hybridization probes, sequence analysis such as massively parallel sequencing methods including pyrosequencing, sequencing by synthesis, sequencing by hybridization, single molecule sequencing, nanopore sequencing, and sequencing by ligation, and gene expression profiling, quantitative PCR, and whole transcriptome analysis, SNP analysis, and massarray analysis. They generate single or double stranded DNA or RNA products, which are readily suitable for a variety of uses including expression profiling, e.g., by multiplex analysis, including hybridization methods such as microarray technologies, by quantitative PCR, serial analysis of gene expression (SAGE), and digital PCR, as well as electrophoresis-based technologies such as differential display. The methods are amenable to automation.

Two Part Process: Preparation of Marked DNA and Amplification of Marked DNA

The target nucleic acid contains the target RNA sequence, or sequences, of interest to be amplified in the presence of DNA. The invention can be seen as having two general parts: (1) Preparation of marked DNA sequences representative of the target RNA, usually in the presence of DNA; and (2) Amplification of the marked DNA sequences. By amplifying only the marked DNA sequences, the invention selectively amplifies the sequences representative of the target RNA. Unmarked sequences, related to the DNA in the original sample are not amplified. The methods herein are applicable to amplifying any target nucleic acid comprising RNA, including, for example, mRNA, ribosomal RNA, and viral RNA.

The first part involves preparing a uniquely marked DNA copy of the target RNA sequence. As illustrated in FIG. 1, which outlines a general example of a method of the invention, the target RNA sequence is hybridized to a first primer, generally comprising a 5'-unique non-hybridizing sequence (A) portion with a 3'-hybridizing sequence (B) portion, in the presence of a DNA-dependent DNA polymerase inhibitor, such as actinomycin, for example. A RNA-dependent DNA polymerase, such as reverse transcriptase, is used to extend this first primer to form the first primer extension product (first strand cDNA) that contains a sequence (Y), which is complementary to the target RNA. These steps produce the first primer extension product, which is now uniquely marked with the non-hybridizing 5' sequence (A) for further amplification in a second part of the method. In addition, second stand nucleic acid synthesis, which may inadvertently occur in this step, is specifically inhibited by the DNA-dependent DNA polymerase inhibitor. The DNA-dependent DNA polymerase inhibitor is then removed or inactivated and the target sequence is separated from the first primer extension product, for example, with heat and/or chemical means, using an enzyme that cleaves RNA from an RNA/DNA heteroduplex, or using an enzyme that generally cleaves RNA. A second primer comprising sequence (C) is hybridized to the first primer extension product and is extended by DNA-dependent DNA polymerase to form the second primer extension product containing sequence (Y'), and forming a double stranded cDNA complex with a unique sequence (A/A') at one end. The sequence (C) can comprise a specific sequence, and/or a random sequence. The second primer may be supplied externally as illustrated in FIG. 1 or generated internally as fragments of the target RNA via of the RNA, for example, by enzymes such as RNase or by heat treatment. The use of internally generated fragments of the target RNA allows for a type of random priming of the first primer extension product without the addition of random primers. As used herein, it is understood that "cDNA" refers to a polynucleotide primer extension product.

The second part of the method involves amplification of the marked DNA sequence using the unique sequence (A), (A') or (A/A') of the single or double stranded cDNA as a template for amplification of polynucleotide sequences using amplification methods described herein and known in the art. Nucleic acid amplification methods can be used in the invention, for example, to amplify nucleic acids complementary to the RNA target or to generate multiple copies the transcription product of the cDNA. Amplification methods useful for the methods of the invention include single primer linear isothermal amplification (SPIA), linear or exponential PCR, RNA transcription via a propromoter template oligonucleotide (PTO), and other amplification techniques such as transcription mediated amplification (TMA), strand displacement amplification (SDA), and rolling circle amplification (RCA), which are be further described herein.

In some embodiments, the steps are performed in the order that is described. In other embodiments, one or more steps described in this application may be combined and/or performed in any order, as long as the requisite product(s) are able to be formed, and, as is evident, the invention includes various combinations of the steps described herein. For example, it is understood that the inactivation of the DNA-dependent DNA polymerase inhibitor may be performed before or after cleavage of the target RNA from the RNA/DNA heteroduplex. It is also evident, and will be briefly described below to highlight this point, that the invention encompasses methods in which the initial, or first, step is any of the steps described herein. For example, the methods of the invention do not require that the first step be production of the first primer extension product from the RNA template. Methods of the invention encompass embodiments in which later, "downstream" steps are an initial step.

It is understood that various other embodiments may be practiced, given the general description provided above. For example, reference to using a composite primer means that any of the composite primers described herein may be used.

Amplification Via SPIA

In some aspects of the invention, the amplification method that is used to amplify the marked DNA is a single primer isothermal amplification using a complex comprising a RNA/DNA partial heteroduplex as a template. In this method, termed single primer linear isothermal amplification (SPIA), a complex comprising a RNA/DNA partial heteroduplex is a substrate for further amplification as follows: an enzyme (such as RNase H), which cleaves RNA sequence from an RNA/DNA heteroduplex, cleaves the RNA sequence (A) from the partial heteroduplex, leaving a partially double stranded polynucleotide complex comprising an exposed 3' single-stranded DNA sequence. The 3' single-stranded sequence (formed by cleavage of RNA in the complex comprising a RNA/DNA partial heteroduplex) is generally the complement of a composite amplification primer, and thus forms a specific binding site for the composite amplification primer. This composite amplification primer is the third primer used in this invention and also comprises a unique 5'-sequence. Extension of a bound composite amplification primer by a DNA-dependent DNA polymerase with strand displacement activity produces a primer extension product, which displaces the previously bound cleaved primer extension product, whereby single stranded DNA product accumulates. The single stranded DNA product is a copy of the complement of the target RNA (or "antisense" DNA). The cycle repeats with the removal of the unique sequence on the 5'-tail of the primer extension product, exposing the 3'-end of the second primer extension product for another cycle of amplification. This linear amplification is referred to as "SPIA" (for Single Primer Linear Isothermal Amplification), and is described in Kurn et al., U.S. Pat. Nos. 6,251,639 and 6,692,918.

Amplification using a complex comprising a RNA/DNA partial heteroduplex as a template for further amplification by SPIA generally occurs under conditions permitting composite primer hybridization, primer extension by a DNA polymerase with strand displacement activity, cleavage of RNA from a RNA/DNA heteroduplex and strand displacement. In so far as the composite amplification primer hybridizes to the 3'-single-stranded portion (of the partially double stranded polynucleotide which is formed by cleaving RNA in the complex comprising a RNA/DNA partial heteroduplex) comprising, generally, the complement of at least a portion of the composite amplification primer sequence, composite primer hybridization may be under conditions permitting specific hybridization.

In some embodiments, the methods of the invention result in amplification of a multiplicity, a large multiplicity, or a very large multiplicity of target RNA. In some embodiments, essentially all of the target RNA present in the initial sample (e.g., all of the mRNA) is amplified. In other embodiments, at least 1, at least 5, at least 10, at least 20, at least 50, at least 100, at least 200, at least 300, up to at least 10,000 or more distinct sequences (such as other sub-segments of a RNA) are amplified, as assessed, e.g., by analysis of marker sequences known to be present in the template sample under analysis, using methods known in the art. Target RNA sequences that are amplified may be present on the same RNA strand or on different RNA strands. It will be understood by those of skill in the art that the global amplification methods of the invention are suitable for amplification of any pool or subset of RNA.

In some embodiments, the methods of the invention are used to globally amplify a single stranded RNA target or the double stranded DNA that is initially produced from the RNA target using methods described herein. In these cases, the amplification product will generally be a copy of either the target RNA (sense copy) or of the complement to the target RNA (antisense copy). Whether the sense or antisense copy is produced will depend on the method, as will be understood by one of ordinary skill in the art. In some embodiments, the amplification product of different senses can be annealed to form a double-stranded (or partially double-stranded) complex. In other embodiments, they can be prevented from annealing (or subsequently denatured) to produce a mixture of single stranded amplification products. The amplified products may be of differing lengths.

As illustrated in these embodiments, all steps are isothermal (in the sense that thermal cycling is not required), although the temperatures for each of the steps may or may not be the same. It is understood that various other embodiments may be practiced, given the general description provided above. For example, as described and exemplified herein, certain steps may be performed as temperature is changed (e.g., raised, or lowered).

For simplicity, the isothermal amplification methods of the invention are described as two distinct steps or phases, above. It is understood that the two phases may occur simultaneously in some embodiments (for example, if the enzyme that cleaves RNA from RNA/DNA heteroduplex is included in the first reaction mixture).

Although generally only one composite amplification primer is described above, it is further understood that the amplification methods may be performed in the presence of two or more different first and/or second composite primers that randomly prime template polynucleotide. In addition, the amplification polynucleotide products of two or more separate amplification reactions conducted using two or more different first and/or second composite primers that randomly prime template polynucleotide can be combined.

In one aspect, the invention provides methods of generating multiple copies of a polynucleotide sequence complementary to an RNA sequence of interest in the presence of DNA, illustrated in FIG. 2, as follows: (a) hybridizing a first primer to the target RNA sequence in the presence of a DNA-dependent DNA polymerase inhibitor, e.g. actinomycin, wherein the first primer comprises a 3'-DNA sequence (B) and a 5'-RNA sequence (A); (b) extending the first primer with an RNA-dependent DNA polymerase in the presence of a DNA-dependent DNA polymerase inhibitor, whereby a complex comprising a first primer extension product (interchangeably called "first strand cDNA") and the target RNA is produced, wherein the 5'-end of the first primer extension product is the first primer sequence (A); (c) inactivating and/or removing the DNA-dependent DNA polymerase inhibitor, e.g. actinomycin, using methods described herein and cleavage of the target RNA; (d) extending a second primer hybridized to the first primer extension product at sequence (C') with a DNA-dependent DNA polymerase, wherein a second primer comprises a hybridizing DNA sequence (C), or extending a fragment of the RNA template, which is hybridizing to sequence (C'), whereby a second primer extension product (interchangeably called "second strand cDNA") is produced to form a complex of first and second primer extension products and comprises the sequence (A') complementary to (A). The complex of first and second primer extension products is composed of a RNA/DNA heteroduplex at one end due to the presence of the composite primer in the first primer extension product. As previously described herein, the second primer may be supplied externally, where it hybridizes to a specific sequence on the first strand cDNA, or may be generated internally as fragments of the target RNA via enzymatic cleavage by enzymes such as RNase or by other processes such as heat treatment. In the case of the latter source of the second primer, the primer will not be directed to a specific sequence on the first strand cDNA.

Figure 2B:
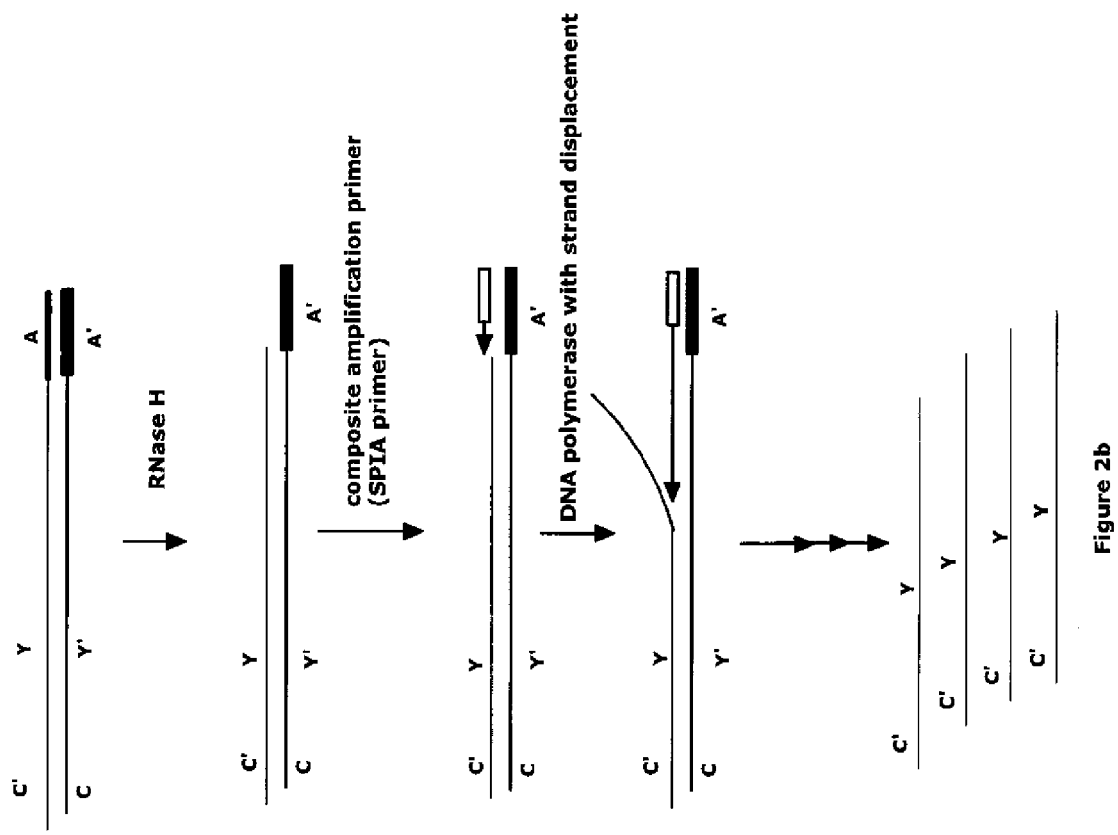

Following generation of the double stranded cDNA product with the marked first strand cDNA sequence, the second part in the process, as illustrated in FIG. 2b, may involve SPIA amplification which may be performed as follows: (e) cleaving RNA from the first primer in the complex of first and second primer extension products with an enzyme, such as RNaseH, that cleaves RNA from an RNA/DNA heteroduplex such that a third composite amplification primer hybridizes to the second primer extension product at sequence (A'), wherein the composite amplification primer comprises an RNA portion and a 3' DNA portion; (f) extending the composite amplification primer hybridized to the second primer extension product with a DNA-dependent DNA polymerase to produce another composite primer extension product; whereby the first primer extension product is displaced, and whereby multiple copies of a polynucleotide sequence complementary to the RNA sequence of interest are generated. This amplification step produces the complement containing the sequence (C') and the sequence (Y), which is downstream of (C'), that is complementary to the sequence of the target RNA.

As is clear to one skilled in the art, reference to production of copies of a RNA sequence of interest or copies of a polynucleotide sequence complementary to a RNA sequence of interest refers to products that may contain, comprise or consist of such sequences. As is evident to one skilled in the art, aspects that refer to combining and incubating the resultant mixture also encompasses method embodiments which comprise incubating the various mixtures (in various combinations and/or subcombinations) so that the desired products are formed.

For example, in some aspects, the components of the invention may be combined and reacted in a reaction mixture where SPIA is allowed to proceed. The invention provides methods of generating multiple copies of a polynucleotide sequence complementary to an RNA sequence of interest, said method comprising the steps of: combining and reacting: the complex of first and second primer extension products described above; a composite amplification primer (which may or may not be the same as the first primer) that is hybridizable to the second primer extension product, wherein said composite amplification primer comprises an RNA portion and a 3' DNA portion; a DNA-dependent DNA polymerase; and an agent (such as an enzyme) that cleaves RNA from an RNA/DNA heteroduplex; wherein the mixture is incubated under conditions (which include necessary substrates and buffer conditions) that permit RNA cleavage from the first strand cDNA, composite amplification primer hybridization to the second strand cDNA, composite amplification primer extension, resulting in displacement of the first primer extension product from the complex.

Amplification Via Transcription

In another aspect of this invention, the second part of the method is amplification of the marked DNA sequence through transcription to generate a copy of the target RNA sequence. This transcription step can involve the use of a PTO and the unique sequence (A), (A'), or (A/A') of the single or double stranded cDNA, generated using any of the described methods herein. The PTO comprises a 3'-hybridizing region and a 5'-non-hybridizing (tail) region with the propromoter sequence. In some aspects, the unique sequence (A/A') may be a double stranded promoter, as further described below. As described herein, the PTO may comprise RNA, DNA, or combinations thereof.

The use of a first primer (first strand cDNA primer) comprising a 3'-hybridizable region and a 5'-tail region comprising a single strand sequence of a promoter for DNA-dependent RNA polymerase has been described before in U.S. Pat. Nos. 5,545,522, 5,716,785, and Proceedings of the National Academy of Sciences (1990), 87: 1663-1667, each hereby incorporated in its entirety by reference. When first strand synthesis is carried out in the presence of a DNA-dependent DNA polymerase inhibitor, only copies of the target RNA will be generated. The product of the first and second primer extension products generated by this method is a double stranded DNA with a double stranded promoter sequence at one end, which is the substrate for the DNA dependent RNA polymerase, such as for example T7 RNA polymerase, SP6 RNA polymerase and the like.

Figure 3:
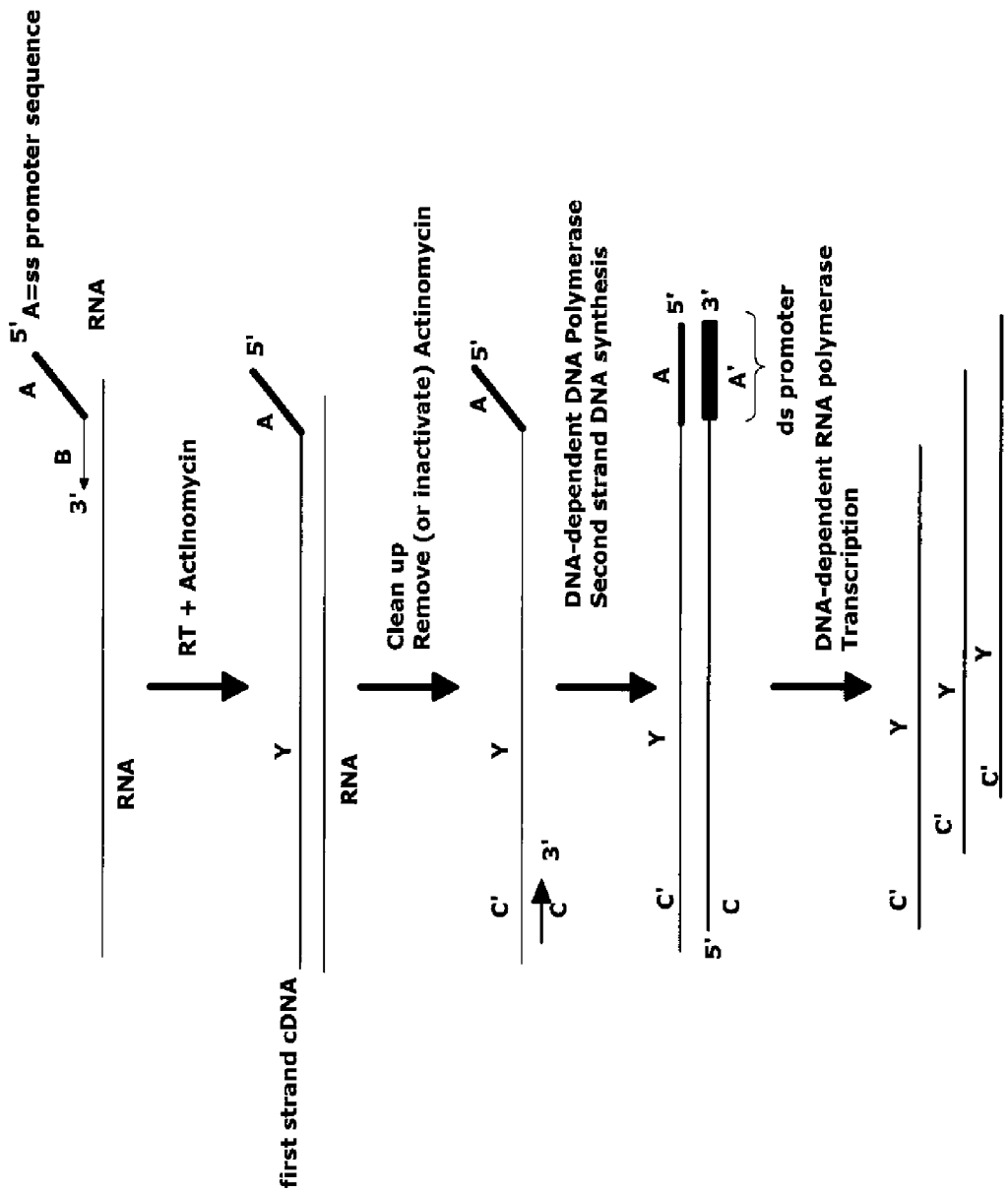
FIG. 3 is a diagrammatic representation of an embodiment of the invention in which the first primer comprises a promoter sequence as a marker, and the first primer extension product is formed on an RNA target in the presence of a DNA-dependent DNA polymerase (actinomycin). Transcription (IVT) with an RNA polymerase is used to generate multiple copies of the sequence complementary to the target RNA.

For example, in one aspect involving transcription illustrated in FIG. 3, the invention provides methods of generating multiple copies of (amplifying) an RNA sequence of interest. The first primer is the single stranded PTO comprising a 3'-hybridizing sequence (B) and 5'-non-hybridizing sequence (A) which serves as a propromoter for DNA-dependent RNA polymerase. In the presence of actinomycin, the first strand cDNA is generated by reverse transcriptase and the resulting first strand cDNA contains the sequence (Y) and 5'-sequence (A). Following inactivation or removal of actinomycin and removal of the target RNA from the complex, a second primer, which contains sequence (C), hybridizes to the 3'-end of the first strand cDNA and is extended using DNA-dependent DNA polymerase. The second strand cDNA that is generated is in a complex with the first strand cDNA and contains the double stranded promoter sequence (A/A'), thus enabling RNA synthesis through transcription via RNA polymerase. Multiple copies of the sequence complementary to the target RNA with sequence (C') and (Y) are generated in this aspect.

As previously described, the second primer may also be endogeneous in the form of a fragment or fragments of the target RNA sequence which is cleaved following first strand synthesis using methods described herein. In this case, the second primer is not hybridized to a specific sequence on the cDNA but rather to various regions of the sequence (Y) on the first strand cDNA since the fragments are generated from randomly cleaved portions and therefore are hybridized to random locations on the cDNA. In this aspect, multiple copies generated comprise the various sequences ($Y_1, Y_2, Y_3 \ldots$) that are homologous to various regions of the target RNA.

In another aspect, a PTO is used as the second primer to form a double stranded complex composed of a promoter sequence for transcription. One embodiment of a PTO comprises a second primer with a 3' hybridizing end and a 5' non-hybridizing end, which contains a propromoter sequence. The 3'-end (e.g. sequence (C) hybridizes to the 3'-end of the first primer extension product (first strand cDNA), which contains a 5' sequence (A) and was formed from the steps described above. Extension of the PTO by DNA polymerase produces a double stranded complex containing a sequence (A/A') at one end, and a propromoter sequence incorporated into the second strand. Following the denature of the double stranded cDNA, a primer with sequence (A) is hybridized to the second extension product and is extended to form a double stranded product having a double stranded promoter sequence from which transcription occurs using RNA polymerase at one end, and the sequence (A/A') at the other end. The double stranded promoter region can be used to promote transcription by an RNA polymerase. The result of the transcription can be an amplification step that generates multiple copies of a RNA sequence of interest.

In yet another aspect involving transcription, the invention provides methods of generating multiple copies of (amplifying) a sequence complementary to an RNA sequence of interest comprising: (a) hybridizing a PTO to the 3'-end of a second strand cDNA, wherein the second strand cDNA comprises a 5'-sequence (C) and a 3'-sequence (A') and is generated using any of the methods described herein and wherein the PTO comprises a 3'-hybridizing end with sequence (A) that is generally, but not necessarily, blocked so that it cannot be extended by the DNA polymerase, and a 5'-nonhybridizing propromoter sequence (P); (b) extending the second strand cDNA by DNA polymerase to produce a double stranded promoter, enabling RNA amplification through transcription via DNA-dependent RNA polymerase. Multiple copies of a sequence complementary to the target RNA are generated in this aspect.

Amplification Via PCR

In some aspects of the second part of the invention, amplification methods such as linear or exponential PCR, are utilized to perform the amplification of marked cDNA.

In some aspects of the invention, exponential amplification of nucleic acids is used in the second step to amplify the marked DNA. These methods often depend on the product catalyzed formation of multiple copies of a nucleic acid or its complement. The amplification products are sometimes referred to as "amplicons." One such method for the enzymatic amplification of specific double stranded sequences of DNA is known as the polymerase chain reaction (PCR) (see U.S. Pat. No. 4,683,195 and U.S. Pat. No. 4,683,202). The DNA amplification is based on the activity of the enzyme DNA polymerase, which elongates primer molecules that bind to the template DNA by adding dNTPs and thereby copies the template sequence (Saiki et. al, Science (1988), 239: 487-491). The forward primer binds to the 3'-end of the sense strand of the template, whereas the reverse primer binds to the 3'-end of the reverse strand, hereby defining the starting points of the polymerase reaction and eventually determining the length of the amplified product.

PCR is an amplification procedure is based on repeated cycles of denaturation, oligonucleotide primer annealing, and primer extension, usually by thermophilic template dependent polynucleotide polymerase, resulting in the exponential increase in copies of the desired sequence of the polynucleotide analyte flanked by the primers. The two different PCR primers, which anneal to opposite strands of the DNA, are positioned so that the polymerase catalyzed extension product of one primer can serve as a template strand for the other, leading to the accumulation of a discrete double stranded fragment whose length is defined by the distance between the 5'-ends of the oligonucleotide primers.

Linear amplification generally refers to a method that involve the formation of one or more copies of the complement of only one strand of a nucleic acid or polynucleotide molecule, usually a nucleic acid or polynucleotide analyte. Thus, the primary difference between linear amplification and exponential amplification is that in the latter the product serves as a template for the formation of more products, whereas in the former process the starting sequence serves as a template for the formation of product but the product is not itself replicated. In linear amplification the amount of product formed increases as a linear function of time as opposed to exponential amplification where the amount of product formed is an exponential function of time.

In one aspect, the invention provides methods of generating multiple copies of a polynucleotide sequence complementary to an RNA sequence of interest or an RNA sequence of interest in the presence of DNA, said method comprising the steps of: (a) extending a first primer hybridized to a target RNA with an RNA-dependent DNA polymerase in the presence of a DNA-dependent DNA polymerase inhibitor, wherein the first primer is a composite primer comprising a 5'-non-hybridizing region (tailed primer), whereby a complex comprising a first primer extension product and the target RNA is produced; (b) cleaving the target RNA in the complex of step (a) with an enzyme that cleaves RNA and from an RNA/DNA hybrid; (c) inactivating and/or removing the DNA-dependent DNA polymerase inhibitor as described herein; (d) extending a second primer hybridized to the first primer extension product with a DNA-dependent DNA polymerase, whereby a second primer extension product is produced to form a complex of first and second primer extension products; (e) amplifying each of the first and second strand cDNA using either or both the first and second primers via linear or exponential amplification using techniques described in sections above, such as PCR; whereby multiple copies of a polynucleotide sequence homologous or complementary to the RNA sequence of interest are generated. In some aspects, step (c) may be performed before or in combination with step (b).

Figure 4:
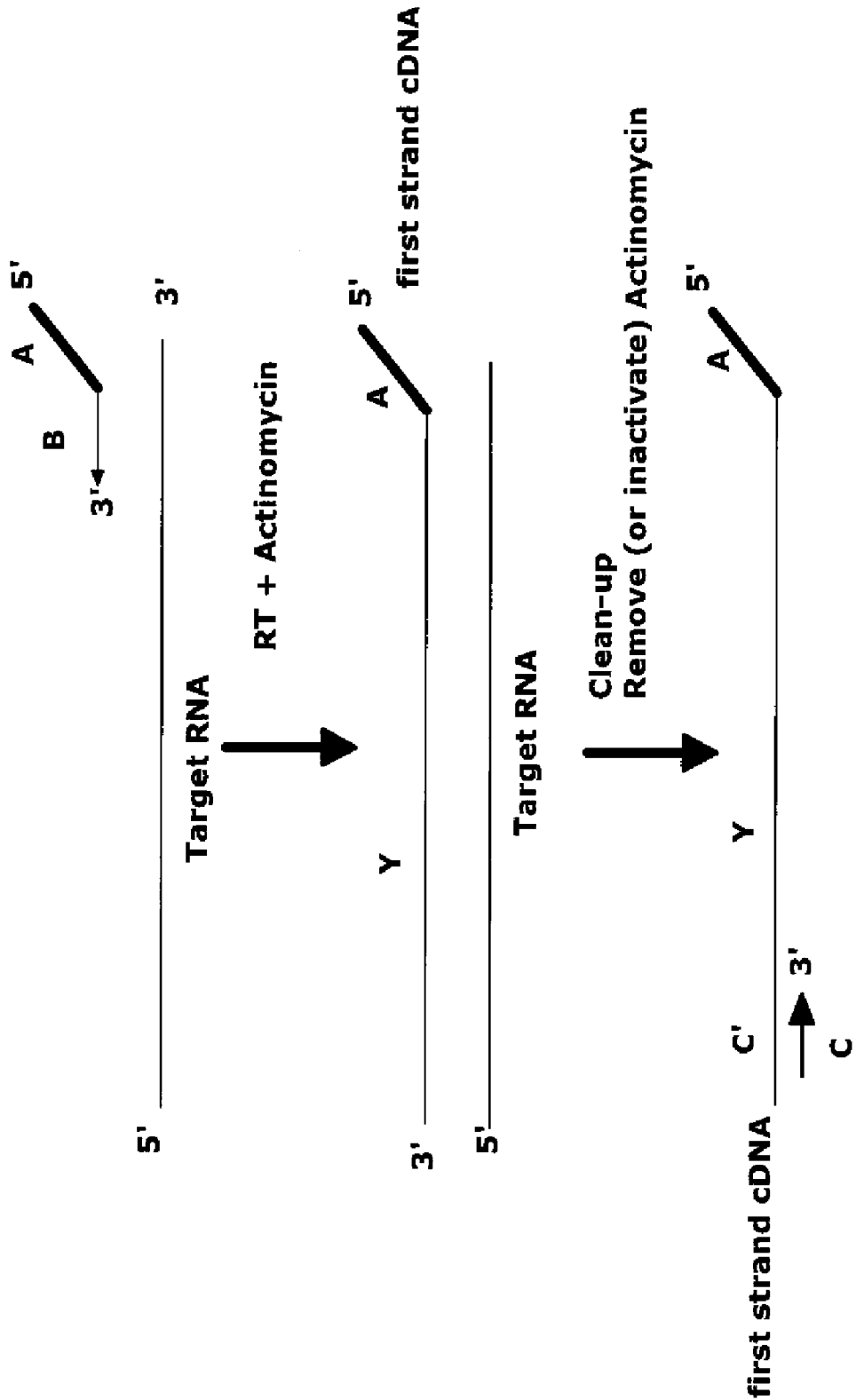
FIGS. 4a, 4b, and 4c are diagrammatic representations an embodiment of the invention in which PCR is used to amplify the marked cDNA.

In one embodiment, as illustrated in FIG. 4a, the amplification methods of the invention results in generation of DNA products comprising sequences complementary to an RNA sequence(s) of interest is as follows: (a) A first primer having a 5'-sequence (A) that is non-complementary to the target RNA binds to an RNA species in a sample by hybridization of the 3'-sequence portion (B) to form a complex in the presence of a DNA-dependent DNA polymerase inhibitor such as actinomycin; (b) A reverse transcriptase (RT) extends the hybridized first primer along the target RNA strand to which it is hybridized, to form an RNA/DNA heteroduplex. The DNA-dependent DNA polymerase inhibitor prevents extension of product from DNA in the sample. The 5'-end of the first primer extension product has the first primer sequence (A); (c) The target RNA strand of the heteroduplex may be degraded, by methods described herein, to generate a single-stranded first strand cDNA; (d) The DNA-dependent DNA polymerase inhibitor is removed, inhibited, inactivated or sequestered; (d) The second primer with sequence (C) binds to first strand cDNA by hybridization to form a complex.

Linear or exponential PCR can then be used to amplify only the marked cDNA which is formed. PCR involves, for example, linear PCR (FIG. 4b) or exponential PCR (FIG. 4c), wherein the cDNA generated in the first step is amplified. The unique non-complementary sequence of the first primer is used in subsequent amplification steps to generate only the desired product.

In FIG. 4b, illustrating linear PCR, the second strand cDNA with the 3'-sequence (A') is hybridized to the primer with sequence (A), which is extended by DNA polymerase to generate multiple copies of DNA that are complementary to the target RNA.

Figure 4C:
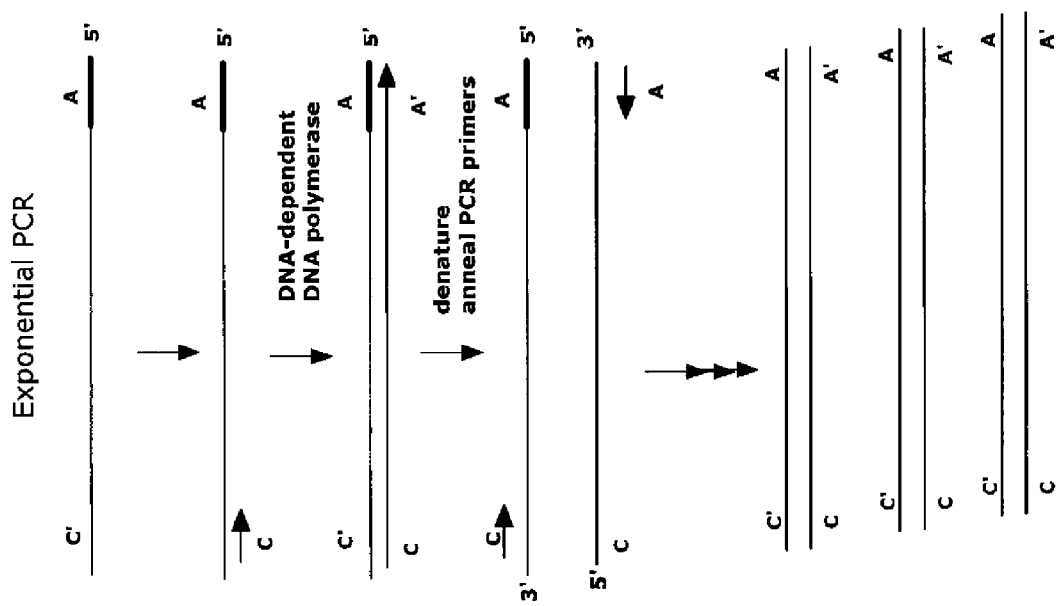

Exponential PCR is illustrated in FIG. 4c, wherein both the first and second strand cDNA are exponentially amplified using exponential PCR. The two cDNA strands are denatured and the two primers with sequence (A) and sequence (C) are used simultaneously to amplify both cDNA strands. A primer with sequence (C) is annealed to the first strand cDNA comprising sequences (C') and (A) and is extended to produce strands containing sequence (C). A primer with sequence (A) is annealed to the second strand cDNA comprising sequences (C) and (A') and is extended to produce strands containing sequence (C'). Exponential PCR can also be carried out with one primer comprising a sequence (A) and the other primer comprising a sequence (Y'), complementary to sequence (Y). It will be understood that the PCR primers need not comprise all of sequence (C) or sequence (Y'), but may only comprise a portion of such sequences. In some cases, multiple PCR primer pairs can be employed in order to obtain multiplex PCR and amplification of multiple sequences of interest.

Other Methods of Amplification

The second part of the invention may also amplify the marked DNA sequence using other amplification methods known in the art. The following are descriptions of some examples of amplification methods. It is understood that the invention is not limited to the amplification methods described herein. Any amplification method that can amplify the marked polynucleotides produced in the first part of the invention may be used. In some cases, amplification methods can comprise tonal amplification. Clonal amplification is the generation of one or more unique sets of amplified DNA such that each set is separated physically, or chemically from other sets. Methods of clonal amplification include amplifying DNA on a solid surface such as a bead or beads, an array, or a set of wells. In some cases, clonal amplification may be performed by isolating template polynucleotides in individual microreactors such as for example individual aqueous droplets of a water in oil emulsion. Each amplified template will then be isolated from the other templates to generate clonal populations of amplified product in each droplet. In some cases, the droplets further contain a solid surface such as a bead. In some cases, initially, each bead will carry a single DNA molecule. After amplification (e.g. PCR, or SPIA), each bead will contain thousands to millions of identical copies of the DNA molecule. Other methods of clonal amplification are provided herein.

One example for achieving a nucleic acid amplification is the nucleic acid sequence based amplification (NASBA). This method is a promoter-directed, enzymatic process that induces in vitro continuous, homogeneous and isothermal amplification of a specific nucleic acid to provide RNA copies of the nucleic acid. The reagents for conducting NASBA include a first DNA primer with a 5'-tail comprising a promoter, a second DNA primer, reverse transcriptase, RNaseH, T7 RNA polymerase, NTPs and dNTPs.

Another method for amplifying a specific group of nucleic acids is the Q-beta-replicase method, which relies on the ability of Q-beta-replicase to amplify its RNA substrate exponentially. The reagents for conducting such an amplification include "midi-variant RNA" (amplifiable hybridization probe), NTPs, and Q-beta-replicase.

Another method for amplifying nucleic acids is known as 3SR and is similar to NASBA except that the RNase H activity is present in the reverse transcriptase. Amplification by 3SR is an RNA specific target method whereby RNA is amplified in an isothermal process combining promoter directed RNA polymerase, reverse transcriptase, and RNase H with target RNA.

Another method for amplifying nucleic acids is Transcription Mediated Amplification (TMA) used by Gen-Probe. The method is similar to NASBA in utilizing two enzymes in a self-sustained sequence replication. (See Fahy, et al., Patent Application WO 91-US8488 911113).

Another method for amplification of nucleic acids is Strand Displacement Amplification (SDA) (Westin et al., Nature Biotechnology (2000), 18: 199-202; Walker et al., Nucleic Acids Research (1992), 20(7): 1691-1696), which is an isothermal amplification technique based upon the ability of a restriction endonuclease such as HincII or BsoBI to nick the unmodified strand of a hemiphosphorothioate form of its recognition site, and the ability of an exonuclease deficient DNA polymerase such as Klenow exo minus polymerase, or Bst polymerase, to extend the 3'-end at the nick and displace the downstream DNA strand. Exponential amplification results from coupling sense and antisense reactions in which strands displaced from a sense reaction serve as targets for an antisense reaction and vice versa.

Another method for amplification of nucleic acids is Rolling Circle Amplification (RCA) (Lizardi et al., Nature Genetics (1998), 19:225-232). RCA can be used to amplify single stranded molecules in the form of circles of nucleic acids. In its simplest form, RCA involves the hybridization of a single primer to a circular nucleic acid. Extension of the primer by a DNA polymerase with strand displacement activity results in the production of multiple copies of the circular nucleic acid concatenated into a single DNA strand. The method of generating polonies is one method of clonal amplification.

In some embodiments, amplification methods can be solid-phase amplification, polony amplification, colony amplification, emulsion PCR, bead RCA, surface RCA, surface SDA, etc., as will be recognized by one of skill in the art. In some embodiments, amplification methods that results in amplification of free DNA molecules in solution or tethered to a suitable matrix by only one end of the DNA molecule can be used. Methods that rely on bridge PCR, where both PCR primers are attached to a surface (see, e.g., WO/18957 and Adessi et al., Nucleic Acids Research (2000), 28(20): E87) can be used. In some cases the methods of the invention can create a "polymerase colony technology", or "polony", referring to a multiplex amplification that maintains spatial clustering of identical amplicons (see Harvard Molecular Technology Group and Lipper Center for Computational Genetics website). These include, for example, in situ polonies (Mitra and Church, Nucleic Acid Research 27, e34, Dec. 15, 1999), in situ rolling circle amplification (RCA) (Lizardi et al., Nature Genetics (1998), 19:225-232), bridge PCR (U.S. Pat. No. 5,641,658), picotiter PCR (Leamon et al., Electrophoresis (2003), 24: 3769), and emulsion PCR (Dressman et al., PNAS (2003), 100: 8817). The methods of the invention provide new methods for generating and using polonies.

A polony is a contraction of "polymerase colony," a small colony of DNA; Polonies are discrete clonal amplifications of a single DNA molecule, grown in a gel matrix or on a surface. This approach greatly improves the signal-to-noise ratio. Polonies can be generated using several techniques that include for example solid-phase PCR in polyacrylamide gels, bridge PCR on a solid phase, or SPIA amplification on a solid surface. In some cases, growth of clonal copies of DNA on bead surfaces may be considered a "polony" method. The method of generating polonies is one method of clonal amplification.

General Techniques

The practice of the invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

Primers, oligonucleotides, and polynucleotides employed in the invention can be generated using standard techniques known in the art.

Components and Reaction Conditions Used in the Methods of the Invention

Template Nucleic Acid

The RNA target is generally a polymeric nucleotide, which in the intact natural state can have about 30 to 5,000,000 or more nucleotides and in an isolated state can have about 20 to 50,000 or more nucleotides, usually about 100 to 20,000 nucleotides, more frequently 500 to 10,000 nucleotides. The RNA target to be amplified includes RNAs from any source and or/species, including human, animals, plants, and microorganisms such as bacteria, yeasts, viruses, viroids, molds, fungi, plants, and fragments thereof. Exemplary RNA targets can be obtained and purified using standard techniques in the art and includes RNAs in purified or unpurified form, which include, but are not limited to, mRNAs, tRNAs, snRNAs, rRNAs, retroviruses, small non-coding RNAs, microRNAs, polysomal RNAs, pre-mRNAs, intronic RNA, viral RNA, DNA-RNA heteroduplexes and fragments thereof. Amplification of a DNA target (including genomic DNA target) would require initial transcription of the DNA target into RNA form, which can be achieved using methods disclosed in Kurn, U.S. Pat. No. 6,251,639 B1, and by other techniques (such as expression systems) known in the art. Amplification of a RNA/DNA heteroduplex would require denaturation of the duplex to obtain a ssRNA, or denaturation followed by transcription of the DNA strand to obtain an RNA. The target RNA may be only a minor fraction of a complex mixture such as a biological sample and may be obtained from various biological materials by procedures well known in the art.

The target RNA can be known or unknown and may contain more than one desired or suspected specific nucleic acid sequence of interest, each of which may be the same or different from each other. Therefore, the amplification process is useful not only for producing large amounts of one specific nucleic acid sequence, but also for amplifying simultaneously more than one different specific nucleic acid sequence located on the same or different nucleic acid molecules. The initial step of the amplification of a target RNA sequence is rendering the target single stranded. If the target nucleic acid is double stranded (e.g., RNA/DNA heteroduplex) the initial step could be target denaturation. Denaturation may also be carried out to remove secondary structure present in a RNA target molecule. The denaturation step may be thermal denaturation or any other method known in the art.

First Primer

The first primer is marked in a manner that when the first primer is used to form a first primer extension product, the first primer extension product (and in some cases subsequent extension products such as the second primer extension product) are marked. Various embodiments of the first primer are used in the methods of the invention are described herein. For the methods described herein, one or more first primers may be used.

Generally, the first primer comprises a 5'-unique sequence and is generally a tailed primer comprising a non-hybridizing 5'-sequence. The 5'-unique sequence allows the first strand cDNA to be uniquely marked in a sample containing other nucleic acids. In one embodiment the first primer is a primer comprising only DNA. In another embodiment, the first primer is a primer comprising only RNA. In another embodiment, the first primer is a composite primer comprising a combination of DNA and RNA. Extension of the first primer results in a complex of first and second strand cDNAs that comprise a portion with a particular characteristic (e.g., cleavable by an enzyme) or sequence content (for example comprising a promoter for DNA dependent RNA polymerase). In another embodiment, the first primer may comprise a 5'-unique end that can partially hybridize to the target. In another embodiment, the first primer may comprise all hybridizable portions but the 5'-end is uniquely marked with groups that distinguish it from the other nucleic acid samples.

Generation of primers suitable for extension by polymerization is well known in the art, such as described in PCT Pub. No. WO99/42618 (and references cited therein). The first primer may comprise a combination of RNA and DNA, with the 3'-end nucleotide being a nucleotide suitable for nucleic acid extension. The 3'-end nucleotide can be any nucleotide or analog that when present in a primer, is extendable by a DNA polymerase when hybridized to a polynucleotide template. Generally, the 3'-end nucleotide has a 3'-OH. Suitable primers include those that comprise at least one portion of RNA and at least one portion of DNA. For example, first primers may comprise a 5'-RNA portion and a 3'-DNA portion (in which the RNA portion is adjacent to the 3'-DNA portion); or 5'- and 3'-DNA portions with an intervening, RNA portion. Accordingly, in one embodiment, the first primer comprises a 5'-RNA portion and a 3'-DNA portion, wherein the RNA portion is adjacent to the 3'-DNA portion. In another embodiment, the first primer comprises 5'- and 3'-DNA portions with at least one intervening RNA portion (i.e., an RNA portion between the two DNA portions). In yet another embodiment, the first primer of the invention comprises a 3'-DNA portion and at least one intervening RNA portion (i.e., an RNA portion between DNA portions).

The first primer extension product comprises a specific sequence complementary to an RNA sequence and a 5' portion, preferably a 5' end, which comprises RNA, DNA, or combinations thereof. For example, in some embodiments, the RNA portion of a first primer is 5' with respect to the 3' DNA portion. In still other embodiments, the 5' RNA portion is adjacent to the 3' DNA portion. In some embodiments, a first primer comprises a 5' portion (for example, a 5' RNA portion) that is either defined or universal and non-hybridizable to a target RNA under conditions which the composite primer hybridizes to target RNA. The 3'-DNA portion may be sequence specific and hybridizable to the target sequence or contain multiple sequences, random sequences, partially random sequences, and/or a poly-dT sequences for hybridizing to the Poly-A sequence on the mRNA target.

The 5'-region of the first primer of the present invention may include a propromoter sequence recognized by an RNA polymerase such as for example T7 RNA polymerase, SP6 RNA polymerase and the like.

In other embodiments, the first primers comprises a sequence entirely of DNA with a 3'-DNA portion that generally is designed to be hybridizable to a target RNA(s). This 3'-DNA portion may be sequence specific and hybridizable to a specific sequence of the target sequence, random sequences, partially random sequences, and/or a poly-dT sequences for hybridizing to the Poly-A sequence on the mRNA target. One or multiple first primers may be used for the amplification methods of the invention. The remaining portion(s) (such as the 5'-DNA portion) of the first primer generally, but not necessarily, comprises a defined or universal sequence that is not hybridizable to a target RNA (which would constitute a tail when the primer is bound to a target RNA). Thus, and as the description herein makes clear, reference to a primer that hybridizes to a sequence (or hybridization template) encompasses embodiments in which at least a portion of the primer is hybridized, as well as those embodiments in which an entire primer is hybridized.

In still other embodiments, a plurality of first primers are used for hybridizing to the target RNA. In some embodiments, the first primer that hybridizes to target RNA and the composite amplification primer that hybridizes to second primer extension product are the same. In other embodiments, the first primer that hybridizes to target RNA and the composite amplification primer that hybridizes to second primer extension product are different.

Insofar as many mRNAs have a unique poly-A 3'-end, amplification initiated from the 3'-end sequence of mRNAs is commonly performed for preparation of cDNA libraries and subsequent sequence analysis for determination of gene expression profiling or other applications. The methods of the invention are similarly suited for preparation of libraries of amplified 3'-portions of mRNAs. Similarly, the methods of the invention are suited for preparation of libraries of whole transcriptome amplification. It is understood that the methods of the invention are useful not only for producing large amounts of one specific nucleic acid sequence, but also for amplifying simultaneously more than one different specific nucleic acid sequence located on the same or different target nucleic acid molecules. For example, the methods of the invention are useful for amplifying all mRNA in a sample, or for amplifying a multiplicity of specific RNA species (in which case a multiplicity of the first primer each comprising a 3'-portion hybridizable to specific sequences of specific RNA species could be used) or family of RNA species in a sample.

In some embodiments, the 5'-DNA portion of a first primer includes the 5'-most nucleotide of the primer. In some embodiments, the 5'-RNA portion of a first primer includes the 5'-most nucleotide of the primer. In other embodiments, the 3'-DNA portion of a first primer includes the 3'-most nucleotide of the primer. In other embodiments, the 3'-RNA portion of a first primer includes the 3'-most nucleotide of the primer. In other embodiments, the 3'-DNA portion is adjacent to the 5'-RNA portion and includes the 3'-most nucleotide of the primer (and the 5'-RNA portion includes the 5'-most nucleotide of the primer).

Second Primer

The first primer extension product is used to generate additional DNA or RNA strands containing sequence related, either through homology or complementarity, to the original target RNA sequence. The primer extension product may be used as a single strand template. Alternatively, the primer extension product may be used as a double stranded template by creation of a second strand via use of a DNA-dependent DNA polymerase. In order to amplify the primer extension product, secondary primers may be used that bind to the primer extension product for use in the synthesis of the second cDNA strand, complementary to the cDNA. The second primer is complementary to the cDNA and comprises DNA, RNA fragments, tailed RNA/DNA, tailed DNA/DNA, or mixtures thereof. The second primer further comprises specific sequences, multiple sequences, or random sequences. Various embodiments of the second primer used in the methods of the invention are described herein. For the methods described herein, one or more second primers can be used.

In one embodiment, the second primer is an oligonucleotide that is supplied externally. The second primer in the methods of the invention (which primes generation of the second strand cDNA) comprises a sequence (which may or may not be the whole of the primer) that is hybridizable (under a given set of conditions) to a first strand cDNA at a site on the first strand cDNA such that the second strand cDNA would be homologous to the RNA sequence of interest. In another embodiment, the second primer is a primer comprising DNA (in some embodiments, consisting of DNA).

To achieve hybridization to a first strand cDNA (which, as is well known and understood in the art, depends on other factors such as, for example, ionic strength and temperature), the sequence of the second primer that is hybridizable to the first strand cDNA is preferably of at least about 60%, more preferably at least about 75%, even more preferably at least about 90%, and most preferably at least about 95% complementarity to the first strand cDNA. Generation of primers suitable for extension by polymerization is well known in the art.

In other embodiments, the second primer comprises one or more fragments of target RNA hybridized to the first primer extension product, said one or more fragments generated by cleaving RNA in the complex of target RNA and first primer extension product with an enzyme that cleaves RNA from an RNA/DNA heteroduplex. In some embodiments, this second primer comprises one or more fragments of the target RNA from cleavage due to heat, chemicals, and enzymes such as RNase. For example, the target RNA in the initial complex comprising the target RNA and first primer extension product is cleaved with an enzyme (such as RNaseH), or by heating the reaction mixture to cleave the RNA target, such that at least one fragment of the template RNA remains hybridized to the composite primer extension product. In this embodiment of the invention, one (or more) template RNA fragment(s) serves as a second primer in the manner described above, to generate a fragment extension product which has the same function as the second primer extension product in the amplification methods described above.

Suitable second primers and second primer RNA fragments in the methods of the invention are long enough such that it does not dissociate from the first strand cDNA, preferably from about 3 to about 30, more preferably from about 5 or 6 to about 25, even more preferably from about 10 to about 20, and most preferably from about 12 to about 20, nucleotides in length.

In yet another embodiment, the second primer is a random primer. In other embodiments, the second primer comprises a portion (for example, a 3' portion) that comprises a random sequence (i.e., a sequence designed to be hybridizable (under a given set of conditions) to one or more sequences in the sample). In some embodiments, the second primer comprises a 5' portion that is non-hybridizable to a first primer extension product (tailed primer). In some embodiments, the 5'-region of the second primer further comprises defined or universal sequences. In some embodiments, the second primer comprises only a sequence that is hybridizable to a first primer extension product (primer with no tail).

In embodiments involving transcription, the second primer may comprise propromoter sequence (also referred to herein as "propromoter polynucleotide") that is capable of hybridizing to displaced first strand cDNA. Hybridization of the propromoter polynucleotide to a displaced primer extension product and extension of the 3'-end of the displaced first primer extension product (if there is an overhang) results in a double stranded promoter region that drives transcription (via DNA-dependent RNA polymerase) to produce sense RNA products. This transcription approach is described herein and in Kurn et al., U.S. Pat. No. 6,251,639.

Promoter oligonucleotides of the present invention can also be modified to prevent the synthesis of DNA there from. In one embodiment, the promoter oligonucleotides comprise a blocking moiety attached at their 3'-termini to prevent primer extension in the presence of a polymerase. Indeed, according to the present invention, at least about 80% of the oligonucleotides present in the amplification reaction which comprise a promoter further comprise a 3'-blocking moiety. In further embodiments, at least about 85%, 90%, 95%, 96%, 97%, 98%, 99% or 100% of the oligonucleotides provided to the amplification reaction which comprise a promoter are further modified to comprise a 3'-blocking moiety. In a specific embodiment, any oligonucleotide used in an amplification reaction of the present invention which comprises a promoter sequence must further comprise a 3'-terminus blocking moiety.

In a preferred embodiment, the propromoter sequence is located in the 5'-portion of the oligonucleotide and the hybridizing sequence is located in the 3'-portion of the oligonucleotide. In one embodiment, and most typically, the promoter and hybridizing sequences are different sequences. In another embodiment, the promoter and hybridizing sequences overlap in sequence identity. In yet another embodiment, the promoter and hybridizing sequences are the same sequence, and thus are in the same location on the PTO. In the embodiments wherein hybridization of the PTO to the primer extension product results in a duplex comprising an overhang (the 5'-end of the PTO that does not hybridize to the displaced primer extension product, typically comprising all or part of the propromoter sequence), DNA polymerase fills in the overhang to create a double stranded promoter capable of effecting transcription by a suitable RNA polymerase.

In another embodiment, the PTO comprises a sequence that is 5' to the propromoter sequence, i.e., the PTO comprises additional nucleotides (which may or may not be transcriptional regulatory sequences) located 5' to the propromoter sequence. Generally, but not necessarily, the sequence is not hybridizable (under a given set of conditions) to the primer extension product.

Composite Amplification Primers

Composite amplification primers (or amplification composite primers) are RNA/DNA composite primers that can be used to create multiple copies of (amplify) a polynucleotide sequence isothermally using RNA cleavage, and DNA polymerase activity with strand displacement. Amplification with such primers is described, for example in U.S. Pat. Nos. 6,251,639, 6,692,918, and 6,946,251. The composite amplification primer comprises sequences capable of hybridizing to a portion of a DNA template, and most often comprises sequences hybridizable to a defined 3'-portion of the DNA.

A composite amplification primer comprises at least one RNA portion that is capable of (a) binding (hybridizing) to a sequence on a DNA template independent of hybridization of the DNA portion(s) to a sequence on the same extension product; and being cleaved with a ribonuclease when hybridized to the DNA template. The composite amplification primers bind to the DNA template to form a partial heteroduplex in which only the RNA portion of the primer is cleaved upon contact with a ribonuclease such as RNase H, while the DNA template remains intact, thus enabling annealing of another composite primer.

The composite amplification primers also comprise a 3'-DNA portion that is capable of hybridization to a sequence on the DNA template such that its hybridization to the DNA is favored over that of the nucleic acid strand that is displaced from the DNA template by the DNA polymerase. Such primers can be rationally designed based on well known factors that influence nucleic acid binding affinity, such as sequence length and/or identity, as well as hybridization conditions. In a preferred embodiment, hybridization of the 3'-DNA portion of the composite primer to its complementary sequence in the second strand cDNA is favored over the hybridization of the homologous sequence in the 5'-end of the displaced strand to the second strand cDNA.

DNA-dependent DNA Polymerase Inhibitors

The methods of the current invention inhibit formation of unwanted amplification products through the use of DNA-dependent DNA polymerase inhibitors during generation of the first primer extension product. DNA-dependent DNA polymerase inhibitors prevent enzymatic activity that generates primer extension products along DNA present in the sample with the target RNA. This method is a novel approach to amplification of polynucleotides of or DNA complementary to the target RNA in samples comprising, or which may comprise, DNA targets. Traditionally, target RNA would be purified from the DNA in the starting material (e.g. cell lysates), resulting in decreased quantity and quality of the RNA due to artifacts and losses introduced during the purification steps. Failure to isolate the RNA would result in random amplification of nucleic acid segments found in DNA as well as the RNA target or targets. The methods of the present invention allow for amplification of select RNA species, or the total RNA species, in the sample by combining the process of specifically reverse transcribing an RNA sequence in the presence of a DNA-dependent DNA polymerase inhibitor, removing the inhibitor, and allowing amplification of the uniquely marked cDNA, resulting in specific amplification of the target RNA sequences or of the sequences complementary to the target RNA sequence or sequences.

Furthermore, certain DNA-dependent DNA polymerase inhibitors are known to be effective in preventing other replication artifacts such as premature synthesis of the second strand cDNA and therefore allow amplification of only the first primer extension product. Actinomycin is an example of this type of DNA-dependent DNA polymerase inhibitor and is useful in the synthesis of single stranded first strand cDNA while inhibiting second strand synthesis.

There are several known DNA-dependent DNA polymerase inhibitors known in the art. For example, Actinomycin-D acts as a DNA-dependent DNA polymerase inhibitor by binding to DNA and preventing initiation of replication (Guy and Taylor (1978) PNAS 75:6088-92.) Other examples of DNA-dependent DNA polymerase inhibitors include, but are not limited to, actinomycin (dactinomycin), alpha-amanitin, aphidicolin (Cozad and Warner (1982) Gamete Research 6:155-60; Gonzcol and Plotkin (1985) Arch Virology 84:129-34; Haraguchi et al. (1983) Nucleic Acids Research 11:1197-1209), BPS, novobiocin (Schneck and Staudenbauer (1977) Nuc Acids Res 4:2057-64), rifampicin, rifamycin (Frolova et al. (1977) Nuc Acids Res 4:523-8), sulfoquinovosylmonoacylglycerol, sulfoquinovosyldiacylglycerol (Ohta et al. (2000) Mutat Res 467:139-52; Ohta et al. (1999) Biol Pharm Bull 22:111-16), ursane, oleanane triterpenoids, ursolic acid, oleanolic acid (Deng et al. (1999) J Nat Prod 62:1624-6), mikanolide, dihydromikanolide (U.S. Pat. No. 6,767,561), dehydroaltenusin (Mizushina et al. (2000) J Biol Chem 275: 33957-61), catapol (Pungitore et al. (2004) J Nat Prod 67:357-61), taxinine, cephalomanninine (Oshige et al. (2004) Bioorganic and Medicinal Chem 12:2597-601), dipeptide alcohols (Kato et al. (2005) Int J Mol Med 16:653-9), corylifolin; bakuchiol; resveratrol; Neobavaisoflavone; daidzein; bakuchicin (Sun et al. (1998) J Nat Prod 61:362-6), levodopa, dopamine (Wick (1980) Cancer Research 40:1414-8), anacardic acid and oleic acid (Chen et al. (1998) Chem Comm 24:2769-70).

The DNA-dependent DNA polymerase inhibitors of the present invention are added in an amount effective to inhibit DNA-dependent DNA polymerase activity. As a result, replication of DNA, when present in the sample in combination with RNA target or targets, is inhibited. The amount of a DNA-dependent DNA polymerase inhibitor that should be added to achieve the desired inhibition is well known and understood in the art. For example, the DNA-dependent DNA polymerase inhibitor Actinomycin D may be added in a concentration from about 0.1 μg/ml to about 100 μg/ml. In a preferred embodiment, 50% of DNA replication is inhibited by addition of a DNA-dependent DNA polymerase inhibitor. In another preferred embodiment, 60% of DNA replication is inhibited by addition of a DNA-dependent DNA polymerase inhibitor. In yet other preferred embodiments, 70%, 80%, 85%, 90%, 95%, 96%, 97%, 98%, 99% or 100% of DNA replication is inhibited by addition of a DNA-dependent DNA polymerase inhibitor.

Combinations of DNA-dependent DNA polymerase inhibitors may be used to achieve the desired inhibition. Use of combinations of DNA-dependent DNA polymerase inhibitors may be desirable to minimize unwanted effects on the reaction conditions by decreasing the concentration of each inhibitor in the reaction mixture. Alternatively, the combination of inhibitors may be able to achieve a greater amount of inhibition, such as by inhibiting DNA-dependent DNA polymerase activity at various stages.

It is known that several of these DNA-dependent DNA polymerase inhibitors also act to inhibit DNA-dependent RNA polymerase. Thus, by selecting the appropriate inhibitors, the methods of the present invention may also be useful for inhibiting transcription. This is especially useful in reaction mixtures that contain DNA-dependent RNA polymerases, such as extracts from whole cell lysates.

Following generation of a marked DNA sequence complementary to the target RNA, the DNA-dependent DNA polymerase inhibitor is removed from the reaction conditions or inhibited, inactivated, or sequestered from functioning to allow for the synthesis of a second strand cDNA and amplification of the primer extension product. Techniques for removal of a DNA-dependent DNA polymerase inhibitor from a reaction condition are well known in the art. In some cases, the RNA-dependent DNA polymerase is also removed. These methods include binding of the nucleic acid components in the reaction mixture to a solid surface such as beads, separating the solid surfaces and removing the soluble portion of the reaction mixture which comprises the DNA-dependent DNA polymerase inhibitor, resuspending the beads to recover the bound nucleic acid components, and proceeding with the cleaned reaction mixture as described herein. Bead separation may be carried out by, for example, centrifugation, magnetic separation of magnetic beads, and the like. Other solid surfaces which bind nucleic acid are also useful for carrying out the methods of the invention. DNA-dependent DNA polymerase inhibitors may be inhibited from functioning through binding of an inhibitor (e.g. an antibody directed to the DNA-dependent DNA polymerase inhibitor). In addition, inactivation of the inhibitor may be carried out by an enzyme. For example, enzymatic inactivation of actinomycin D has been described previously (see Hou and Perlman, JBC (1970), 245: 1289-1295).

Polynucleotide Comprising a Propromoter and a Region which Hybridizes to a Primer Extension Product Some embodiments involving amplification of an RNA sequence of interest, methods of the invention employ a propromoter polynucleotide comprising a propromoter and a region which hybridizes to a primer extension product. In some embodiments, the propromoter polynucleotide is provided as a PTO, as described in greater detail below.

Propromoter Template Oligonucleotide

In some embodiments, RNA amplification methods employ a promoter sequence, provided by a propromoter template oligonucleotide (PTO), for in-vitro transcription by DNA-dependent RNA polymerase (see U.S. Pat. Nos. 5,545, 522, 5,716,785, and PNAS (1990), 87: 1663-1667, each hereby incorporated in its entirety by reference).

A PTO for use in the methods and compositions of the invention is a single-stranded polynucleotide, generally DNA, comprising a propromoter sequence that is designed for formation of a double-stranded promoter of an RNA polymerase, and a portion capable of hybridizing to the 3'-end of a primer extension product. In an embodiment of the invention, the portion capable of hybridizing to the 3'-end of a primer extension product comprises a sequence which is hybridizable to a defined end sequence of the second primer extension product (and thus, subsequently the 3'-end of the single stranded DNA products). In another embodiment, the portion capable of hybridizing to the 3'-end of a primer extension product comprises a random sequence. In another embodiment, the portion capable of hybridizing to the 3'-end of a primer extension product comprises a sequence, which is hybridizable to sequences found at the 38-end of a multiplicity of first strand cDNAs.

Promoter sequences that allow transcription of a template DNA are known in the art and have been discussed above. Preferably, the promoter sequence is selected to provide optimal transcriptional activity of the particular RNA polymerase used. Criteria for such selection, i.e., a particular promoter sequence particularly favored by a particular RNA polymerase, is also known in the art. For example, the sequences of the promoters for transcription by T7 DNA dependent RNA polymerase and SP6 are known in the art. The promoter sequence can be from a prokaryotic or eukaryotic source.

In some embodiments, the PTO comprises an intervening sequence between a propromoter sequence and a portion capable of hybridizing to the 3'-end of the primer extension product. Suitable length of the intervening sequence can be empirically determined, and can be at least about 1, 2, 4, 6, 8, 10, 12, 15 nucleotides. Suitable sequence identity of the intervening sequence can also be empirically determined, and the sequence is designed to preferably, but not necessarily, enhance degree of amplification as compared to omission of the sequence. In one embodiment, the intervening sequence is a sequence that is designed to provide for enhanced, or more optimal, transcription by the RNA polymerase used. Generally, the sequence is not related (i.e., it does not substantially hybridize) to the target nucleic acid. More optimal transcription occurs when transcriptional activity of the polymerase from a promoter that is operatively linked to said sequence is greater than from a promoter that is not so linked. The sequence requirements for optimal transcription are generally known in the art as previously described for various DNA dependent RNA polymerases, such as in U.S. Pat. Nos. 5,766,849 and 5,654,142, and can also be empirically determined.

In one embodiment, the PTO cannot function efficiently as a primer for nucleic acid extension. Techniques for blocking the primer function of the PTO include any that prevent addition of nucleotides to the 3'-end of the PTO by a DNA polymerase. Such techniques are known in the art, including, for example, substitution or modification of the 3'-hydroxyl group, or incorporation of a modified nucleotide, such as a dideoxynucleotide, in the 3'-most position of the PTO that is not capable of anchoring addition of nucleotides by a DNA polymerase. It is possible to block the 3'-end using a label, or a small molecule which is a member of a specific binding pair, such as biotin. It is also possible to render the 3'-end non-extendable by addition of nucleotides which cannot hybridize to a primer extension product, either due to non-complementarity or due to structural modifications which do not support hydrogen bonding. In other embodiments, the PTO is not blocked.

The length of the portion of the PTO that hybridizes to a primer extension product of interest is preferably from about 5 to about 50 nucleotides, more preferably from about 10 to about 40 nucleotides, even more preferably from about 15 to about 35 nucleotides, and most preferably from about 20 to 30 nucleotides. In some embodiments, the hybridizing portion is at least about any of the following: 3, 5, 10, 15, 20; and less than about any of the following: 30, 40, 50, 60. The complementarity of the hybridizing portion is preferably at least about 25%, more preferably at least about 50%, even more preferably at least about 75%, and most preferably at least about 90%, to its intended binding sequence on the primer extension product of interest.

DNA Polymerase, an Agent Capable of Cleaving an RNA-DNA Heteroduplex, and RNA Polymerase for SPIA The isothermal amplification methods of the invention employ the following enzymes: an RNA-dependent DNA polymerase, a DNA-dependent DNA polymerase, and an agent capable of cleaving a RNA strand of a RNA/DNA heteroduplex (for example, a ribonuclease such as RNase H). Some examples of the enzymes which may be used in the methods and compositions are described herein. One or more of these activities may be found and used in a single enzyme. For example, RNase H activity may be supplied by an RNA-dependent DNA polymerase (such as reverse transcriptase) or may be provided in a separate enzyme. Similarly, a DNA polymerase may comprise both RNA-dependent and DNA-dependent DNA polymerase enzyme activities, or separate enzymes may be used. A DNA-dependent DNA polymerase and an enzyme that cleaves RNA may also be the same enzyme. A DNA-dependent DNA polymerase, an RNA-dependent DNA polymerase, and the enzyme that cleaves RNA can also be the same enzyme. Another RNase useful for carrying out the methods of the invention is RNase I, which cleaves single-stranded RNA.

Reverse transcriptases useful for this method may or may not have RNase H activity. The selective RNase may be provided as an RNase H activity of a reverse transcriptase, or may be provided as a separate enzyme, e.g., as an *E. coli* RNase H or a *T. thermophilus* RNase H, or derivatives thereof. Other enzymes which selectively degrade RNA present in an RNA:DNA duplex may also be used. Many reverse transcriptases, such as those from avian myeloblastosis virus (AMV-RT), and Moloney murine leukemia virus (MMLV-RT) comprise more than one activity (for example, polymerase activity and ribonuclease activity) and can function in the formation of the double stranded cDNA molecules. However, in some instances, it is preferable to employ a reverse transcriptase which lacks or has reduced levels RNase H activity. Reverse transcriptases devoid of RNase H or with reduced levels of RNase H activity are known in the art, including those comprising a mutation of the wild type reverse transcriptase where the mutation eliminates the RNase H activity. In these cases, the addition of an RNase H from other sources, such as that isolated from *E. coli*, can be employed for the formation of the double stranded cDNA. The RNA-dependent DNA polymerase activity and DNA-dependent DNA polymerase activity may be provided by the same enzyme (for example, Bst polymerase), or these activities may be provided in separate enzymes. DNA polymerases with strand displacement activity are also useful.

Enzymes for use in the compositions, methods and kits of the present invention include any enzyme having reverse transcriptase activity. Such enzymes include, but are not limited to, retroviral reverse transcriptase, retrotransposon reverse transcriptase, hepatitis B reverse transcriptase, cauliflower mosaic virus reverse transcriptase, bacterial reverse transcriptase, *E. coli* DNA polymerase and klenow fragment, Tth DNA polymerase, Taq DNA polymerase (Saiki, R. K., et al., Science 239:487-491 (1988); U.S. Pat. Nos. 4,889,818 and 4,965,188), Tne DNA polymerase (WO 96/10640), Tma DNA polymerase (U.S. Pat. No. 5,374,553), C. Therm DNA polymerase from *Carboxydothermus hydrogenoformans* (EP0921196A1, Roche, Pleasanton, Calif., Cat. No. 2016338), ThermoScript (Invitrogen, Carlsbad, Calif. Cat. No. 11731-015) and mutants, fragments, variants or derivatives thereof. As will be understood by one of ordinary skill in the art, modified reverse transcriptases may be obtained by recombinant or genetic engineering techniques that are routine and well-known in the art. Mutant reverse transcriptases can, for example, be obtained by mutating the gene or genes encoding the reverse transcriptase of interest by site-directed or random mutagenesis. Such mutations may include point mutations, deletion mutations and insertional mutations. Preferably, one or more point mutations (e.g., substitution of one or more amino acids with one or more different amino acids) are used to construct mutant reverse transcriptases of the invention. Fragments of reverse transcriptases may be obtained by deletion mutation by recombinant techniques that are routine and well-known in the art, or by enzymatic digestion of the reverse transcriptase(s) of interest using any of a number of well-known proteolytic enzymes. Mutant DNA polymerase containing reverse transcriptase activity can also be used as described in U.S. patent application Ser. No. 10/435,766, incorporated by reference in its entirety.

One aspect of the invention is the formation of a complex comprising an RNA/DNA partial heteroduplex. This process generally utilizes the enzymatic activities of an RNA-dependent DNA polymerase, and a DNA-dependent DNA polymerase. Generally, RNA in the RNA/DNA partial heteroduplex is cleaved by an agent (such as an enzyme, such as a ribonuclease) capable of cleaving RNA from an RNA/DNA hybrid, generating a 3'-single stranded portion with sequences that are complementary to RNA in a composite primer (and thus forming a binding site for a composite primer). The DNA primer extension product may also be separated (at least partially) from the RNA template using an enzyme which degrades the RNA template. Suitable enzymes, i.e., "selective RNAses," are those which act on the RNA strand of an RNA:DNA complex, and include enzymes which comprise an RNase H activity.

RNA-dependent DNA polymerases for use in the methods and compositions of the invention are capable of effecting extension of a primer according to the methods of the invention. Accordingly, a preferred RNA-dependent DNA polymerase is one that is capable of extending a nucleic acid primer along a nucleic acid template that is comprised at least predominantly of ribonucleotides. Suitable RNA-dependent DNA polymerases for use in the methods and compositions of the invention include reverse transcriptase and, for example, a DNA polymerase that possesses both DNA-dependent and RNA-dependent DNA polymerase activity, such as Bst DNA polymerase. The RNA-dependent DNA polymerase may comprise a RNase H enzyme activity, or separate enzymes may be used.

DNA-dependent DNA polymerases for use in the methods and compositions of the invention are capable of effecting extension of the composite primer according to the methods of the invention. Accordingly, a preferred polymerase is one that is capable of extending a nucleic acid primer along a nucleic acid template that is comprised at least predominantly of deoxynucleotides. The formation of the complex comprising the RNA/DNA partial heteroduplex can be carried out by a DNA polymerase which comprises both RNA-dependent DNA polymerase and DNA-dependent DNA polymerase activities (such as Bst DNA polymerase, or a reverse transcriptase). In one embodiment amplification of an RNA sequence according to methods of the invention involves the use of a DNA polymerase that is able to displace a nucleic acid strand from the polynucleotide to which the displaced strand is bound, and, generally, the more strand displacement capability the polymerase exhibits (i.e., compared to other polymerases which do not have as much strand displacement capability) is preferable. Preferably, the DNA polymerase has high affinity for binding at the 3'-end of an oligonucleotide hybridized to a nucleic acid strand. Preferably, the DNA polymerase does not possess substantial nicking activity. Generally, the DNA polymerase preferably has little or no 5' to 3' exonuclease activity so as to minimize degradation of primer, or primer extension products. Generally, this exonuclease activity is dependent on factors such as pH, salt concentration, whether the template is double stranded or single stranded, and so forth, all of which are familiar to one skilled in the art. Mutant DNA polymerases in which the 5' to 3' exonuclease activity has been deleted, are known in the art and are suitable for the amplification methods described herein. Mutant DNA polymerases which lack both 5' to 3' nuclease and 3' to 5' nuclease activities have also been described, for example, exo$^{-/-}$-Klenow DNA polymerase. It is preferred that the DNA polymerase displaces primer extension products from the template nucleic acid in at least about 25%, more preferably at least about 50%, even more preferably at least about 75%, and most preferably at least about 90%, of the incidence of contact between the polymerase and the 5' end of the primer extension product. In some embodiments, the use of thermostable DNA polymerases with strand displacement activity is preferred. Such polymerases are known in the art, such as described in U.S. Pat. No. 5,744,312 (and references cited therein). Generally, the DNA polymerase has little to no proofreading activity Suitable DNA polymerases for use in the methods and compositions of the invention include those disclosed in U.S. Pat. Nos. 5,648,211 and 5,744,312, which include exo⁻ Vent (New England Biolabs), exo⁻ Deep Vent (New England Biolabs), Bst (BioRad), exo⁻ Pfu (Stratagene), Bca (Panvera), sequencing grade Taq (Promega), exo$^{-/-}$ Klenow DNA polymerase, and thermostable DNA polymerases from *thermoanaerobacter thermohydrosulfuricus*.

One of the ribonuclease for use in the methods and compositions of the invention is capable of cleaving ribonucleotides in an RNA/DNA hybrid or heteroduplex. Preferably, the ribonuclease cleaves ribonucleotides in an RNA/DNA heteroduplex regardless of the identity and type of nucleotides adjacent to the ribonucleotide to be cleaved. It is preferred that the ribonuclease cleaves independent of sequence identity. Examples of suitable ribonucleases for the methods and compositions of the invention are well known in the art, including ribonuclease H (RNase H), e.g., Hybridase.

As is well known in the art, DNA-dependent DNA polymerase activity, RNA-dependent DNA polymerase activity, and the ability to cleave RNA from a RNA/DNA heteroduplex may be present in different enzymes, or two or more activities may be present in the same enzyme. Accordingly, in some embodiments, the same enzyme comprises RNA-dependent DNA polymerase activity and cleaves RNA from an RNA/DNA heteroduplex. In some embodiments, the same enzyme comprises DNA-dependent DNA polymerase activity and cleaves RNA from an RNA/DNA heteroduplex. In some embodiments, the same enzyme comprises DNA-dependent DNA polymerase activity, RNA-dependent DNA polymerase activity and cleaves RNA from an RNA/DNA heteroduplex. In some embodiments, different enzymes comprise RNA-dependent DNA polymerase activity and DNA-dependent DNA polymerase activity. In some embodiments, different enzymes comprise RNA-dependent DNA polymerase activity and cleave RNA from an RNA/DNA heteroduplex. In some embodiments, different enzymes comprise DNA-dependent DNA polymerase activity and cleave RNA from an RNA/DNA heteroduplex. In other embodiments the RNA targets are degraded by the use of other RNases such as RNase 1, for example, for removing the target RNA following extension of all DNA first primer along the RNA targets by transcription, or a combination of RNase H and other RNases.

The DNA-dependent RNA polymerases for use in the methods and compositions of the invention are known in the art. Either eukaryotic or prokaryotic polymerases may be used. Examples include T7, T3 and SP6 RNA polymerases. Generally, the RNA polymerase selected is capable of transcribing from the promoter sequence provided by the propromoter polynucleotides as described herein. Generally, the RNA polymerase is a DNA-dependent polymerase, which is preferably capable of transcribing from a single stranded DNA template so long as the promoter region is double stranded.

In general, the enzymes used in the methods and compositions of the invention should not produce substantial degradation of the nucleic acid components of said methods and compositions.

Reaction Conditions and Detection

Appropriate reaction media and conditions for carrying out the methods of the invention are those that permit nucleic acid amplification according to the methods of the invention. Such media and conditions are known to persons of skill in the art, and are described in various publications, such as U.S. Pat. Nos. 5,554,516; 5,716,785; 5,130,238; 5,194,370; 6,090,591; 5,409,818; 5,554,517; 5,169,766; 5,480,784; 5,399,491; 5,679,512; and PCT Pub. No. WO 99/42618. For example, a buffer may be Tris buffer, although other buffers can also be used as long as the buffer components are non-inhibitory to enzyme components of the methods of the invention. The pH is preferably from about 5 to about 11, more preferably from about 6 to about 10, even more preferably from about 7 to about 9, and most preferably from about 7.5 to about 8.5. The reaction medium can also include bivalent metal ions such as $Mg^{2+}$ or $Mn^{2+}$, at a final concentration of free ions that is within the range of from about 0.01 to about 15 mM, and most preferably from about 1 to 10 mM. The reaction medium can also include other salts, such as KCl or NaCl, that contribute to the total ionic strength of the medium. For example, the range of a salt such as KCl is preferably from about 0 to about 125 mM, more preferably from about 0 to about 100 mM, and most preferably from about 0 to about 75 mM. The reaction medium can further include additives that could affect performance of the amplification reactions, but that are not integral to the activity of the enzyme components of the methods. Such additives include proteins such as BSA, single strand binding proteins (for e.g., T4 gene 32 protein), and non-ionic detergents such as NP40 or Triton. Reagents, such as DTT, that are capable of maintaining enzyme activities can also be included. Such reagents are known in the art. Where appropriate, an RNase inhibitor (such as RNasin) that does not inhibit the activity of the RNase employed in the method can also be included. Any aspect of the methods of the invention can occur at the same or varying temperatures. Preferably, the amplification reactions (particularly, primer extension other than the first and second strand cDNA synthesis steps, and strand displacement) are performed isothermally, which avoids the cumbersome thermocycling process. The amplification reaction is carried out at a temperature that permits hybridization of the oligonucleotides (primer and/or PTO) of the invention to the template polynucleotide and primer extension products, and that does not substantially inhibit the activity of the enzymes employed. The temperature can be in the range of preferably about 25° C. to about 85° C., more preferably about 30° C. to about 80° C., and most preferably about 37° C. to about 75° C. In some embodiments that include RNA transcription, the temperature for the transcription steps is lower than the temperature(s) for the preceding steps. In these embodiments, the temperature of the transcription steps can be in the range of preferably about 25° C. to about 85° C., more preferably about 30° C. to about 75° C., and most preferably about 37° C. to about 70° C.

Nucleotide and/or nucleotide analogs, such as deoxyribonucleoside triphosphates, that can be employed for synthesis of the primer extension products in the methods of the invention are provided in the amount of from preferably about 50 to about 2500 µM, more preferably about 100 to about 2000 µM, even more preferably about 200 to about 1700 µM, and most preferably about 250 to about 1500 µM. In some embodiments, a nucleotide or nucleotide analog whose presence in the primer extension strand enhances displacement of the strand (for example, by causing base pairing that is weaker than conventional AT, CG base pairing) is included. Such nucleotide or nucleotide analogs include deoxyinosine and other modified bases, all of which are known in the art. Nucleotides and/or analogs, such as ribonucleoside triphosphates, that can be employed for synthesis of the RNA transcripts in the methods of the invention are provided in the amount of from preferably about 0.25 to about 6 mM, more preferably about 0.5 to about 5 mM, even more preferably about 0.75 to about 4 mM, and most preferably about 1 to about 3 mM.

The oligonucleotide components of the amplification reactions of the invention are generally in excess of the number of target nucleic acid sequence to be amplified. They can be provided at about or at least about any of the following: 10, $10^2$, $10^4$, $10^6$, $10^8$, $10^{10}$, $10^{12}$ times the amount of target nucleic acid. Composite primers and PTO can each be provided at about or at least about any of the following concentrations: 50 nM, 100 nM, 500 nM, 1000 nM, 2500 nM, 5000 nM.

In the methods of the invention, the steps may be carried out in the order listed or, in some cases, may be carried out in a different order. In some methods a later step depends on the formation of a product from an earlier step, in which case such steps must be carried out in the order listed. One of ordinary skill in the art will understand which steps should be carried out in the order listed, and which steps can be carried out in a different order.

In some embodiment, the foregoing components are added simultaneously at the initiation of the amplification process. In another embodiment, components are added in any order prior to or after appropriate time points during the amplification process, as required and/or permitted by the amplification reaction. Such time points, some of which are noted below, can be readily identified by a person of skill in the art. The enzymes used for nucleic acid amplification according to the methods of the invention can be added to the reaction mixture either prior to the target nucleic acid denaturation step, following the denaturation step, or following hybridization of the primer to the target RNA, as determined by their thermal stability and/or other considerations known to the person of skill in the art. The first strand cDNA (first primer extension product) and the second strand cDNA (second primer extension product) synthesis reactions can be performed consecutively, followed by the amplification steps (binding by another primer, primer extension and strand displacement). In these embodiments, the reaction conditions and components may be varied between the different reactions.

In some embodiments, the amplification process can be stopped at various time points, and resumed at a later time. Said time points can be readily identified by a person of skill in the art. One time point is at the end of first strand cDNA synthesis. Another time point is at the end of second strand cDNA synthesis. Methods for stopping the reactions are known in the art, including, for example, cooling the reaction mixture to a temperature that inhibits enzyme activity or heating the reaction mixture to a temperature that destroys an enzyme. Methods for resuming the reactions are also known in the art, including, for example, raising the temperature of the reaction mixture to a temperature that permits enzyme activity or replenishing a destroyed (depleted) enzyme. In some embodiments, one or more of the components of the reactions is replenished prior to, at, or following the resumption of the reactions. For example, it may be necessary to replenish the composite primer prior to beginning the linear amplification reaction if the same composite primer is being used. Alternatively, the reaction can be allowed to proceed (i.e., from start to finish) without interruption.

In some embodiments the reaction can be allowed to proceed without purification of intermediate complexes, for example, to remove primer. Products can be purified at various time points, which can be readily identified by a person of skill in the art. One time point is at the end of first strand cDNA synthesis. Another time point is at the end of second strand cDNA synthesis. In some embodiments, the removal of primers and/or target at the end of a defined step by enzymes with appropriate nuclease activities are also useful, for example, cleavage of the RNA portion of free composite tailed primer prior to the isothermal amplification step by treatment with RNase 1. In some embodiment, routine purification of the complex of first and second cDNA results in slightly higher amplification efficiency in subsequent linear amplification steps.

The detection of the amplification product is indicative of the presence of the target sequence. Quantitative analysis is also feasible. Direct and indirect detection methods (including quantitation) are well known in the art. For example, by comparing the amount of product amplified from a test sample containing an unknown amount of a polynucleotide containing a target sequence to the product of amplification of a reference sample that has a known quantity of a polynucleotide that contains the target sequence, the amount of target sequence in the test sample can be determined. The amplification methods of the invention can also be extended to analysis of sequence alterations and sequencing of the target nucleic acid. Further, detection could be effected by, for example, examination of translation products from RNA amplification products. The global amplification by the methods of the invention and/or the amplification of selected targets, when present in the sample, are useful for various methods which enable highly parallel nucleic acid interrogations.

Uses of the Invention

The invention provides methods and compositions to selectively amplify RNA in the presence of DNA. The amplification products from this invention can be used for a variety of purposes including, but not limited to, those described herein. For example, purposes using the amplification products of the invention include methods of sequencing, quantitating, or detecting a specific transcript or group of transcripts, genotyping (such as nucleic acid mutation detection, determining the presence or absence of a sequence of interest, analyzing splice variants), preparing an immobilized nucleic acid (which can be a nucleic acid immobilized on a microarray, a surface, a bead, or one or more wells in a plate), and characterizing nucleic acids using methods such as probe hybridization (Southern and Northern blotting, hybridization to probe arrays). The analysis of cellular RNA can be used in methods including gene expression profiling, Q-PCR, digital PCR, SAGE, methods of subtractive hybridization and the preparation of probes for subtractive hybridization, and methods of preparing libraries (which can be cDNA and/or differential hybridization libraries). Amplification products generated may also be further manipulated to generate labeled targets (with or without fragmentation) for analysis using microarrays and the like. Amplification products generated may also be used for analysis by sequencing. In some cases, sequencing may be performed by massively parallel sequencing methods including but not limited to nanopore sequencing, and massively parallel sequencing by various commercial platforms such as a Genome Sequencer from 454/Roche, the SOLiD system from Applied Biosystems, the Polonator by Dover Systems, the Helicos Genetic Analysis Platform by Helicos Biosciences, the Genome Analyzer by Illumina, and Single-Molecule Realtime (SMRT) technology from Pacific Biosystems.

The invention allows selective RNA amplification from a sample comprising total nucleic acids (i.e. DNA and RNA), thereby providing a means for amplification and analysis, detection, and quantification of target RNA sequences directly from cell or sample lysate without purification of the RNA targets. The sample may be from the same cells or tissues or from a combination of cells and other nucleic acid components, or other biological samples such as environmental samples. For example, samples may include viral RNA in a host sample, viral RNA in an environmental sample, or cell-free nucleic acids such as in blood or other bodily fluids. The samples may be single cell samples, samples of a few cells, or samples with small numbers of cells, for example 10s to hundreds of cells. The methods could be used, for example for performing gene expression analysis on single to small numbers of cells using the cell lysate directly as the sample with little or no further purification. In some cases the cell lysate could be treated to remove or denature all enzymes and/or proteins in the sample resulting in a total nucleic acid sample that can be used directly for the methods described herein.

The amplification methods of the invention are useful, for example, for pre-amplification and target preparation for analysis such as for example sequencing, Q-PCR, digital PCR, SAGE, or massively parallel analysis such as massively parallel sequencing, high density PCR arrays, microarray hybridization, and massively parallel Q-PCR of an RNA sequence or set of RNA sequences of interest. The sequencing process is carried out by amplifying a target RNA containing the sequence of interest by any of the methods described herein. Addition of nucleotides during primer extension is analyzed using methods known in the art, for example, incorporation of a terminator nucleotide or sequencing by synthesis (e.g. pyrosequencing). For sequencing methods based on methods described herein wherein the amplified product is DNA, the appropriate dNTPs, or analogs thereof, which may be labeled or unlabeled, are used. For sequencing methods based on methods described herein wherein the amplified product is RNA, the appropriate rNTPs, or analogs thereof, which may be labeled or unlabeled, may be used. Analysis of the reaction products for elucidation of sequence information can be carried out using any of various methods known in the art for sequencing.

In some embodiments, the methods are useful for pre-amplification and/or preparing target polynucleotide(s) for sequencing by synthesis using the methods commercialized by 454/Roche Lifesciences including but not limited to the methods and apparatus described in Margulies et al., Nature (2005) 437:376-380 (2005); and U.S. Pat. Nos. 7,244,559; 7,335,762; 7,211,390; 7,244,567; 7,264,929; 7,323,305. In general, target polynucleotides may be amplified by the methods of the present invention, immobilized onto beads, and compartmentalized in a water-in-oil PCR emulsion. In some cases, alternative amplification methods may be employed in the water-in-oil emulsion such as any of the methods provided herein. When the emulsion is broken, amplified fragments remain bound to the beads. The beads may be enriched and loaded into wells of a fiber optic slide so that there is approximately 1 bead in each well. Nucleotides are flowed across and into the wells in a fixed order in the presence of polymerase, sulfhydrolase, and luciferase. Addition of nucleotides complementary to the target strand results in a chemiluminescent signal that is recorded such as by a camera. The combination of signal intensity and positional information generated across the plate allows software to determine the DNA sequence.

In some embodiments, the methods are useful for pre-amplification and/or preparing target polynucleotide(s) for sequencing by the methods commercialized by Helicos BioSciences Corporation (Cambridge, Mass.) as described in U.S. application Ser. No. 11/167,046, and U.S. Pat. Nos. 7,501,245; 7,491,498; 7,276,720; and in U.S. Patent Application Publication Nos. US20090061439; US20080087826; US20060286566; US20060024711; US20060024678; US20080213770; and US20080103058. In general, target polynucleotides may be amplified by the methods of the present invention, and then immobilized onto a flow-cell surface. Polymerase and labeled nucleotides are then flowed over the immobilized DNA. After fluorescently labeled nucleotides are incorporated into the DNA strands by a DNA polymerase, the surface is illuminated with a laser, and an image is captured and processed to record single molecule incorporation events to produce sequence data.

In some embodiments, the methods are useful for pre-amplification and/or preparing target polynucleotide(s) for sequencing by the sequencing by ligation methods commercialized by Applied Biosystems (e.g. SOLiD sequencing). In general, target polynucleotides may be amplified by the methods of the present invention, and then incorporated into a water in oil emulsion along with polystyrene beads and amplified by for example PCR. In some cases, alternative amplification methods may be employed in the water-in-oil emulsion such as any of the methods provided herein. The amplified product in each water microdroplet formed by the emulsion interact, bind, or hybridize with the one or more beads present in that microdroplet leading to beads with a plurality of amplified products of substantially one sequence. When the emulsion is broken, the beads float to the top of the sample and are placed onto an array. Sequencing primers are then added along with a mixture of four different fluorescently labeled oligonucleotide probes. The probes bind specifically to the two bases in the polynucleotide to be sequenced immediately adjacent and 3' of the sequencing primer to determine which of the four bases are at those positions. After washing and reading the fluorescence signal form the first incorporated probe, a ligase is added. The ligase cleaves the oligonucleotide probe between the fifth and sixth bases, removing the fluorescent dye from the polynucleotide to be sequenced. The whole process is repeated using a different sequence primer, until all of the intervening positions in the sequence are imaged. The process allows the simultaneous reading of millions of DNA fragments in a 'massively parallel' manner. This 'sequence-by-ligation' technique uses probes that encode for two bases rather than just one allowing error recognition by signal mismatching, leading to increased base determination accuracy.

In some embodiments, the methods are useful for pre-amplification and/or preparing target polynucleotide(s) for sequencing by the sequencing by ligation methods commercialized by Dover Systems. Generally, target polynucleotides may be pre-amplified and/or prepared by the methods of the present invention. The target polynucleotides may then amplified in an emulsion in the presence of magnetic beads. Any amplification methods may be employed in the water-in-oil emulsion such as any of the methods provided herein. The resulting beads with immobilized clonal polynucleotide polonies are then purified by magnetic separation, capped, amine functionalized, and covalently immobilized in a series of flow cells. Then, a series of anchor primers are flowed through the cells, where they hybridize to the synthetic oligonucleotide sequences at the 3' or 5' end of proximal or distal genomic DNA tags. Once an anchor primer is hybridized, a mixture of fully degenerate nonanucleotides ('nonamers') and T4 DNA ligase is flowed into the cell; each of the nonamer mixture's four components being labeled with one of four fluorophores, which correspond to the base type at the query position. The fluorophore-tagged nonamers selectively ligate onto the anchor primer, providing a fluorescent signal that identifies the corresponding base on the genomic DNA tag. Once the probes are ligated, fluorescently labeling the beads, the array is imaged in four colors. Each bead on the array will fluoresce in only one of the four images, indicating whether there is an A, C, G, or T at the position being queried. After imaging, the array of annealed primer-fluorescent probe complex, as well as residual enzyme, are chemically striped using guanidine HCl and sodium hydroxide. After each cycle of base reads at a given position have been completed, and the primer-fluorescent probe complex has been stripped, the anchor primer is replaced, and a new mixture of fluorescently tagged nonamers is introduced, for which the query position is shifted one base further into the genomic DNA tag. Seven bases are queried in this fashion, with the sequence performed from the 5' end of the proximal tag, followed by six base reads with a different anchor primer from the 3' end of the proximal tag, for a total of 13 base pair reads for this tag. This sequence is then repeated for the 5' and 3' ends of the distal tag, resulting in another 13 base pair reads. The ultimate result is a read length of 26 bases (thirteen from each of the paired tags).

In some embodiments, the methods are useful for pre-amplification and/or preparing target polynucleotide(s) for sequencing by the methods commercialized by Illumina as described U.S. Pat. Nos. 5,750,341; 6,306,597; and 5,969,119. In general, target polynucleotides may be pre-amplified and/or prepared by the methods of the present invention to produce amplified nucleic acid sequences tagged at one (e.g. (A)/(A') or both ends (e.g. (A)/(A') and (C)/(C')). In some cases, single stranded nucleic acid tagged at one or both ends is amplified by the methods of the present invention (e.g. by SPIA or linear PCR). The resulting nucleic acid is then denatured and the single stranded amplified polynucleotides are randomly attached to the inside surface of flow-cell channels. Unlabeled nucleotides are added to initiate solid-phase bridge amplification to produce dense clusters of double-stranded DNA. The initiate the first base sequencing cycle, four labeled reversible terminators, primers, and DNA polymerase are added. After laser excitation, florescence form each cluster on the flow cell is imaged. The identity of the first base for each cluster is then recorded. Cycles of sequencing are performed to determine the fragment sequence one base at a time. For paired-end sequencing, such as for example, when the polynucleotides are labeled at both ends by the methods of the present invention, sequencing templates can be regenerated in-situ so that the opposite end of the fragment can also be sequenced.

In some embodiments, the methods are useful for pre-amplification and/or preparing target polynucleotide(s) for sequencing by the methods commercialized by Pacific Biosciences as described in U.S. Pat. Nos. 7,462,452; 7,476,504; 7,405,281; 7,170,050; 7,462,468; 7,476,503; 7,315,019; 7,302,146; 7,313,308; and US Application Publication Nos. US20090029385; US20090068655; US20090024331; and US20080206764. In general, target polynucleotides may be pre-amplified and/or prepared by the methods of the present invention. The amplified polynucleotides may then be immobilized in zero mode waveguide arrays. Polymerase and labeled nucleotides are added in a reaction mixture, and nucleotide incorporations are visualized via fluorescent labels attached to the terminal phosphate groups of the nucleotides. The fluorescent labels are clipped off as part of the nucleotide incorporation. In some cases, circular templates are utilized to enable multiple reads on a single molecule.

The DNA or RNA amplification products generated according to the methods of the invention are also suitable for analysis for the detection of any alteration (interchangeably called "mutations") in the target nucleic acid sequence, as compared to a reference nucleic acid sequence which is identical to the target nucleic acid sequence other than the sequence alteration. The sequence alterations may be sequence alterations present in the genomic sequence or may be sequence alterations which are not reflected in the genomic DNA sequences, for example, alterations due to post transcriptional alterations, and/or mRNA processing, including splice variants. Sequence alterations include deletion, substitution, insertion and/or transversion of one or more nucleotide.

The invention provides methods to characterize (for example, detect presence or absence of and/or quantify) an RNA sequence of interest by generating DNA or RNA products using amplification methods of the invention, and analyzing the products by detection/quantification methods such as those based on array technologies or solution phase technologies or combinations thereof. These amplified products may be labeled or unlabeled. The detection and/or quantitation of specific nucleic acid sequences is an important technique for identifying and classifying microorganisms, diagnosing infectious diseases, detecting and characterizing genetic abnormalities, identifying genetic changes associated with cancer, studying genetic susceptibility to disease, and measuring response to various types of treatment. Such procedures are also useful in detecting and quantitating microorganisms in foodstuffs, water, industrial and environmental samples, seed stocks, and other types of material where the presence of specific microorganisms may need to be monitored. Other applications are found in the forensic sciences, anthropology, archaeology, and biology where measurement of the relatedness of nucleic acid sequences has been used to identify criminal suspects, resolve paternity disputes, construct genealogical and phylogenetic trees, and aid in classifying a variety of life forms.

A number of methods to detect and/or quantitate nucleic acid sequences are well known in the art. These include hybridization to a labeled probe, and various permutations of the polymerase chain reaction (PCR), coupled with hybridization to a labeled probe (For example, see U.S. Pat. Nos. 4,683,195; 4,683,202; 4,800,159; Mullis et al., Meth. Enzymol. (1987) 155: 335-350; and Murakawa et al., DNA (1988) 7:287-295).

Various methods for the detection and quantification of gene expression levels have been developed in recent years. For example, microarrays, in which either defined cDNAs or oligonucleotides are immobilized at discrete locations on, for example, solid or semi-solid substrates, or on defined particles, enable the detection and/or quantification of the expression of a multitude of genes in a given specimen.

The amplification methods of the invention are also suitable for use in determining the levels of gene expression in a sample since the methods described herein are capable of amplifying one or a plurality of target RNAs in the same sample. As described above, amplification products can be detected and quantified by various methods, as described herein and/or known in the art. Since RNA is a product of gene expression, the levels of the various RNA species, such as mRNAs, in a sample is indicative of the relative expression levels of the various genes (gene expression profile). Thus, determination of the amount of target RNA present in a sample, as determined by quantifying amplification products of the sequences, provides for determination of the gene expression profile of the sample source.

The single-stranded DNA and RNA products of the methods of the invention are useful in preparing libraries, including cDNA libraries and subtractive hybridization libraries. Using the methods of the invention, libraries may be prepared from limited amount of starting material, for example, mRNA extracted from limited amount of tissue or even single cells. Accordingly, in one aspect, the methods of the invention provide preparing a library from the single stranded DNA or RNA products of the invention. In another aspect, the invention provides methods of preparing a library from the double stranded cDNA produced by the methods of the invention comprising two composite primers. Methods for preparing libraries from double stranded cDNA are well known in the art. In still another aspect, the invention provides methods for making a library, said method comprising the preparation of subtractive hybridization probes using any of the methods described herein.

The methods of the invention offer the ability to efficiently amplify mRNA in the presence of DNA under conditions that provide for high specificity of target amplification and which is generally reflective of the distribution in the input RNA. Thus, the utility of the detection/quantification methods which can be used with the amplification products of the invention, such as those based on the powerful array technology, real time PCR, quantitative TaqMan, quantitative PCR using molecular beacons and the like, should be greatly enhanced.

Compositions and Kits of the Invention

The invention also provides compositions and kits used in the methods described herein and may be incorporated as parts of kits, e.g., diagnostic kits for clinical or criminal laboratories, or nucleic amplification kits for general laboratory use. The present invention thus includes kits which include some or all of the reagents necessary to carry out the methods of the present invention, e.g., sample preparation reagents, oligonucleotides, binding molecules, stock solutions, nucleotides, polymerase inhibitors, enzymes, positive and negative control target sequences, test tubes or plates, labeling reagents, fragmentation reagents, detection reagents, purification matrices, and an instruction manual.

The compositions of the invention may be any or any combination of component(s), reaction mixture, and/or intermediate described herein. For example, the invention provides a composition comprising a first primer, reverse transcriptase, and one or more types of DNA-dependent DNA polymerase inhibitors, and combinations thereof. The invention also provides compositions comprising the amplification products described herein. Accordingly, the invention provides a population of DNA or RNA molecules which are copies or the complement of a target sequence, which are produced by any of the methods described herein. The compositions are generally in a suitable medium, although they can be in lyophilized form. Suitable media include, but are not limited to, aqueous media, such as pure water or buffers.

In another aspect, the invention provides a population of sense polynucleotide (e.g., DNA) molecules and antisense polynucleotide (e.g., DNA) molecules which are copies and complements of a target sequence, which are produced by any of the methods described herein. The invention also includes compositions and various configurations (such as arrays) of these populations, which may be homogeneous (same sequence) or heterogeneous (different sequence). These populations may be any assembly of sequences obtained from the methods described herein, including those based on mRNA, as well as certain species or classes of mRNA, other RNA species, or viral RNA.

The invention provides kits for carrying out the methods of the invention. Accordingly, a variety of kits are provided in suitable packaging. The kits may be used for any one or more of the uses described herein, and, accordingly, may contain instructions for any one or more of the following uses for samples comprising total nucleic acids: amplifying an RNA sequence; sequencing of an RNA sequence of interest; detection of sequence mutation based on amplifying an RNA sequence (e.g., genotyping or nucleic acid mutation detection); detection of an RNA sequence alteration including splice variants or fused transcripts; determining presence or absence of a sequence of interest; methods of gene expression analysis and profiling; methods of detection and quantification of RNA targets in samples comprising total nucleic acids; methods of whole transcriptome analysis for the detection, discovery, and/or quantification of sense or antisense transcripts, or coding and non-coding transcripts; methods of preparing amplification products for massively parallel analysis including massively parallel sequencing (e.g. pyrosequencing, sequencing by synthesis, sequencing by hybridization, single molecule sequencing, nanopore sequencing, and sequencing by ligation), high density PCR arrays, microarray hybridization, SAGE, digital PCR, and massively parallel Q-PCR; methods of subtractive hybridization; methods of preparing a subtractive hybridization probe; methods of differential amplification; methods of preparation of libraries (including cDNA and differential expression libraries); methods of preparation of an immobilized nucleic acid (which can be a nucleic acid immobilized on a microarray), and methods of characterizing amplified nucleic acid products generated by the methods of the invention.

The kits of the invention comprise one or more containers comprising any combination of the components described herein. Kits may include, but are not limited to, the following examples.

A kit may comprise any of the composite primers described herein with any of the listed DNA-dependent DNA polymerase inhibitors herein. In some embodiments, a kit comprises two or more composite primers, reverse transcriptase, and DNA-dependent DNA polymerase inhibitors, which may or may not be separately packaged. A kit may comprise a composite primer and a polynucleotide comprising a propromoter sequence, which may be a PTO, with DNA-dependent DNA polymerase inhibitors. A kit may further comprise a second primer, which can comprise a random primer. The composite primer may be labeled or unlabeled.

Kits may also optionally further include any of one or more of the enzymes described herein (for example, RNA-dependent DNA polymerase such as reverse transcriptase, and ribonuclease such as RNase H), as well as deoxynucleoside triphosphates (labeled or unlabeled) and/or ribonucleoside triphosphates (labeled or unlabeled) and/or nucleotide analogs and/or non-canonical nucleotides. Kits may also include one or more suitable buffers as described herein. Kits useful for nucleic acid sequencing may optionally include labeled or unlabeled nucleotide analogs that upon incorporation into a primer extension product or RNA transcript effect termination of nucleotide polymerization. The kits may comprise tailed deoxyoligonucleotides, wherein the tailed 5'-sequence is non-hybridizable to the target RNA and may further comprise a single-stranded DNA sequence of a promoter for DNA-dependent RNA polymerase.

The kits of the invention may optionally include a set of instructions, generally written instructions, although electronic storage media (e.g., magnetic diskette or optical disk) containing instructions are also acceptable, relating to the use of components of the methods of the invention for the intended nucleic acid amplification, and/or, as appropriate, for using the amplification products for purposes such as nucleic acid sequencing and detection of sequence mutation. The instructions included with the kit generally include information as to reagents (whether included or not in the kit) necessary for practicing the methods of the invention, instructions on how to use the kit, and/or appropriate reaction conditions. For example, kits of the invention can comprise: a composite primer (which can comprise a poly-dT portion and/or can be a random primer), a DNA-dependent DNA polymerase inhibitor(s), and instructions for using the primer with a DNA-dependent DNA polymerase inhibitor to amplify RNA according to methods of the invention. In another example, any of these kits further comprises one or more controls (which can be, for example, RNA template, composite primers, and/or double stranded cDNA complex (comprising first and second strand cDNA) comprising a 3'-single-stranded DNA portion).

One or more reagents in the kit can be provided as a dry powder, usually lyophilized, including excipients, which on dissolution will provide for a reagent solution having the appropriate concentrations for performing any of the methods described herein. Each component can be packaged in separate containers or some components can be combined in one container where cross-reactivity and shelf life permit. The component(s) of the kit may be packaged in any convenient, appropriate packaging. The components may be packaged separately, or in one or multiple combinations. Where kits are provided for practicing amplification methods of the invention that involve transcription, the RNA polymerase (if included) is preferably provided separately from the components used in the steps prior to the transcription steps.

The relative amounts of the various components in the kits can be varied widely to provide for concentrations of the reagents that substantially optimize the reactions that need to occur to practice the methods disclosed herein and/or to further optimize the sensitivity of any assay.

The following Examples are provided to illustrate, but not limit, the invention.

EXAMPLES

Example 1

Amplification of Sequences from a Target RNA in the Presence of DNA Using Actinomycin to Inhibit DNA-dependent DNA Polymerase Activity

A RNA target is amplified using a method involving a first primer, comprising composite RNA/DNA portions, wherein the 3'-DNA end of the primers comprises either poly-dT sequence or a random sequence. First strand cDNA synthesis is performed with this first primer in the presence of Actinomycin D, an inhibitor of DNA-dependent DNA polymerase. Removal of Actinomycin D and RNA target from the reaction mixture is performed by binding the nucleic acids to magnetic beads. Second strand cDNA synthesis is then carried out and is followed by amplification, which is performed using a composite amplification primer, DNA polymerase with strand displacement activity, and RNase H. The global RNA amplification was carried out using the WT-Ovation Pico amplification system (NuGEN Technologies Inc. www.nugeninc.com/html/03_products5.html) with additional reagents and protocol modifications described below. As described herein, the results of the example demonstrate selective amplification of RNA target from samples comprising mixtures of RNA and DNA.

Materials

All reagents for the WT-Ovation Pico RNA Amplification System (NuGEN Technologies Inc.) were used in this example. HeLa (S3) total RNA was purchased from Ambion. Human genomic DNA was purchased from Clontech. Random hexamer (N6 DNA oligonucleotide) was purchased from Operon. Actinomycin D was purchased from USB.

General Comments

The WT-Ovation Pico amplification system was used to perform global RNA amplification. For selective amplification of RNA targets from samples comprising genomic DNA, the procedure was modified to include Actinomycin D in the step involving first strand cDNA synthesis. Additional clean up following first strand cDNA synthesis was added to the manufacturer protocol, which result in the removal of Actinomycin D prior to second strand cDNA synthesis. In addition, second strand cDNA synthesis was carried out in the presence of random hexamers (DNA oligonucleotides). All other steps were the same as for the WT-Ovation Pico RNA Amplification System.

First Strand cDNA Synthesis

First stand cDNA synthesis is initiated randomly across the length of RNA transcripts using composite first primers containing a 3'-random sequence DNA portion (for example, a random hexamer sequence) and a 5'-non-complementary and non-hybridizable RNA portion. In addition to the composite first primer, another composite first primer, comprising a 3'-poly-DT sequence DNA portion and the same 5'-non-hybridizing RNA portion as the previous primer, is used. In both the WT-Ovation Pico RNA amplification protocol and the modified procedure of the current invention, 1 to 2 µl of total RNA sample comprising 0.5 to 50 ng total RNA purified from a sample to be analyzed, with or without DNA, are mixed with 1 to 2 µl of a mixture containing the two first primers. The resulting mixture was transferred to a heating block or a thermal cycler and incubated at 65° C. for 2 minutes. The mixture is then removed from the heating block or thermocycler and placed on ice.

A second mixture containing reverse transcriptase and a buffer were added to the first mixture above to a total volume of 10 µl. In samples subjected to the selective RNA amplification, Actinomycin D was added to the mixture to a final concentration of 50 ng/µl. The reactions were carried out by incubation at the following temperatures and durations: 4° C. for 1 min, 25° C. for 10 min, 42° C. for 10 min, 70° C. for 15 min., 4° C. and hold. The reaction mixture is then placed on ice.

Removal of Actinomycin D

Prior to second strand cDNA synthesis, removal of the DNA-dependent DNA polymerase and Actinomycin D is performed using magnetic beads under conditions that allow binding of the nucleic acids in the mixture to the beads. This clean up step allows separation of the reaction medium containing Actinomycin D from the nucleic acids and was conducted following the manufacturer instructions. To the reaction mixture above, 16 µl of bead suspensions (RNAClean, Agencourt) were added and the mixture was incubated at room temperature for 10 min. The beads were separated using a magnetic plate and the supernatant was discarded. The beads with the bound nucleic acids from the above reaction mixture were washed three times with 70% ethanol and air dried for 10 min at room temperature. This clean up step was performed for samples subjected to the selective RNA amplification according to the method of the invention and is a modified protocol of the WT-Ovation Pico RNA amplification.

Second Strand cDNA Synthesis

A mixture of DNA polymerase and buffer was added to the first strand synthesis reaction mixture for synthesis of the second strand cDNA. In the case of the modified protocol for selective RNA amplification according the method of the current invention, the reaction mixture also contained random hexamers (N6 DNA oligonucleotides) at 100 ng/µl. Second strand cDNA synthesis was carried out in a total volume of 20 µl. For selective RNA amplification according to the method of the current invention, the beads used for the removal of Actinomycin D, as described above, were left in the second strand cDNA synthesis reaction mixture. Second strand cDNA synthesis reactions were carried out by incubation at the following temperatures for the following durations: 4° C. for 1 min, 25° C. for 10 min, 50° C. for 30 min, 70° C. for 5 min, and cooled to 4° C.

Purification of the Double Stranded cDNA

To each second strand cDNA reaction mixture, 32 µl of bead suspension (RNAClean® Agencourt) were added and the mixture was incubated for 10 min at room temperature. The beads were separate on a magnetic plate and further processed as described herein.

Amplification

Amplification was carried out according to the manufacturer's instruction with modification of the total reaction volume from 160 µl to 80 µl (www.nugeninc.com).

Beads were suspended in the amplification mixture containing 20 µl of composite amplification primer, 40 µl of reaction buffer, and 20 µl enzyme mixture. The amplification reactions were carried out at following temperatures and durations: 40° C. for 1 min., 47° C. for 60 min., and 95° C. for 5 min. The reaction were cooled to 4° C. and held at this temperature until purification of the amplification products.

Results

The selective amplification of RNA from samples comprising low levels of input total HeLa RNA, with or without excess genomic human DNA, employed a modified protocol of the WT-Ovation Pico RNA amplification system, which included Actinomycin D in the first strand cDNA synthesis (to inhibit DNA-dependent DNA polymerase) and removal of Actinomycin D prior to second strand cDNA synthesis. The results from selective RNA amplification from a sample comprising DNA, are shown in Table 1, and includes the yield of amplified cDNA products generated by the non-modified protocol and the modified protocol, which is designed according to the method of the current invention. In control reactions, the selective amplification of RNA is demonstrated by the marked reduction in the yield of amplification products from samples comprising only genomic DNA and no RNA.

TABLE 1

| Input | | Yield μg SPIA ™ amplified cDNA | |
|---|---|---|---|
| RNA | DNA | WT-Ovation Pico | Selective RNA amplification |
| 1 ng | | 5.92 | 5.86 |
| | | 5.56 | 5.34 |
| 1 ng | 1 ng | 5.80 | 5.02 |
| | | 4.46 | 5.65 |
| 1 ng | 9 ng | 5.83 | 5.76 |
| | | 5.53 | 5.68 |
| No RNA | 9 ng | 4.82 | 2.66 |
| | | 5.24 | 2.31 |
| No RNA | No DNA | 1.00 | 0.74 |
| | | 0.85 | 0.76 |

The amplified cDNA was further quantified by analysis of various transcripts in the amplification products using real time PCR. Aliquots of non-purified amplification products were diluted 1:80 in Tris-EDTA and 2 μl of the diluted amplification products were added to PCR mixture with SYBR Green and the specified PCR primers (sequence information given in Table 3). Relative quantification is given by Ct values for the various measured transcripts (amplified cDNA) in Table 2.

TABLE 3

PCR primer pairs used for quantification by real time PCR (SEQ ID NOS 1-8, respectively, in order of appearance)

| Assay | PCR Primer sequences | Gene |
|---|---|---|
| GAPE-12 | tccactggcgtcttcacc ggcagagatgatgaccctttt | glyceraldehyde-3-phosphate dehydrogenase |
| CD44-3 | ttgttactttgacttttcagagcac gcaatatacatatcatgctttcctca | CD44 antigen (homing function and Indian blood group system) |
| CD44-1 | gacaccatggacaagttttgg cggcaggttatattcaaatcg | CD44 antigen (homing function and Indian blood group system) |
| PGK1 | ctgtggcttctggcatacct cttgctgctttcaggacca | phosphoglycerate kinase 1 |

Example 2

Whole Transcriptome Analysis of Sequences from Total RNA in the Presence of DNA Using Actinomycin to Inhibit DNA-dependent DNA Polymerase Activity A RNA target is amplified using a method involving a first primer, comprising composite RNA/DNA portions, wherein the 3'-DNA end of the primers comprises either poly-dT sequence or a random sequence. First strand cDNA synthesis is performed with this first primer in the presence of Actinomycin D, an inhibitor of DNA-dependent DNA polymerase. Removal of Actinomycin D and RNA target from the reaction mixture is performed by binding the nucleic acids to magnetic beads. Second strand cDNA synthesis is then carried out and is followed by amplification, which is performed using a composite amplification primer, DNA polymerase with strand displacement activity, and RNase H. The global RNA

TABLE 2

Real time PCR quantification of specific amplified cDNA products (non-purified)

| Input | | PGK-1 (Ct) | | GAPE 12 (Ct) | | CD44-1 (Ct) | | CD44-3 (Ct) | |
|---|---|---|---|---|---|---|---|---|---|
| RNA | DNA | WT-Ovation Pico | Selective amplification | WT-Ovation Pico | Selective amplification | WT-Ovation Pico | Selective amplification | WT-Ovation Pico | Selective amplification |
| 1 ng | No DNA | 19.1 | 18.8 | 17.2 | 18.1 | 23.3 | 20.4 | 19.2 | 21.4 |
| | | 18.9 | 19.7 | 17.9 | 16.5 | 22.5 | 20.7 | 18.8 | 22.2 |
| 1 ng | 1 ng | 19.0 | 18.9 | 17.8 | 17.5 | 23.4 | 21.6 | 18.2 | 22.0 |
| | | 19.1 | 19.2 | 17.8 | 17.5 | 22.8 | 21.4 | 18.0 | 22.0 |
| 1 ng | 9 ng | 19.9 | 19.3 | 18.2 | 18.0 | 23.3 | 20.8 | 20.0 | 20.3 |
| | | 19.3 | 19.5 | 18.1 | 18,2 | 23.1 | 21.7 | 19.1 | 21.8 |
| No RNA | 9 ng | 33.3 | None | 29.2 | 34.3 | None | None | 35.1 | 28.4 |
| | | 23.2 | 35.9 | 31.5 | 33.0 | None | None | 33.2 | 34.7 |
| No RNA | No DNA | None | None | 39.5 | None | None | None | None | None |
| | | None | 38.5 | 35.6 | 36.4 | None | None | None | None | amplification is carried out using the WT-Ovation Pico amplification system (NuGEN Technologies Inc. www.nugeninc.com/html/03_products5.html) with additional reagents and protocol modifications described below. The amplification products are then analyzed by sequencing with a Genome Sequencer platform (454/Roche Lifesciences). As described herein, the results of the example demonstrate selective amplification and analysis of RNA target from samples comprising mixtures of RNA and DNA.

Materials

All reagents for the WT-Ovation Pico RNA Amplification System (NuGEN Technologies Inc.) are used in this example. HeLa (S3) total RNA is purchased from Ambion. Human genomic DNA is purchased from Clontech. Random hexamer (N6 DNA oligonucleotide) is purchased from Operon. Actinomycin D is purchased from USB.

General Comments

The WT-Ovation Pico amplification system is used to perform global RNA amplification. For selective amplification of RNA targets from samples comprising genomic DNA, the procedure is modified to include Actinomycin D in the step involving first strand cDNA synthesis. Additional clean up following first strand cDNA synthesis is added to the manufacturer protocol, which results in the removal of Actinomycin D prior to second strand cDNA synthesis. In addition, second strand cDNA synthesis is carried out in the presence of random hexamers (DNA oligonucleotides). All other amplification steps are the same as for the WT-Ovation Pico RNA Amplification System. The sequencing analysis is performed according to the manufacturers instructions.

First Strand cDNA Synthesis

First stand cDNA synthesis is initiated randomly across the length of RNA transcripts using composite first primers containing a 3'-random sequence DNA portion (for example, a random hexamer sequence) and a 5'-non-complementary and non-hybridizable RNA portion. In addition to the composite first primer, another composite first primer, comprising a 3'-poly-DT sequence DNA portion and the same 5'-non-hybridizing RNA portion as the previous primer, is used. In both the WT-Ovation Pico RNA amplification protocol and the modified procedure of the current invention, 1 to 2 µl of total RNA sample comprising 0.5 to 50 ng total RNA purified from a sample to be analyzed, with or without DNA, are mixed with 1 to 2 µl of a mixture containing the two first primers. The resulting mixture is transferred to a heating block or a thermal cycler and incubated at 65° C. for 2 minutes. The mixture is then removed from the heating block or thermocycler and placed on ice.

A second mixture containing reverse transcriptase and a buffer is added to the first mixture above to a total volume of 10 µl. In samples subjected to the selective RNA amplification, Actinomycin D is added to the mixture to a final concentration of 50 ng/µl. The reactions are carried out by incubation at the following temperatures and durations: 4° C. for 1 min, 25° C. for 10 min, 42° C. for 10 min, 70° C. for 15 min., 4° C. and hold. The reaction mixture is then placed on ice.

Removal of Actinomycin D

Prior to second strand cDNA synthesis, removal of the DNA-dependent DNA polymerase and Actinomycin D is performed using magnetic beads under conditions that allow binding of the nucleic acids in the mixture to the beads. This clean up step allows separation of the reaction medium containing Actinomycin D from the nucleic acids and is conducted following the manufacturer instructions. To the reaction mixture above, 16 µl of bead suspensions (RNAClean, Agencourt) are added and the mixture is incubated at room temperature for 10 min. The beads are separated using a magnetic plate and the supernatant is discarded. The beads with the bound nucleic acids from the above reaction mixture are washed three times with 70% ethanol and air dried for 10 min at room temperature. This clean up step is performed for samples subjected to the selective RNA amplification according to the method of the invention and is a modified protocol of the WT-Ovation Pico RNA amplification.

Second Strand cDNA Synthesis

A mixture of DNA polymerase and buffer is added to the first strand synthesis reaction mixture for synthesis of the second strand cDNA. In the case of the modified protocol for selective RNA amplification according to the method of the current invention, the reaction mixture also contains random hexamers (N6 DNA oligonucleotides) at 100 ng/µl. Second strand cDNA synthesis is carried out in a total volume of 20 µl. For selective RNA amplification according to the method of the current invention, the beads used for the removal of Actinomycin D, as described above, are left in the second strand cDNA synthesis reaction mixture. Second strand cDNA synthesis reactions are carried out by incubation at the following temperatures for the following durations: 4° C. for 1 min, 25° C. for 10 min, 50° C. for 30 min, 70° C. for 5 min, and cooled to 4° C.

Purification of the Double Stranded cDNA

To each second strand cDNA reaction mixture, 32 µl of bead suspension (RNAClean® Agencourt) are added and the mixture is incubated for 10 min at room temperature. The beads are separated on a magnetic plate and further processed as described herein.

Amplification

Amplification is carried out according to the manufacturer's instruction with modification of the total reaction volume from 160 µl to 80 µl (www.nugeninc.com).

Beads are suspended in the amplification mixture containing 20 µl of composite amplification primer, 40 µl of reaction buffer, and 20 µl enzyme mixture. The amplification reactions are carried out at following temperatures and durations: 40° C. for 1 min., 47° C. for 60 min., and 95° C. for 5 min. The reactions are cooled to 4° C.

Analysis

The amplified polynucleotides are diluted 1,000-fold, immobilized onto beads, and compartmentalized in a water-in-oil emulsion in the presence of PCR primers and reagents including buffer, enzyme and dNTP's. The immobilized polynucleotides are amplified by thermocycling in the water-in-oil emulsion for 20 cycles. When the emulsion is broken, amplified fragments remain bound to the beads. The beads are enriched to select for optimally sized amplicons and loaded into wells of a fiber optic slide so that there is approximately 1 bead in each well. Nucleotides are flowed across and into the wells in a fixed order in the presence of polymerase, sulfhydrolase, and luciferase. Addition of nucleotides complementary to the target strand results in a chemiluminescent signal that is recorded by a camera. The combination of signal intensity and positional information generated across the plate allows software to determine the DNA sequence.

Results

The selective amplification of RNA from samples comprising low levels of input total HeLa RNA, with or without excess genomic human DNA, employs a modified protocol of the WT-Ovation Pico RNA amplification system, which includes Actinomycin D in the first strand cDNA synthesis (to inhibit DNA-dependent DNA polymerase) and removal of Actinomycin D prior to second strand cDNA synthesis. The resulting selectively amplified polynucleotide targets are then used to perform whole-transcriptome analysis by massively parallel sequencing. The massively parallel sequencing identifies: (i) transcript abundance at both the exon and transcript level; (ii) transcriptional start and stop sites; (iii) exon-exon linkages in mature transcripts; (iv) single-base changes corresponding to SNPs and mutations; and (v) novel exons belonging to already characterized genes. The massively parallel sequencing also provides numerous examples of novel splicing events when the reads that could not be mapped directly to the genome were searched against a database of all possible exon-exon junctions within and between genes. A large number of reads appear to represent bona fide transcripts of novel expressed elements. The sequence data also allows the identification of single-base variations corresponding to novel SNPs and mutations, with many of these genes either cell cycle—or E2F transcription—related.

Although the foregoing invention has been described in some detail by way of illustration and example for purposes of clarity of understanding, it will be apparent to those skilled in the art that certain changes and modifications may be practiced. Therefore, the descriptions and examples should not be construed as limiting the scope of the invention, which is delineated by the appended claims.

While preferred embodiments of the present invention have been shown and described herein, it will be obvious to those skilled in the art that such embodiments are provided by way of example only. Numerous variations, changes, and substitutions will be apparent to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of selectively generating multiple copies of a polynucleotide sequence of or complementary to target RNA which is in a sample comprising DNA, said method comprising the steps of:

(a) hybridizing to the target RNA in said sample a first primer comprising a sequence (A) that is not complementary to the target RNA, and a sequence (B) at the 3'-end which hybridizes to the target RNA;

(b) extending the first primer with at least one enzyme comprising RNA-dependent DNA polymerase activity in the presence of at least one compound comprising DNA-dependent DNA polymerase inhibitor activity, whereby DNA-dependent DNA polymerase activity of the enzyme comprising RNA-dependent DNA polymerase activity is inhibited by said compound, whereby a complex comprising a primer extension product and the target RNA is produced, whereby the first primer extension product comprises a sequence (Y) that is complementary to the target RNA and comprises sequence (A);

(c) disabling or removing at least one compound comprising DNA-dependent DNA polymerase inhibitor activity; and (d) producing multiple copies of a polynucleotide sequence complementary to the target RNA and/or complementary to sequence (Y) using sequence (A).

2. A method of selectively generating multiple copies of a polynucleotide sequence complementary to a target RNA which is in a sample comprising DNA, said method comprising the steps of:

(a) hybridizing to the target RNA a first primer comprising a sequence (A) that does not hybridize to the target RNA, and a sequence (B) at the 3'-end, which hybridizes to the target RNA;

(b) extending the first primer with at least one enzyme comprising RNA-dependent DNA polymerase activity in the presence of at least one compound comprising DNA-dependent DNA polymerase inhibitor activity, whereby a complex comprising a first primer extension product and the target RNA is produced, whereby the first primer extension product comprises a sequence (Y) that is complementary to the target RNA and comprises sequence (A);

(c) disabling or removing at least one compound comprising DNA-dependent DNA polymerase inhibitor activity;

(d) cleaving the target RNA in the complex of step (b);

(e) extending a second primer along the first primer extension product with at least one enzyme comprising DNA-dependent DNA polymerase activity, wherein the second primer comprises sequence (C) that is complementary to a sequence (C') on the first primer extension product to produce a complex comprising the first primer extension product and a second primer extension product, whereby the second primer extension product comprises the sequence (C), a sequence (Y') complementary to sequence (Y) and sequence (A') complementary to sequence (A);

(f) producing multiple copies of a polynucleotide sequence complementary to the target RNA using a primer with a sequence (A) and/or sequence (A').

3. The method of claim 1 or 2, wherein the first primer comprises a 5'sequence that is not hybridizable to the target RNA.

4. The method of claims 1 or 2, wherein the method further comprises clonally producing on a solid substrate or in an emulsion multiple copies of a polynucleotide sequence complementary to the target RNA using a primer with a sequence (A) and/or sequence (A').

5. The method of claim 3, wherein the sequence (A') is used as a priming site for amplification.

6. The method of claim 3, wherein the producing of multiple copies in step (f) are produced using amplification methods comprising polymerase chain reaction (PCR).

7. The method of claim 6, wherein a PCR primer comprises sequence (A) of the first primer.

8. The method of claim 7, wherein a PCR primer comprises sequence (C) of the second primer.

9. The method of claim 7, wherein the producing of multiple copies in step (f) comprises performing PCR with primer pairs wherein the first PCR primer is complementary to sequence (A') and the second PCR primer is complementary to all or a portion of sequence (C') or all or a portion of sequence (Y).

10. The method of claim 6 wherein the producing of multiple copies in step (f) comprises performing single primer, linear PCR using a PCR primer complementary to sequence (A').

11. The method of claim 3 wherein the producing of multiple copies in step (f) comprises an amplification method comprising the use of an RNA/DNA composite primer, RNase H, and a DNA dependent DNA polymerase with strand displacement activity.

12. The method of claim 1 or 2, wherein the first primer comprises an RNA and a DNA sequence wherein a 5'-RNA sequence comprises sequence (A) and a 3'-DNA sequence comprises sequence (B); whereby the complex formed in step (e) comprises an RNA/DNA heteroduplex at one end; and wherein the producing of multiple copies in step (f) comprises the steps of (i) cleaving the RNA from the heteroduplex, (ii) hybridizing to sequence (A') an amplification primer comprising a 5' RNA sequence and a 3' DNA sequence, (iii) extending the amplification primer with at least one enzyme comprising DNA dependent DNA polymerase activity and comprising strand displacement activity, (iv) cleaving the RNA from the extended amplification primer in the heteroduplex with at least one enzyme comprising a specificity for cleaving RNA in a DNA-RNA heteroduplex; and (v) repeating steps (ii) through (iv) to produce multiple copies of amplification product comprising sequence (Y) that is complementary to a portion of the RNA template.

13. The method of claim 1 or 2, wherein the producing of multiple copies comprises in-vitro-transcription (IVT).

14. The method of claim 13 wherein sequence (A) comprises a pro-promoter, whereby the complex formed in step (e) comprises a double stranded promoter for a DNA dependent RNA polymerase comprising sequences (A) and (A'), wherein (A) is a DNA sequence.

15. The method of claim 2, wherein the second primer comprises a fragment from the cleaved RNA target.

16. The method of claim 1 or 2, wherein the DNA-dependent DNA polymerase inhibitor activity is derived from a compound comprising at least one of the following:
  actinomycin, alpha-amanitin, aphidicolin, BP5, novobiocin, rifampicin, rifamycin, sulfoquinovosylmonoacylglycerol, sulfoquinovosyldiacylglycerol, ursane, oleanane triterpenoids, ursolic acid, oleanolic acid, mikanolide, dihydromikanolide, dehydroaltenusin, catapol, taxinine, cephalomanninine, dipeptide alcohols, corylifolin; bakuchiol; resveratrol; Neobavaisoflavone; daidzein; bakuchicin, levodopa, dopamine, anacardic acid and oleic acid.

17. The method of claim 1 or 2, wherein the DNA-dependent DNA polymerase inhibitor activity is derived from a compound comprising actinomycin.

18. The method of claim 1 or 2, wherein the sample comprises total nucleic acid in a biological fluid.

19. The method of claim 18, wherein the biological fluid is selected from the group consisting of: plasma, serum, urine, saliva.

20. The method of claim 1 or 2, wherein the sample comprises viral RNA.

21. The method of claim 1 or 2, wherein the sample comprises cell or tissue lysates.

22. The method of claim 1 or 2, wherein the second primer comprises a tailed primer with a 5'-sequence which does not hybridize to the first primer extension product and which comprises a propromoter sequence such that RNA transcripts are produced comprising a sequence homologous to the target RNA; whereby multiple copies of the homologous sequence of the RNA sequence of interest are generated.

23. The method of claim 1 or 2, wherein the producing of multiple copies in step (f) comprises hybridizing a PTO, comprising a propromoter sequence and a 3'-hybridizing region, to the 3'-end of a first primer extension product under conditions which allow transcription to occur by RNA polymerase, such that RNA transcripts are produced comprising sequences homologous to the target RNA; whereby multiple copies of the RNA sequence of interest are generated.

24. The method of claim 1 or 2, wherein the producing of multiple copies in step (f) comprises hybridizing a PTO, comprising a propromoter sequence and a 3'-hybridizing region, to the 3'-end of a second primer extension under conditions which allow transcription to occur by RNA polymerase, such that RNA transcripts are produced comprising sequences complementary to the target RNA; whereby multiple copies of the complementary sequence of the RNA sequence of interest are generated.

25. The method of claim 1 or 2, wherein the target RNA is mRNA.

26. The method of claim 1 or 2, wherein the first primer comprises a sequence complementary to poly-A on RNA.

27. The method of claim 1 or 2, wherein the sequence (B) which hybridizes to the target RNA comprises a random sequence.

28. The method of claim 1 or 2, wherein the first primer comprises a mixture of first primers comprising a first primer comprising a sequence complementary to poly-A on RNA, and further comprising a first primer comprising a sequence which hybridizes to the target RNA and comprises a random sequence.

29. The method of claim 15, wherein said fragment is generated by cleaving RNA in the complex of step (b) with an enzyme that cleaves RNA from an RNA/DNA heteroduplex, by heat, or by chemical means.

30. The method of claim 1 or 2, wherein said method comprises generating multiple copies of two or more different sequences of interest.

31. The method of claim 30, wherein said method comprises at least two different first primers.

32. The method of claim 2, wherein cleaving the RNA in a heteroduplex of the RNA target and the first primer extension product is performed by RNase H.

33. A method of sequencing an RNA sequence of interest, said method comprising analyzing amplification products to determine sequence, said amplification products produced by the method of any of claim 1 or 2 in the presence of a mixture of NTPs and NTP analogs such that transcription is terminated upon incorporation of an NTP analog 34. The method of claim 33, wherein the target RNA is mRNA, a whole transcriptome or substantial fraction thereof, or a set of whole transcriptomes or substantial fractions thereof.

35. A method of detecting a mutation in a target RNA, comprising analyzing sequences of amplification products for the presence of a mutation as compared to a reference polynucleotide sequence, said amplification products produced by the method of any of claims 1 or 2.

36. The method of claim 35, wherein the target RNA is mRNA.

37. A method of producing a nucleic acid immobilized to a substrate comprising immobilizing amplification products on a substrate, said amplification products produced by the method of any of claim 1 or 2.

38. The method of claim 37, wherein the target RNA is mRNA.

39. The method of claim 37, wherein the substrate is a microarray.

40. A method for performing expression analysis of one or more target RNA sequences comprising:
   (a) collecting a sample of nucleic acid comprising RNA and DNA;
   (b) optionally enriching the nucleic acid in the sample;
   (c) contacting the nucleic acid with an inhibitor of DNA-dependent DNA polymerase activity;
   (d) hybridizing to the target RNA a first primer comprising a sequence (A) that is not complementary to the target RNA, and a sequence (B) at the 3'-end which hybridizes to the target RNA;
   (e) extending the first primer with at least one enzyme comprising RNA-dependent DNA polymerase activity in the presence of at least one compound comprising DNA-dependent DNA polymerase inhibitor activity, whereby DNA-dependent DNA polymerase activity of the enzyme comprising RNA-dependent DNA polymerase activity is inhibited by the compound, whereby a complex comprising a primer extension product and the target RNA is produced, whereby the first primer extension product comprises a sequence (Y) that is complementary to the target RNA and comprises sequence (A);
   (f) disabling or removing at least one compound comprising DNA-dependent DNA polymerase inhibitor activity;
   (g) producing multiple copies of a polynucleotide sequence complementary to the target RNA and/or complementary to sequence (Y) using sequence (A); and
   (h) further analyzing the amplified products of step (g).

41. The method of claim 40, wherein step (h) further analyzing the products of step (g) includes whole transcriptome analysis, whole transcriptome profiling, microarray analysis, quantitative PCR, pyrosequencing, sequencing by ligation, dye-terminator sequencing, whole transcriptome sequencing, RNA sequencing by massively parallel sequencing, or digital PCR.

42. The method of claim 40, wherein the DNA-dependent DNA polymerase inhibitor activity is derived from a compound comprising at least one of the following: actinomycin, alpha-amanitin, aphidicolin, BP5, novobiocin, rifampicin, rifamycin, sulfoquinovosylmonoacylglycerol, sulfoquinovosyldiacylglycerol, ursane, oleanane triterpenoids, ursolic acid, oleanolic acid, mikanolide, dihydromikanolide, dehydroaltenusin, catapol, taxinine, cephalomanninine, dipeptide alcohols, corylifolin, bakuchiol, resveratrol, Neobavaisoflavone, daidzein, bakuchicin, levodopa, dopamine, anacardic acid and oleic acid.

43. The method of claim 40, wherein step (g) comprises PCR, linear PCR, in vitro transcription, or single primer isothermal amplification.

44. A method of generating at least one double stranded DNA product corresponding to a sequence of a target RNA or a portion thereof comprising:
   (a) adding to a reaction mixture comprising target RNA and further comprising DNA:
     (i) at least one first primer comprising a 3' annealing sequence and a 5'tail sequence;
     (ii) at least one DNA-dependent DNA polymerase inhibitor; and
     (iii) an RNA-dependent DNA polymerase having DNA-dependent DNA polymerase activity that is inhibited by the at least one compound that is a DNA-dependent DNA polymerase inhibitor;
   (b) disabling or removing the at least one DNA-dependent DNA polymerase inhibitor from the reaction mixture;
   (c) annealing and extending at least one all-DNA second primer comprising an annealing sequence with a DNA-dependent DNA polymerase, wherein said double stranded product is labeled at at least one end; and
   (d) clonally amplifying one or both strands of the double-stranded product.

45. The method of claim 44, wherein the clonal amplification is performed on a solid substrate, in an emulsion, or both.

46. The method of claim 44, wherein the clonal amplification generates polonies.

* * * * *

```
                              SEQUENCE LISTING

<160> NUMBER OF SEQ ID NOS: 8

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tccactggcg tcttcacc                                                        18

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggcagagatg atgaccettt t                                                    21

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ttgttacttt gacttttcag agcac                                                25

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
```

-continued

```
gcaatataca tatcatgctt tcctca                                          26

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gacaccatgg acaagttttg g                                               21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cggcaggtta tattcaaatc g                                               21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctgtggcttc tggcatacct                                                 20

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cttgctgctt tcaggacca                                                  19
```